(12) United States Patent
Meyer et al.

(10) Patent No.: US 9,131,690 B2
(45) Date of Patent: Sep. 15, 2015

(54) MACROCYCLIC PICOLINAMIDES AS FUNGICIDES

(71) Applicant: Dow AgroSciences LLC, Indianapolis, IN (US)

(72) Inventors: Kevin G. Meyer, Zionsville, IN (US); Fangzheng Li, Carmel, IN (US); James M. Renga, Indianapolis, IN (US); W. John Owen, Carmel, IN (US); Benjamin M. Nugent, Brownsburg, IN (US); Chenglin Yao, Westfield, IN (US); Nick X. Wang, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 33 days.

(21) Appl. No.: 13/887,726

(22) Filed: May 6, 2013

(65) Prior Publication Data

US 2013/0296371 A1 Nov. 7, 2013

Related U.S. Application Data

(60) Provisional application No. 61/643,623, filed on May 7, 2012.

(51) Int. Cl.
| | |
|---|---|
| C07D 405/14 | (2006.01) |
| A01N 43/40 | (2006.01) |
| A01N 43/647 | (2006.01) |
| A01N 43/54 | (2006.01) |
| C07D 405/12 | (2006.01) |

(52) U.S. Cl.
CPC ............... *A01N 43/40* (2013.01); *A01N 43/54* (2013.01); *A01N 43/647* (2013.01); *C07D 405/12* (2013.01); *C07D 405/14* (2013.01)

(58) Field of Classification Search
CPC ............................. C07D 405/12; C07D 405/14
See application file for complete search history.

(56) References Cited

U.S. PATENT DOCUMENTS

| | | | |
|---|---|---|---|
| 6,355,660 B1 | 3/2002 | Ricks et al. | |
| 6,521,622 B1 | 2/2003 | Ricks et al. | |
| 6,706,740 B2 | 3/2004 | Ricks et al. | |
| 6,861,390 B2 | 3/2005 | Meyer et al. | |
| 7,250,389 B1 | 7/2007 | Sakanaka et al. | |
| 2004/0171838 A1 | 9/2004 | Meyer et al. | |
| 2004/0186296 A1 | 9/2004 | Niyaz et al. | |
| 2004/0192924 A1 | 9/2004 | Meyer et al. | |
| 2007/0060579 A1 | 3/2007 | Wachendorff-Neumann et al. | |
| 2007/0066629 A1 | 3/2007 | Blasco et al. | |
| 2011/0082160 A1 | 4/2011 | Owen et al. | |

FOREIGN PATENT DOCUMENTS

| | | |
|---|---|---|
| EP | 1 516 874 | 3/2005 |
| WO | WO 0114339 A2 * | 3/2001 |
| WO | WO 2012/070015 | 5/2012 |

OTHER PUBLICATIONS

Usuki et al., "UK-2A,B,C and D, novel antifungal antibiotics from *Streptomyces* sp. 517-02 VI (2). Strucucture-activity relationships of UK-2A", The Journal of Antibiotics, Jun. 2002, 55(6), pp. 607-610.*

International Searching Authority, International Search Report and Written Opinion for PCT/US2013/039735, dated Oct. 18, 2013., 8 pages.

Anonymous, Synergistic Fungicidal Compositions of Heterocyclic Aromatic Amides and Triazoles, IP.com, Electronic Publication, 2004, 1-10.

* cited by examiner

*Primary Examiner* — Kendra D Carter

(74) *Attorney, Agent, or Firm* — C. W. Arnett; Faegre Baker Daniels LLP

(57) ABSTRACT

The disclosure relates to macrocyclic picolinamides of Formula I and their use as fungicides.

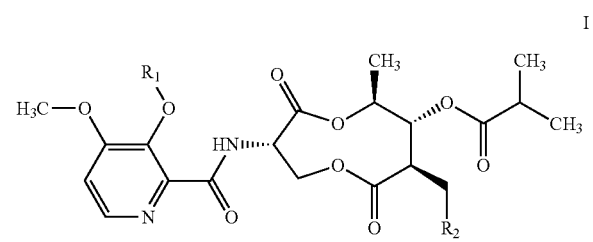

6 Claims, No Drawings

MACROCYCLIC PICOLINAMIDES AS FUNGICIDES

CROSS REFERENCE TO RELATED APPLICATIONS

This application claims the benefit of U.S. Provisional Patent Application Ser. No. 61/643,623 filed May 7, 2012, which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

I $R_1$ is H, —C(O)$R_3$, or —CH$_2$OC(O)$R_3$;

$R_2$ is H, halogen, alkyl, alkenyl, alkynyl, aryl, heterocyclyl, alkylthio, arylthio or heteroarylthio each substituted with 0, 1 or multiple $R_5$, —CH$_2$$R_4$, —CH$_2$OC(O)$R_4$, —C(O)O$R_4$, —CH$_2$OS(O)$_2$$R_4$, or —CH$_2$O$R_4$;

$R_3$ is alkyl or alkoxy, substituted with 0, 1, or multiple $R_5$;

$R_4$ is H, alkyl, alkenyl, aryl, arylalkyl, or heterocyclyl, each substituted with 0, 1 or multiple $R_5$;

$R_5$ is alkyl, alkenyl, halo, haloalkyl, alkoxy, haloalkoxy, arylalkoxy, cyano, aryl or heterocyclyl, each substituted with 0, 1 or multiple $R_6$; and $R_6$ is alkyl, alkenyl, halo, haloalkyl, alkoxy, haloalkoxy, arylalkoxy, cyano, aryl or heterocyclyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by the those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or cyclic saturated carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclohexenyl, and the like.

The term "alkynyl" refers to a branched or unbranched carbon chain containing one or more triple bonds including, but not limited to, propynyl, butyryl and the like.

The term "aryl" refers to any aromatic, mono- or bi-cyclic, containing 0 heteroatoms.

The term "heterocyclyl" refers to any aromatic or non-aromatic ring, mono- or bi-cyclic, containing one or more heteroatoms The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "haloalkylsulfonyl" refers to an —SO$_2$—R substituent where R is fully or partially substituted with Cl, F, I, or Br or any combination thereof.

The term "alkylthio" refers to an —S—R substituent.

The term "haloalkylthio" refers to an alkylthio, which is substituted with Cl, F, I, or Br or any combination thereof.

The term "alkylaminocarbonyl" refers to a —C(O)—N(H)—R substituent.

The term "dialkylaminocarbonyl" refers to a —C(O)—NR$_2$ substituent.

The term "alkylcycloalkylamino" refers to a cycloalkylamino substituent that is substituted with an alkyl group.

The term "trialkylsilyl" refers to —Si(R)$_3$.

The term "cyano" refers to a —C≡N substituent.

The term "hydroxyl" refers to an —OH substituent.

The term "amino" refers to a —NH$_2$ substituent.

The term "alkylamino" refers to a —N(H)—R substituent.

The term "dialkylamino" refers to a —N(R)$_2$ substituent.

The term "alkoxyalkoxy" refers to —O(CH$_2$)$_n$O(CH$_2$)$_n$ where n is an integer from 1-3.

The term "alkoxyalkyl" refers to an alkoxy substitution on an alkyl.

The term "arylalkoxy" refers to —O(CH$_2$)$_n$Ar where n is an integer selected from the list 1, 2, 3, 4, 5, or 6.

The term "arylalkyl" refers to —(CH$_2$)$_n$Ar where n is an integer selected from the list 1, 2, 3, 4, 5, or 6.

The term "haloalkoxyalkyl" refers to an alkoxy substitution on an alkyl which may be partially substituted with halogen atoms.

The term "hydroxyalkyl" refers to an alkyl which is substituted with a hydroxyl group.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —NO$_2$ substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrates, or emulsifiable concentrates.

In some embodiments, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8 EO); tallow amine ethoxylate (15 EO); PEG(400) dioleate-99. The formulations may also include oil-in-water emulsions such as those disclosed in U.S. patent application Ser. No. 11/495, 228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis (dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, amino cyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungicidal pathogens. Exemplary pathogens may include, but are not limited to, wheat leaf blotch (*Septoria tritici*, also known as *Mycosphaerella graminicola*), brown rust (*Puccinia triticina*), stripe rust (*Puccinia striiformis*), and black sigatoka (*Mycosphaerella fujiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

As shown in Scheme 1, step a, a compound of Formula III can be prepared via protection of Formula II with a protecting group, for example, tert-butoxycarbonyl (Boc) to give a tert-butylcarbamate, followed by cleavage of the picolinate head under alkaline conditions, such as those achieved with N,N-diethylethylenediamine. Compounds of Formula IVa can then be prepared under oxidative conditions, for example, with sodium periodate ($NaIO_4$) and ruthenium trichloride ($RuCl_3$) in a solvent system such as acetonitrile ($CH_3CN$), ethyl acetate (EtOAc) and water ($H_2O$). Compounds of Formula V, where X is halogen, for example, iodo and bromo, can be prepared from compounds of Formula IVa by treatment with 2-mercaptopyridine-N-oxide, and irradiation or heating of the resultant ester in the presence of a halogen source, for example iodoform and bromotrichloromethane, to provide compounds of Formula V, as in step c. Compounds of Formula VIa where $R_2$ is H can be prepared by reduction of V, wherein X is bromo, under radical conditions with a hydride such as tributyltin hydride ($Bu_3SnH$) and an initiator such as azobisisobutyronitrile (AIBN) as in step d. Compounds of Formula VIa where $R_2$ is substituted phenyl can be prepared as in step e by treating compounds of Formula V, wherein X is halo, with a substituted arylhalide in the presence of zinc dust, a catalyst such as, for example tris(dibenzylideneacetone)dipalladium ($Pd_2(dba)_3$), and a ligand such as tri(ortho-tolyl)phosphine ($P(o-tolyl)_3$) in a solvent such as N,N-dimethylformamide (DMF).

Scheme 1

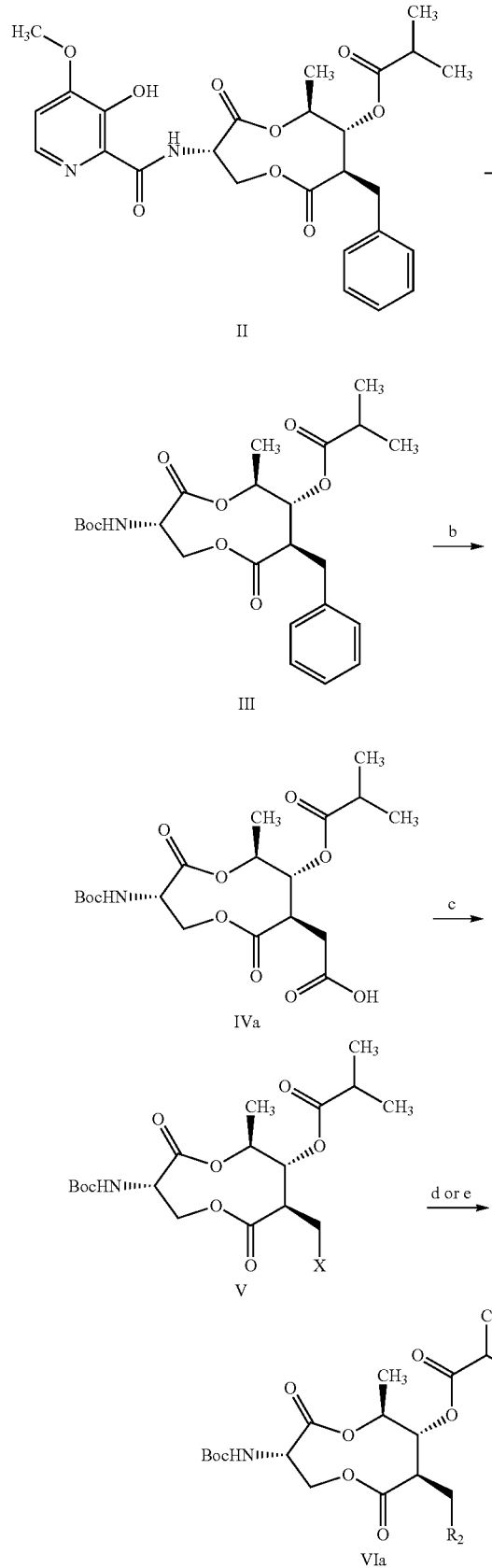

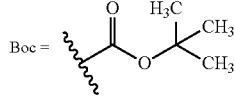

In Scheme 2, compounds of Formula Ib, where R₂ is as previously defined, can be prepared through removal of the amine protecting group under appropriate conditions. For example, a Boc group can be removed via treatment with a strong acid, such as a solution of hydrogen chloride (HCl) in dioxane or trifluoroacetic acid (TFA) in a solvent such as dichloromethane (DCM, CH₂Cl₂). Subsequent formation of the amide bond is achieved via treatment with a picolinic acid, such as 3-hydroxy-4-methoxy-picolinic acid, in the presence of a peptide coupling reagent, such as (dimethylamino)-N,N-dimethyl(3H-[1,2,3]triazolo[4,5-b]pyridin-3-yloxy)methaniminium hexafluorophosphate (HATU) in a solvent such as CH₂Cl₂.

Scheme 2

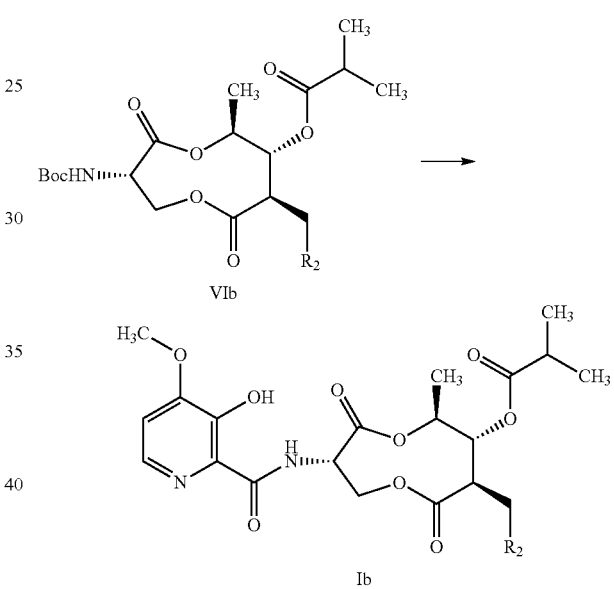

In Scheme 3, compounds of Formula Ic, where R₂ is as previously defined can be prepared from compounds of Formula Ib by reaction with the appropriate alkyl halide in the presence of a reagent such as sodium iodide (NaI) and a base such as sodium carbonate (Na₂CO₃) in a solvent such as acetone or an acyl halide in the presence of an amine base, such as pyridine or triethylamine, in an aprotic solvent such as DCM.

Scheme 3

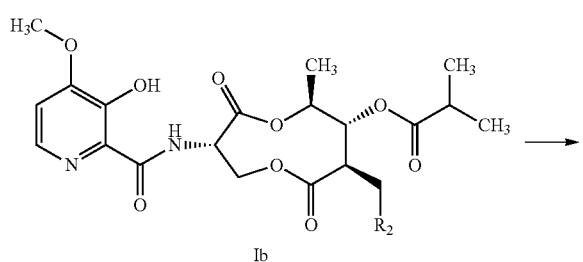

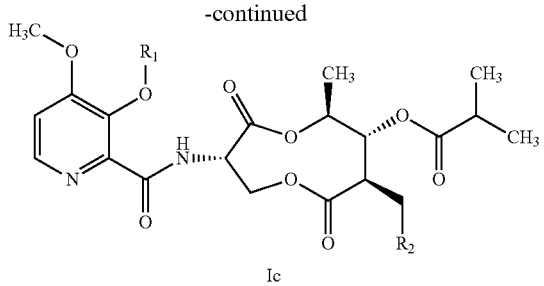

Ic

In Scheme 4, compound VII can be made as in step a from compound VIc by reaction with a reducing agent such as borane ($BH_3$) in a polar, aprotic solvent such as tetrahydrofuran (THF). Compounds of Formula VIII, wherein $R_4$ is as previously defined, can be prepared from compound VII, as shown in step b, by reaction with $R_4C(O)X$ wherein X is a halogen, in the presence of a base, such as pyridine, and in a solvent such as $CH_2Cl_2$. Compounds of Formula IXa, where $R_4$ is alkyl, phenyl, or substituted phenyl can be prepared from compound VII, as shown in step c, by reaction with a substituted sulfonyl halide in the presence of an organic base, such as pyridine, in a solvent such as $CH_2Cl_2$. Compound X can be prepared from compound VII as shown in step d. Subjection of VII to oxidative conditions, for example, treatment with Dess-Martin periodinane affords the aldehyde, which is then treated with a fluorinating agent such as Deoxo-Fluor™ in an aprotic solvent system such as toluene and $CH_2Cl_2$ to give difluoro-substituted compound X. Compounds of Formula XI, wherein $R_4$ is arylalkyl, can be synthesized from compound VII by reaction with an aryl-alkylating agent, such as 2-benzyloxy-1-methylpyridinium triflate, in the presence of a reagent such as magnesium oxide (MgO) in a solvent such as α,α,α-trifluorotoluene, as in step e. Compounds of Formula XII, wherein $R_4$ is alkyl, can be prepared from compound VII, as shown in step f, by alkylating with a reagent such as trimethyloxonium tetrafluoroborate in the presence of a drying reagent such as sodium sulfate ($Na_2SO_4$) and a base, such as, for example, N,N,N',N'-tetramethylnaphthalene-1,8-diamine (Proton Sponge™) in an anhydrous, aprotic solvent such as $CH_2Cl_2$. Compounds of Formula XIII, wherein $R_4$ is as previously defined, can be synthesized from compounds of Formula VIc, as shown in step g, by treatment with an alcohol such as tert-butanol (t-BuOH), in the presence of a coupling reagent such as N,N'-methanediylidenedipropan-2-amine (N,N-diisopropylcarbodiimide, DIC) in the presence of a base such as 4-dimethylaminopyridine (DMAP) in a solvent such as $CH_2Cl_2$.

Scheme 4

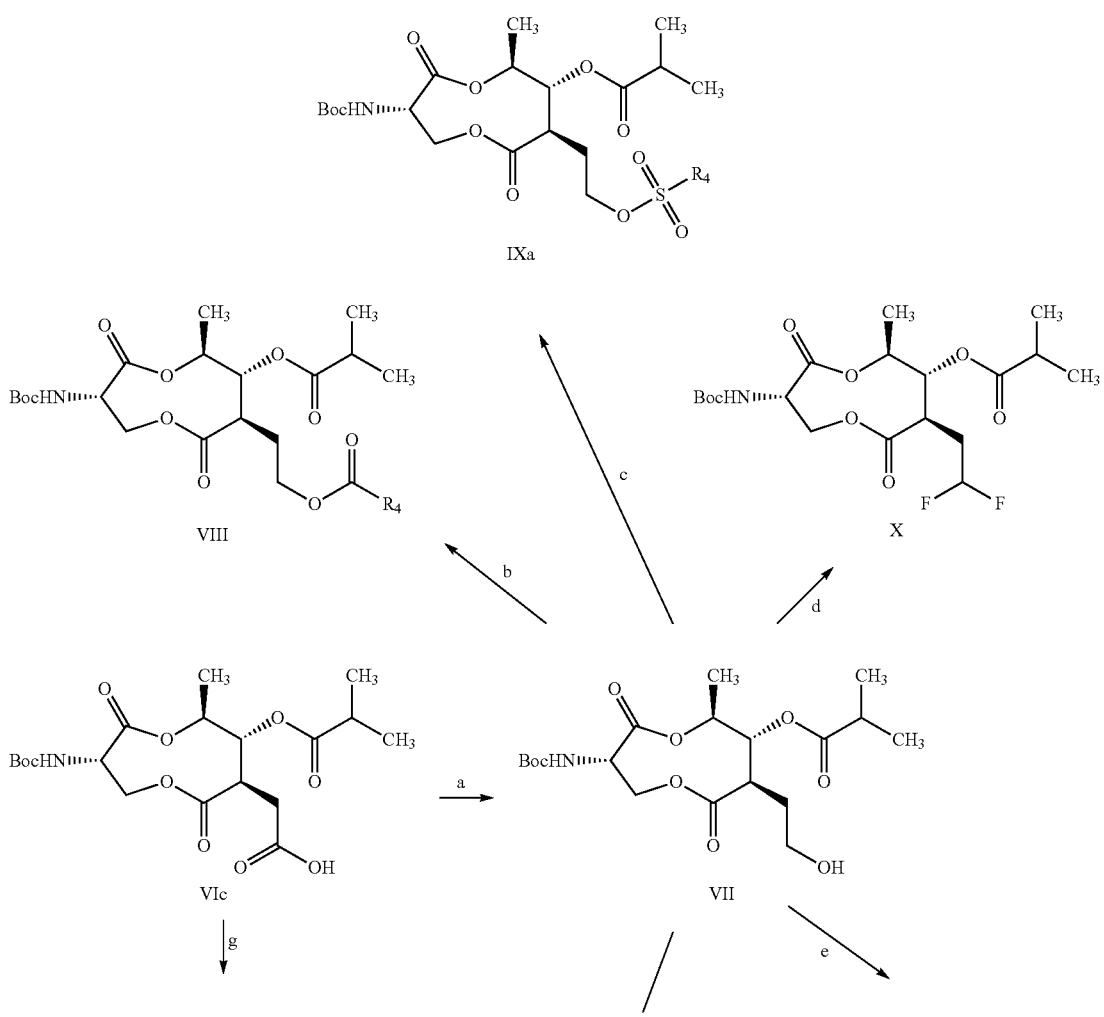

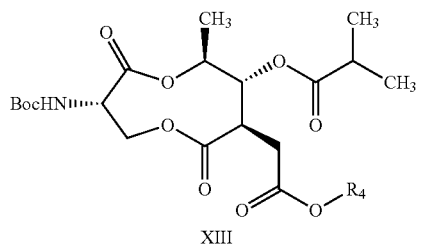

XIII

-continued

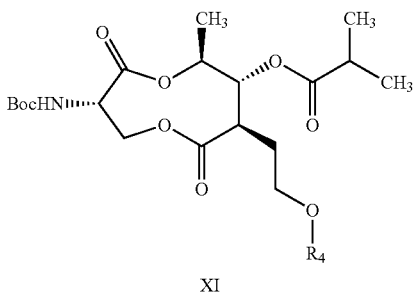

XI

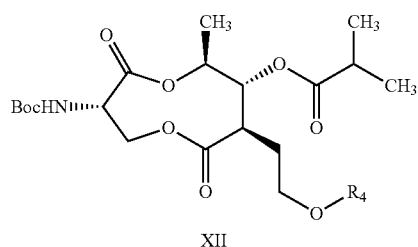

XII

Compounds of Formula XIV, wherein $R_5$ is as previously defined, can be prepared as shown in Scheme 5, step a. Treating compounds of Formula IXb, wherein $R_4$ is as previously defined, with a nucleophile such as sodium azide ($NaN_3$) in a solvent such as DMF affords an intermediate azide that can be reacted with an alkyne such as 1-chloro-3-ethynylbenzene in the presence of a copper salt, such as copper sulfate ($CuSO_4$) and sodium ascorbate in a solvent system such as DMF and $H_2O$ to give compounds of Formula XIV. Compound XV can be prepared from compounds of Formula IXb, as shown in step b, by reaction with NaI in a solvent such as DMF. Compounds of Formula XVI, wherein $R_4$ is aryl, can be prepared from compound XV, as illustrated in step c, by reaction with zinc (Zn) in the presence of iodine ($I_2$) to form an intermediate organozinc species. Reaction of the organozinc intermediate with an aryl halide in the presence of a palladium catalyst such as dichlorobis[tris(o-tolyl)phospine]palladium(II) ($PdCl_2[P(o-Tol)_3]_2$) in a solvent such as DMF affords compounds of Formula XVI. Compound XVII can be prepared, as depicted in step d, from compound XV by reaction with a hydride source such as $Bu_3SnH$, in the presence of an initiator such as AIBN and an aromatic solvent such as benzene. Compound XVIII can be prepared from compounds of Formula IXb by treatment with NaI in DMF at an elevated temperature for 48 hours (h), as shown in step e.

Scheme 5

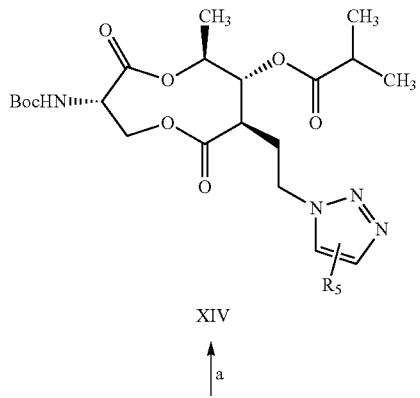

XIV

↑ a

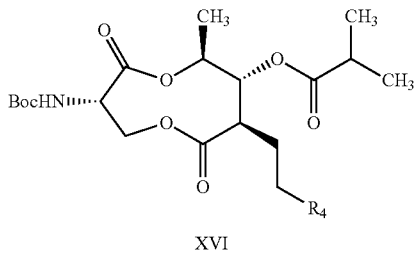

XVI

↑ c

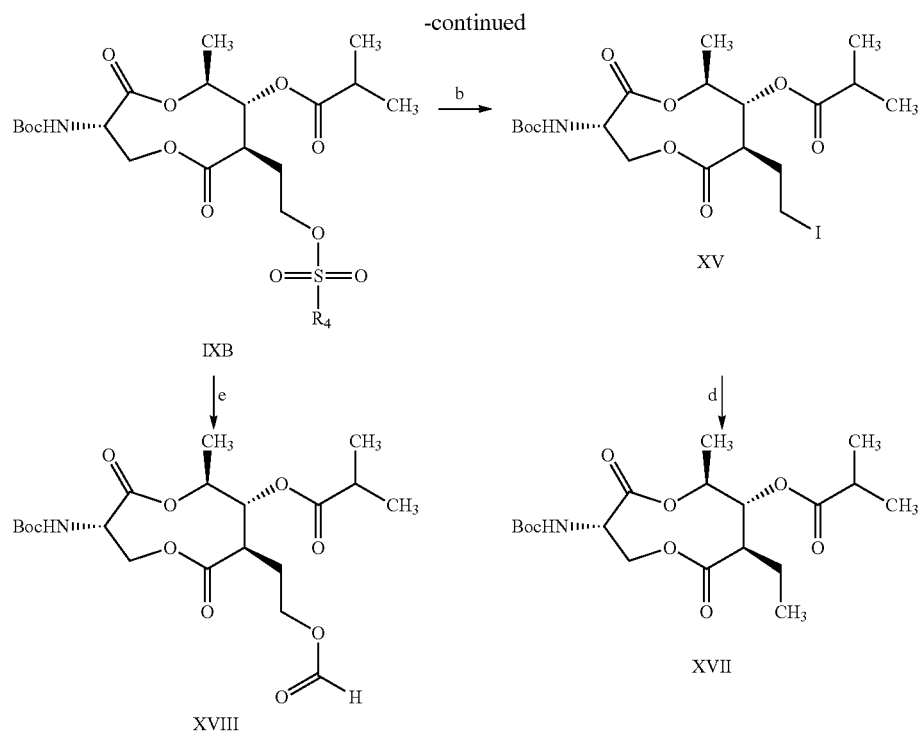

In Scheme 6, compounds of Formula XIX can be prepared from compounds of Formula IIIb by treating with hydrogen gas (H₂) under high pressures, such as 500 pounds per square inch (psi), at elevated temperatures, such as 60° C., and in the presence of a catalyst such as 5% rhodium on carbon (Rh/C).

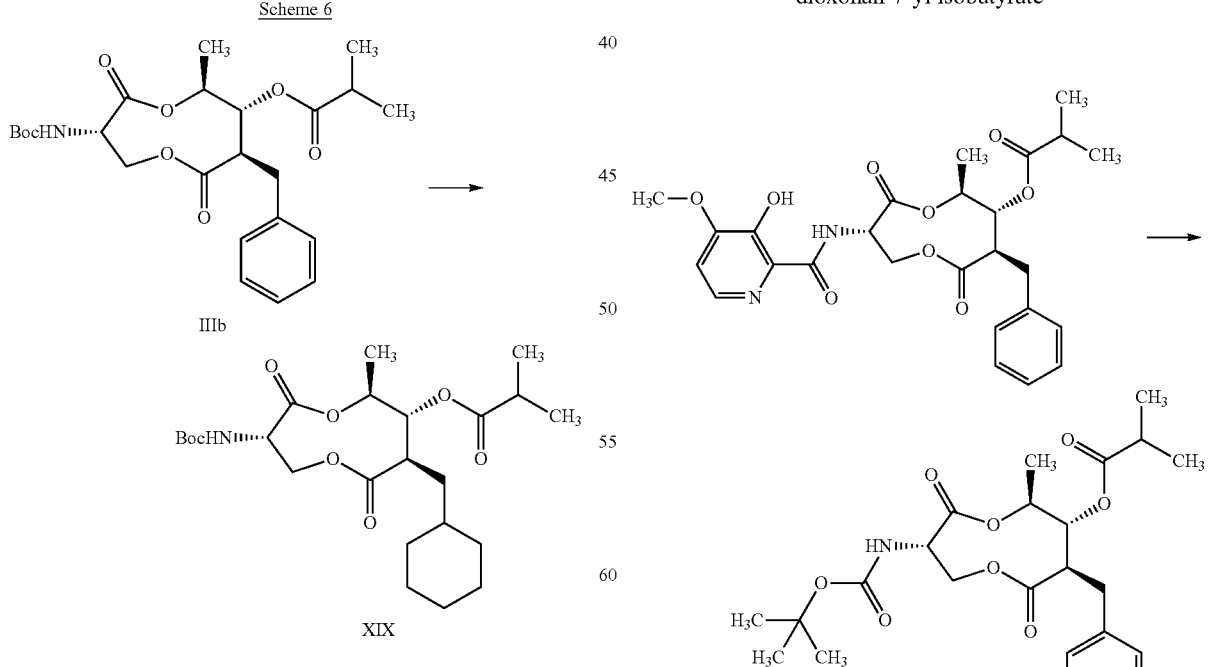

The following examples are presented to illustrate the various aspects of the compounds of the present disclosure and should not be construed as limitations to the claims.

EXAMPLES

Example 1

Step 1: Preparation of (3S,6S,7R,8R)-8-benzyl-3-(tert-butoxycarbonylamino)-6-methyl-4,9-dioxo-1,5-dioxonan-7-yl isobutyrate To a suspension of (3S,6S,7R,8R)-8-benzyl-3-(3-hydroxy-4-methoxypicolinamido)-6-methyl-4,9-dioxo-1,5-dioxonan-7-yl isobutyrate (UK-2A; 10.0 grams (g), 19.4 millimole (mmol)) and DMAP (237 milligrams (mg), 1.9 mmol) in CH$_3$CN (49 milliliters (mL)) was added di-tert-butyl dicarbonate (8.70 g, 39.8 mmol), and the mixture was stirred for 30 minutes (min). To the resulting clear solution was slowly added N,N-diethylethylenediamine and stirring was continued at room temperature (about 22° C.) for 90 min. The CH$_3$CN was removed in vacuo and the resulting residue was dissolved in ethyl ether (Et$_2$O; 200 mL) and washed with 1N (Normal) aqueous (aq) HCl (100 mL). The phases were separated and the aqueous phase was extracted further with Et$_2$O (25 mL). The organic extracts were combined, washed successively with 0.5N aq HCl and saturated (sat'd) aq sodium bicarbonate (NaHCO$_3$), dried over magnesium sulfate (MgSO$_4$), filtered, and concentrated to give a white glassy solid. Purification of the crude extract by column chromatography (Silica gel (SiO$_2$); 0→3% EtOAc/CH$_2$Cl$_2$) gave the title compound (2.41 g, 27%) as a white solid: mp 143-145° C.; IR (neat) 1768, 1740, 1693, 1515 cm$^{-1}$; $^1$H NMR (400 MHz, CDCl$_3$) δ 7.27-7.10 (m, 5H), 5.19 (m, 2H), 5.18 (dd, J=11.9, 7.6 Hz, 1H), 4.91 (td, J=12.2, 6.0 Hz, 1H), 4.79 (s, 1H), 3.43 (s, 1H), 3.00-2.86 (m, 2H), 2.68-2.58 (m, 2H), 1.43 (s, 9H), 1.30 (d, J=6.3 Hz, 3H), 1.23 (d, J=7.0, Hz, 3H), 1.23 (d, J=7.0, Hz, 3H); $^{13}$C NMR (400 MHz, CDCl$_3$): 175.6, 171.7, 170.8, 154.7, 137.9, 128.7, 128.5, 126.6, 80.5, 75.0, 74.4, 65.9, 51.9, 51.4, 34.5, 34.1, 28.2, 18.9, 17.8; ESIMS m/z 462.5 ([M−H]$^-$).

Example 1

Step 2: Preparation of 2-((3S,7R,8R,9S)-3-(tert-butoxycarbonylamino)-8-(isobutyryloxy)-9-methyl-2,6-dioxo-1,5-dioxonan-7-yl)acetic acid

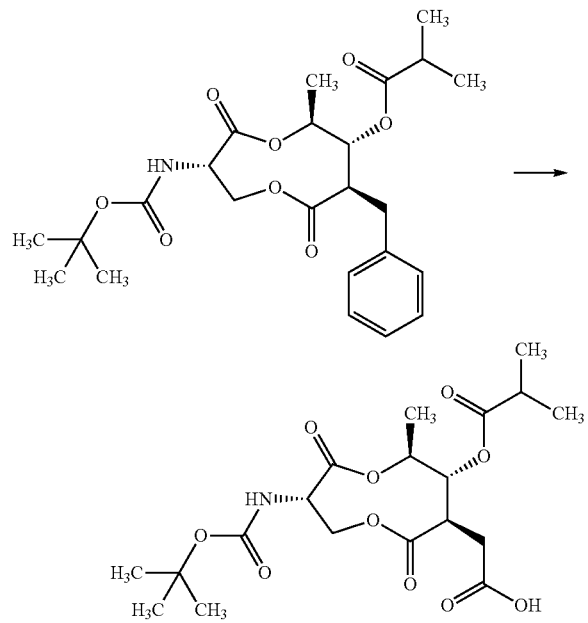

To a solution of (3S,6S,7R,8R)-8-benzyl-3-(tert-butoxycarbonylamino)-6-methyl-4,9-dioxo-1,5-dioxonan-7-yl isobutyrate (10 g, 21.6 mmol) in CH$_3$CN (72 mL), EtOAc (72 mL), and H$_2$O (575 mL) were added NaIO$_4$ (134 g, 626 mmol) and RuCl$_3$-trihydrate (282 mg, 1.08 mmol). The reaction was stirred at room temperature (about 22° C.) overnight. The resulting white suspension was diluted with water (700 mL) and extracted with CH$_2$Cl$_2$ (5×), and EtOAc (2×). Activated carbon (12 g) was added to the combined organic extracts (~2 L) and the mixture was stirred vigorously for 1 h. The mixture was filtered through Celite®, and the filtrate was dried over MgSO$_4$, filtered, and concentrated to give the title compound (7.71 g, 83%) as a gray solid: mp 164-167° C.; IR (neat) 3375, 3293 (br), 1773, 1743, 1731, 1686, 1157 cm$^{-1}$; $^1$H NMR (300 MHz, CDCl$_3$) δ 5.30 (m, 2H), 5.04 (t, J=9.7 Hz, 1H), 4.90 (m, 2H), 3.65 (s, 1H), 2.97 (m, 2H), 2.62 (m, 1H), 2.41 (m, 1H), 1.45 (s, 9H), 1.29 (d, J=6.2 Hz, 3H), 1.22 (d, J=7.0 Hz, 6H); $^{13}$C NMR (101 MHz, CDCl$_3$) δ 175.78, 175.61, 171.53, 171.03, 154.88, 80.85, 74.44, 74.05, 65.56, 51.16, 45.40, 34.03, 33.44, 28.24, 18.94, 18.83, 17.77; ESIMS m/z 430.4 ([M−H]$^-$).

Example 1

Step 3: Preparation of (3S,6S,7R,8R)-3-(tert-butoxycarbonylamino)-8-(iodomethyl)-6-methyl-4,9-dioxo-1,5-dioxonan-7-yl isobutyrate

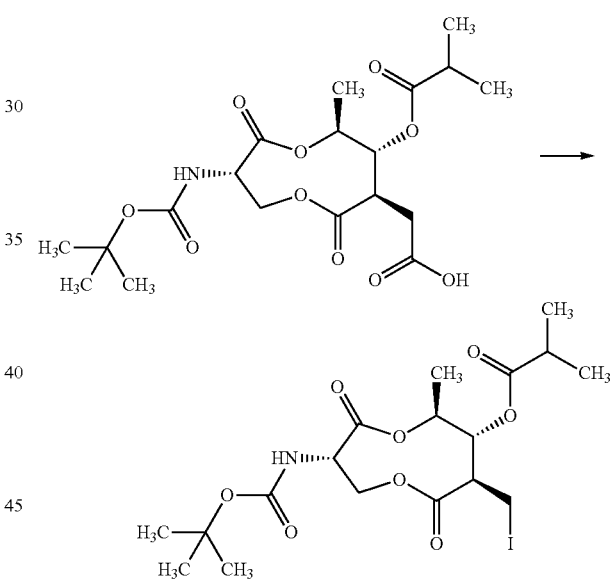

To a solution of 2-((3S,7R,8R,9S)-3-(tert-butoxycarbonylamino)-8-(isobutyryloxy)-9-methyl-2,6-dioxo-1,5-dioxonan-7-yl)acetic acid (9.90 g, 23 mmol) in THF (100 mL) was added N-methylmorpholine (2.5 mL, 23 mmol) followed by isobutylchloroformate (3.0 mL, 23 mmol) at 0° C. After stirring for 10 min, a solution of 2-mercaptopyridine N-oxide (3.5 g, 27.5 mmol) and triethylamine (TEA; 3.8 mL, 27.5 mmol) in THF (50 mL) was added slowly and the reaction stirred at 0° C. for 1.5 h in the dark (wrapped flask in aluminum foil). The precipitated N-methylmorpholine-HCl salt was removed by vacuum filtration and the filtrate was removed in vacuo at ambient temperature (about 22° C.). The oily residue was dissolved in CH$_2$Cl$_2$ (250 mL) and treated with Iodoform (11.8 g, 30 mmol). The solution was transferred to a UV reactor and irradiated with a 450 W mercury lamp with water cooling. After 1 h, the orange solution was removed from the reactor, adsorbed to Celite® and partially purified via flash chromatography (SiO$_2$, 20% EtOAc/DCM).

Additional flash chormatography (SiO₂, 10% EtOAc/DCM) followed by recrystallization from EtOAc/hexanes afforded the title compound (5.99 g, 51%) as an off-white solid: mp 168-171° C.; IR (neat) 3386, 2977, 1771, 1760, 1742, 1689, 1510 cm⁻¹; ¹H NMR (400 MHz, CDCl₃) δ 5.36 (s, 1H), 5.21 (m, 1H), 5.00 (t, J=9.7 Hz, 1H), 4.86 (m, 2H), 3.68 (brs, 1H), 3.31 (dd, J=11.5, 9.3 Hz, 1H), 3.02 (m, 2H), 2.63 (m, 1H), 1.45 (s, 9H), 1.27 (d, J=6.3 Hz, 3H), 1.22 (d, J=7.0 Hz, 6H); ESIMS m/z 536.3 ([M+Na]⁺).

Example 1

Step 4: Preparation of (3S,6S,7R,8R)-3-(tert-butoxycarbonylamino)-8-(4-fluorobenzyl)-6-methyl-4,9-dioxo-1,5-dioxonan-7-yl isobutyrate

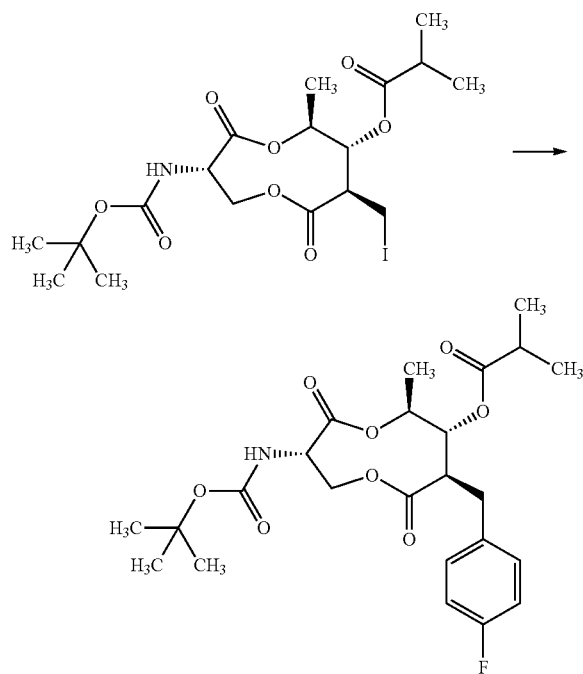

To a suspension of freshly ground zinc dust (139 mg, 2.13 mmol) in an oven-dried flask containing a stir bar were added DMF (200 µL; just covered the dust) and iodine (54 mg, 0.21 mmol), and the mixture was stirred for 1 min. To the mixture was added a solution of (3S,6S,7R,8R)-3-(tert-butoxycarbonylamino)-8-(iodomethyl)-6-methyl-4,9-dioxo-1,5-dioxonan-7-yl isobutyrate (273 mg, 0.53 mmol) in DMF (1 mL) slowly at 40° C. After 15 min, the reaction mixture was cooled to ambient temperature (about 22° C.) and a solution of Pd₂(dba)₃ (12 mg, 0.01 mmol), (o-tol)₃P (16 mg, 0.05 mmol), and 1-fluoro-4-iodobenzene (80 µL, 0.69 mmol) in DMF (900 µL) was added to the reaction and the reaction was warmed back to 40° C. and stirring continued for 1.5 hr. The mixture was cooled, diluted with EtOAc (2 mL), and filtered through a 0.45 micrometer (µm) fritted filter disc. The solution was diluted with EtOAc (100 mL), washed with H₂O (3×), dried over MgSO₄, filtered, and concentrated. Purification by column chromatography (SiO₂, 0→20% EtOAc/hexanes) gave the title compound (96 mg, 38%) as a white, glassy solid: mp 58-66° C.; ¹H NMR (300 MHz, CDCl₃) δ 7.08 (m, 2H), 6.95 (m, 2H), 5.22-5.14 (m, 3H), 4.93 (m, 1H), 4.80 (m, 1H), 3.46 (m, 1H), 3.00-2.80 (m, 2H), 2.64 (m, 2H), 1.44 (s, 9H), 1.31 (d, J=6.4 Hz, 3H), 1.25 (d, J=7.0 Hz, 3H), 1.25 (d, J=7.0 Hz, 3H); ESIMS m/z 503.3 ([M+Na]⁺).

Example 1

Step 5: Preparation of (3S,6S,7R,8R)-8-(4-fluorobenzyl)-3-(3-hydroxy-4-methoxypicolinamido)-6-methyl-4,9-dioxo-1,5-dioxonan-7-yl isobutyrate (Compound 1)

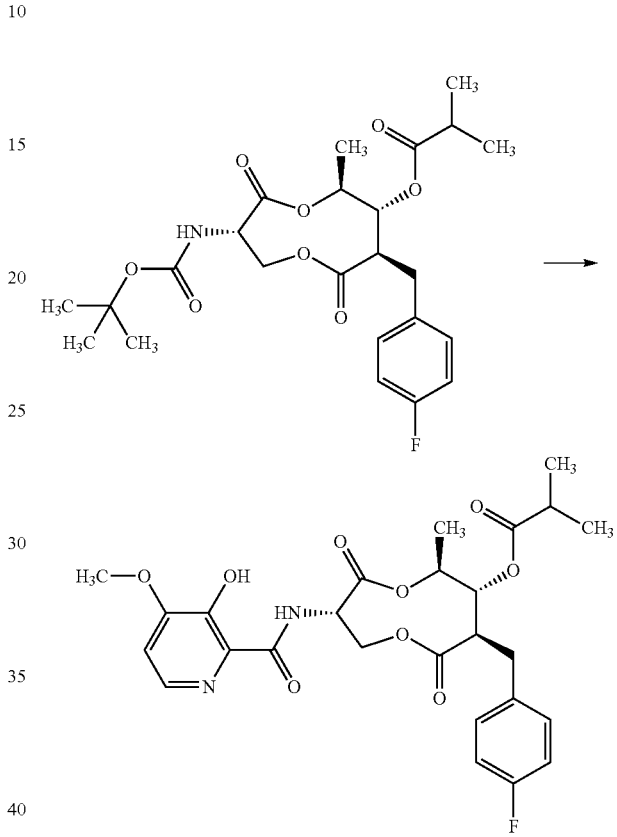

Method A: To a solution of (3S,6S,7R,8R)-3-(tert-butoxycarbonylamino)-8-(4-fluorobenzyl)-6-methyl-4,9-dioxo-1,5-dioxonan-7-yl isobutyrate (90 mg, 0.19 mmol) in CH₂Cl₂ (2 mL) was added TFA (1 mL) and the reaction was stirred for 1.5 hr and then concentrated. The residue was dissolved in CH₂Cl₂ (75 mL) and the solution was washed with sat'd aqueous NaHCO₃, dried over MgSO₄, filtered, and concentrated to dryness. The residue was dissolved in CH₂Cl₂ (1.8 mL), and the solution was sequentially treated with 3-hydroxy-4-methoxypicolinic acid (41 mg, 0.24 mmol), N-methylmorpholine (123 µL, 1.12 mmol), HATU (107 mg, 0.28 mmol) and a catalytic amount of DMAP. The reaction was stirred at ambient temperature (about 22° C.) for 3 h and then loaded directly onto a 12 g SiO₂ column for purification by flash chromatography (0→20% EtOAc/CH₂Cl₂ followed by 80% EtOAc/CH₂Cl₂) to give the title compound (66 mg, 66%) as a white solid.

Method B: (3S,6S,7R,8R)-3-(tert-butoxycarbonylamino)-8-(4-fluorobenzyl)-6-methyl-4,9-dioxo-1,5-dioxonan-7-yl isobutyrate (83 mg, 0.17 mmol) was treated with 4N HCl in dioxane (2 mL), and the reaction was stirred at ambient temperature (about 22° C.) overnight. The reaction was concentrated in vacuo, and the residue was dissolved in CH₂Cl₂ (1.8 mL). To this solution were added 3-hydroxy-4-methoxypicolinic acid (38 mg, 0.22 mmol), N-methylmorpholine (114

μL, 1.03 mmol), HATU (98 mg, 0.26 mmol) and a catalytic amount of DMAP sequentially. The reaction was stirred at ambient temperature for about 3 h and the resulting clear solution was loaded directly onto a SiO$_2$ column for purification by flash chromatography (0→20% EtOAc/CH$_2$Cl$_2$ followed by 80% EtOAc/CH$_2$Cl$_2$) to give the title compound (18 mg, 20%) as a white solid: mp 208-210° C.; IR (neat)=3359, 1746, 1652, 1531 cm$^{-1}$; $^1$H NMR (400 MHz, CDCl$_3$) δ 11.77 (s, 1H), 8.59 (d, J=8.2 Hz, 1H), 7.99 (d, J=5.2 Hz, 1H), 7.11-7.07 (m, 2H), 6.95 (t, J=8.7 Hz, 2H), 6.88 (d, J=5.2 Hz, 1H), 5.32 (dd, J=33.3, 24.1 Hz, 2H), 5.20-5.09 (m, 2H), 4.97 (m, 1H), 3.94 (s, 3H), 3.62 (brs, 1H), 3.09-2.80 (m, 2H), 2.80-2.54 (m, 2H), 1.32 (d, J=6.3 Hz, 3H), 1.25 (d, J=7.0 Hz, 3H), 1.24 (d, J=7.0 Hz, 3H); $^{13}$C NMR (101 MHz, CDCl$_3$) δ 175.61, 171.63, 169.72, 168.98, 162.94, 160.50, 155.44, 148.84, 140.74, 133.47, 130.35, 130.27, 129.92, 115.58, 115.37, 109.73, 74.94, 74.72, 65.28, 56.14, 52.15, 49.94, 34.13, 33.78, 18.99, 17.85; ESIMS m/z 532.9 ([M+H]$^+$).

Compounds 2-10, 11 (Step 4 omitted), and 12-18 were made as described in Example 1.

Example 2

Preparation of 2-((3S,7R,8R,9S)-8-(isobutyryloxy)-3-(3-(isobutyryloxymethoxy)-4-methoxypicolinamido)-9-methyl-2,6-dioxo-1,5-dioxonan-7-yl)ethyl benzoate (Compound 19)

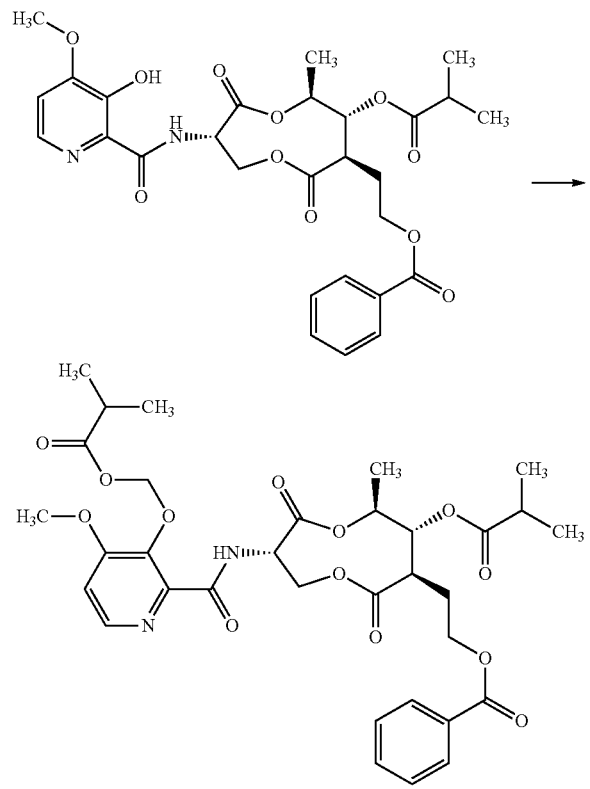

To a mixture of 2-((3S,7R,8R,9S)-3-(3-hydroxy-4-methoxypicolinamido)-8-(isobutyryloxy)-9-methyl-2,6-dioxo-1,5-dioxonan-7-yl)ethyl benzoate (50 mg, 0.087 mmol), Na$_2$CO$_3$ (15 mg, 0.14 mmol) and NaI (3.09 mg, 0.021 mmol) in acetone (0.6 mL) was added chloromethyl isobutyrate (15.4 mg, 0.114 mmol) slowly at room temperature (about 22° C.). The resulting reaction mixture was warmed to 50° C. and stirred at 50° C. overnight. The solvent was evaporated and the crude residue was purified via flash chromatography (SiO$_2$, hexanes/EtOAc gradient) to afford the title compound (35 mg, 76%) as an off-white solid: mp 48-50° C.; $^1$H NMR (300 MHz, CDCl$_3$) δ 8.55 (d, J=7.9 Hz, 1H), 8.26 (d, J=5.5 Hz, 1H), 8.04-7.87 (m, 2H), 7.55 (t, J=7.4 Hz, 1H), 7.43 (t, J=7.5 Hz, 2H), 6.95 (d, J=5.4 Hz, 1H), 5.85-5.62 (m, 2H), 5.41 (s, 1H), 5.26-5.06 (m, 2H), 4.94 (dd, J=9.8, 6.3 Hz, 1H), 4.42-4.19 (m, 2H), 3.92 (d, J=14.3 Hz, 3H), 3.65 (s, 1H), 2.76 (t, J=9.5 Hz, 1H), 2.62 (dt, J=10.8, 5.5 Hz, 1H), 2.58-2.47 (m, 1H), 2.30 (s, 1H), 1.82 (s, 1H), 1.29 (d, J=6.3 Hz, 3H), 1.21 (dd, J=7.0, 0.9 Hz, 6H), 1.13 (d, J=7.0 Hz, 6H); ESIMS m/z 673 ([M+H]$^+$).

Compounds 20-34 were made as described in Example 2.

Example 3

Step 1: Preparation of (3S,6S,7R,8R)-3-(tert-butoxycarbonylamino)-8-(2-hydroxyethyl)-6-methyl-4,9-dioxo-1,5-dioxonan-7-yl isobutyrate

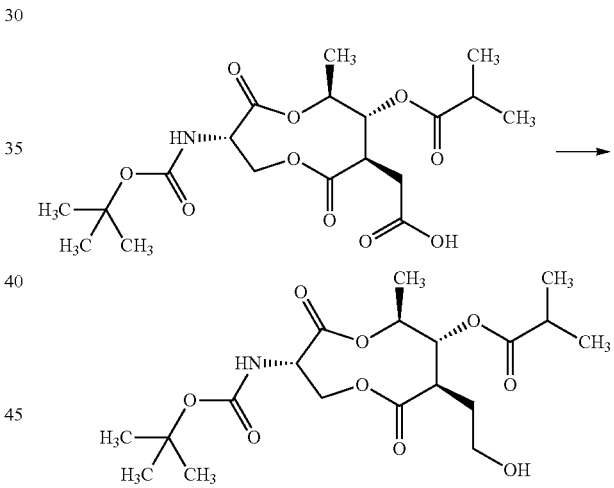

To a solution of 2-((3S,7R,8R,9S)-3-(tert-butoxycarbonylamino)-8-(isobutyryloxy)-9-methyl-2,6-dioxo-1,5-dioxonan-7-yl)acetic acid (2.0 g, 4.64 mmol) in THF (15 mL) was added borane (1.0 M in THF, 5.56 mL, 5.56 mmol) at 0° C. After 15 min the ice bath was removed and the reaction was allowed to warm to room temperature (about 22° C.). After an additional 1.5 h, the reaction was quenched with EtOAc (10 mL) and washed successively with 0.5 N HCl (10 mL) and sat'd aqueous NaHCO$_3$ (10 mL). The phases were separated and the organic phase was dried over MgSO$_4$, filtered, and concentrated in vacuo to give the title compound (1.38 g, 72%) as a white solid: $^1$H NMR (300 MHz, CDCl$_3$) δ 5.40-5.19 (m, 2H), 5.07 (t, J=9.9 Hz, 1H), 4.95-4.75 (m, 2H), 3.74-3.52 (m, 3H), 2.83-2.68 (m, 1H), 2.61 (dt, J=13.9, 7.0 Hz, 1H), 2.07-1.90 (m, 1H), 1.70-1.52 (m, 1H), 1.44 (s, 9H), 1.27 (d, J=6.3 Hz, 3H), 1.20 (d, J=7.0 Hz, 6H); ESIMS m/z 440.3 ([M+Na]$^+$).

Example 3

Step 2: Preparation of 2-((3S,7R,8R,9S)-3-(tert-butoxycarbonylamino)-8-(isobutyryloxy)-9-methyl-2,6-dioxo-1,5-dioxonan-7-yl)ethyl benzoate

Example 3

Step 3: Preparation of 2-((3S,7R,8R,9S)-3-(3-hydroxy-4-methoxypicolinamido)-8-(isobutyryloxy)-9-methyl-2,6-dioxo-1,5-dioxonan-7-yl)ethyl benzoate (Compound 35)

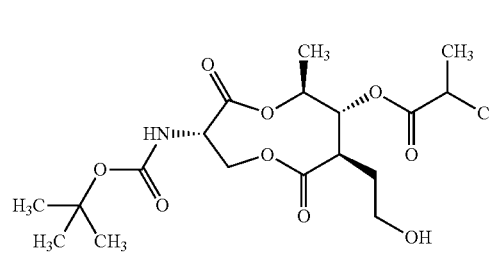

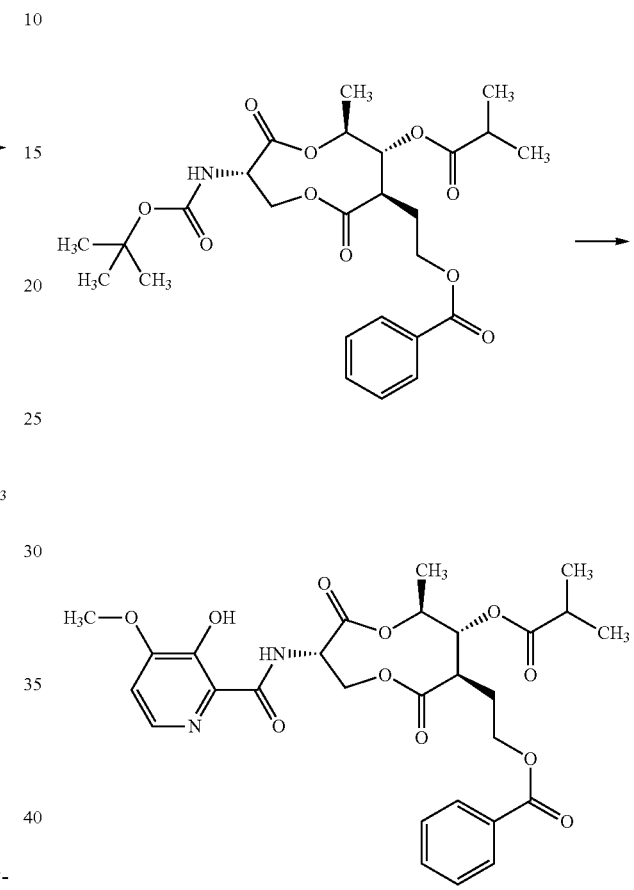

To a solution of (3S,6S,7R,8R)-3-(tert-butoxycarbonylamino)-8-(2-hydroxyethyl)-6 methyl-4,9-dioxo-1,5-dioxonan-7-yl isobutyrate (200 mg, 0.479 mmol) in pyridine (0.5 mL) and $CH_2Cl_2$ (1 mL) was added benzoyl chloride (195 mg, 0.958 mmol) at room temperature (about 22° C.), and the reaction mixture was stirred at room temperature for 12 h. The solvents were removed under vacuum and the residue was purified by column chromatography ($SiO_2$, hexanes/EtOAc gradient) to give the title compound (268 mg, 74%) as a white solid: $^1$H NMR (300 MHz, $CDCl_3$) δ 7.97 (dd, J=8.5, 1.0 Hz, 2H), 7.56-7.40 (m, J=10.6, 3H), 5.39-5.15 (m, 2H), 5.10 (t, J=9.9 Hz, 1H), 4.97-4.73 (m, 2H), 4.42-4.29 (m, 1H), 4.25 (m, 1H), 3.57-3.35 (m, 1H), 2.73 (t, J=9.5 Hz, 1H), 2.62 (dt, J=14.0, 7.0 Hz, 1H), 2.36-2.18 (m, 1H), 1.90-1.71 (m, 1H), 1.46 (s, 9H), 1.28 (d, J=6.4 Hz, 3H), 1.21 (dd, J=7.0, 1.0 Hz, 6H); ESIMS m/z 544 ([M+Na]$^+$).

Compound 35 was prepared in the same manner as described in Example 1, Step 5, Method A to give the title compound (140 mg, 48%) as a white solid: mp 172-174° C.; $^1$H NMR (300 MHz, $CDCl_3$) δ 11.78 (d, J=0.5 Hz, 1H), 8.61 (d, J=8.2 Hz, 1H), 8.07-7.87 (m, 3H), 7.65-7.53 (m, 1H), 7.50-7.39 (m, 2H), 6.88 (d, J=5.1 Hz, 1H), 5.40 (s, 1H), 5.27-5.08 (m, 2H), 4.96 (dq, J=12.5, 6.3 Hz, 1H), 4.42-4.20 (m, 2H), 3.95 (s, 3H), 3.64 (s, 1H), 2.86-2.72 (m, 1H), 2.63 (dt, J=14.0, 7.0 Hz, 1H), 2.37-2.22 (m, 1H), 1.81 (s, 1H), 1.31 (d, J=6.3 Hz, 3H), 1.22 (dd, J=7.0, 1.2 Hz, 6H); ESIMS m/z 573 ([M+H]$^+$).

Compounds 36-43 were made as described in Example 3.

Example 4

Step 1: Preparation of (3S,6S,7R,8R)-3-(tert-butoxycarbonylamino)-8-(2-methoxyethyl)-6-methyl-4,9-dioxo-1,5-dioxonan-7-yl isobutyrate

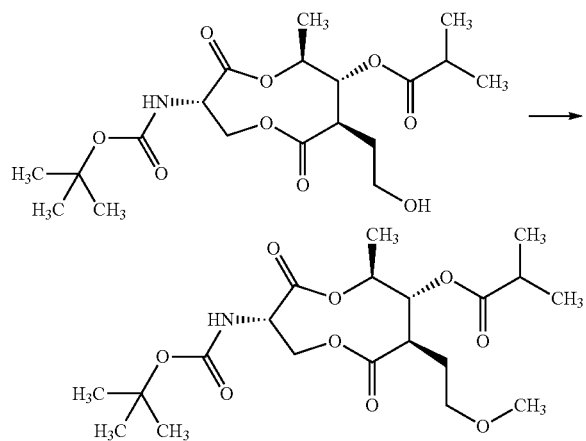

A round bottom flask was charged with (3S,6S,7R,8R)-3-(tert-butoxycarbonyl-amino)-8-(2-hydroxyethyl)-6-methyl-4,9-dioxo-1,5-dioxonan-7-yl isobutyrate (200 mg, 0.48 mmol), Proton Sponge™ (700 mg, 4.05 mmol), Na$_2$SO$_4$ in CH$_2$Cl$_2$ (10 mL) at 0° C. To the resulting suspension was added trimethyloxonium tetrafluoroborate (Me$_3$OBF$_4$, 320 mg, 2.16 mmol), and the suspension was warmed to room temperature (about 22° C.) and stirred for 5 h. The mixture was diluted with EtOAc, filtered, and the filtrate was washed successively with water and 1M NaHSO$_4$. The organics were dried over Na$_2$SO$_4$, filtered, and the filtrate was concentrated under reduced pressure. Purification of the crude product via column chromatography (hexanes/EtOAc gradient) afforded the title compound (140 mg, 71%) as a clear oil: $^1$H NMR (300 MHz, CDCl$_3$) δ 5.41-5.16 (m, J=0.9 Hz, 2H), 5.06 (t, J=9.9 Hz, 1H), 4.94-4.73 (m, 2H), 3.69-3.52 (m, 1H), 3.42-3.27 (m, 2H), 3.26 (s, J=0.9 Hz, 3H), 2.80-2.67 (m, 1H), 2.60 (dt, J=13.9, 7.0 Hz, 1H), 2.08-1.86 (m, 1H), 1.66-1.55 (m, 1H), 1.45 (s, 9H), 1.27 (d, J=6.3 Hz, 3H), 1.20 (d, J=7.0 Hz, 6H); ESIMS m/z 454 ([M+Na]$^+$).

Example 4

Step 2: Preparation of (3S,6S,7R,8R)-3-(3-hydroxy-4-methoxypicolinamido)-8-(2-methoxyethyl)-6-methyl-4,9-dioxo-1,5-dioxonan-7-yl isobutyrate (Compound 44)

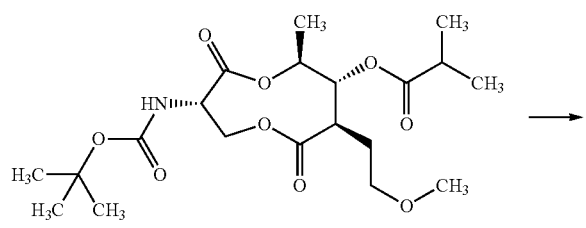

Compound 44 was prepared in the same manner as described in Example 1, Step 5, Method A to give the title compound (78 mg, 48%) as a white solid: mp 128-130° C.; $^1$H NMR (300 MHz, CDCl$_3$) δ 11.81 (s, 1H), 8.67 (d, J=8.3 Hz, 1H), 8.01 (dd, J=5.2, 0.5 Hz, 2H), 6.90 (d, J=5.2 Hz, 2H), 5.62-5.37 (m, 1H), 5.30-5.16 (m, J=14.9, 8.1 Hz, 2H), 5.09 (q, J=9.5 Hz, 2H), 5.02-4.89 (m, 2H), 3.95 (s, 3H), 3.81 (s, 1H), 3.45-3.29 (m, 2H), 3.27 (s, 2H), 2.85-2.72 (m, 1H), 2.62 (ddd, J=11.8, 8.1, 5.9 Hz, 1H), 2.08-1.92 (m, 2H), 1.84-1.57 (m, 2H), 1.30 (d, J=6.2 Hz, 3H), 1.22 (d, J=7.0 Hz, 6H); ESIMS m/z 439 ([M+H]$^+$).

Compound 45 was made as described in Example 4.

Example 5

Step 1: Preparation of (3S,6S,7R,8R)-3-(tert-butoxycarbonylamino)-6,8-dimethyl-4,9-dioxo-1,5-dioxonan-7-yl isobutyrate

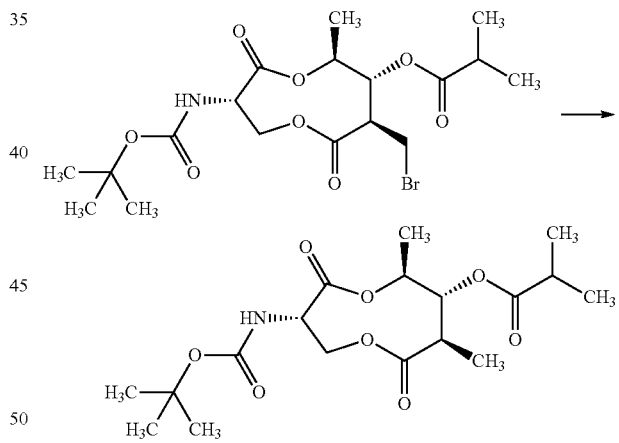

To a solution of (3S,6S,7R,8R)-8-(bromomethyl)-3-(tert-butoxycarbonylamino)-6-methyl-4,9-dioxo-1,5-dioxonan-7-yl isobutyrate (238 mg, 0.51 mmol) in benzene (3 mL) was added Bu$_3$SnH (178 mg, 0.61 mmol) and AIBN (2 mg) at room temperature (about 22° C.). The reaction solution was heated to reflux, stirred for 1 hr, and the solution was cooled to room temperature. The solvent was removed under vacuum and the residue was purified via column chromatography (SiO$_2$, hexanes/EtOAc gradient) to afford the title compound (185 mg, 94%) as a white solid: $^1$H NMR (300 MHz, CDCl$_3$) δ 5.40-5.12 (m, 2H), 5.00 (t, J=9.8 Hz, 1H), 4.93-4.71 (m, 2H), 3.69-3.47 (m, 1H), 2.69-2.50 (m, 2H), 1.45 (s, J=4.7 Hz, 9H), 1.28 (d, J=6.3 Hz, 3H), 1.21 (dd, J=7.0, 1.2 Hz, 6H), 1.13 (d, J=6.7 Hz, 3H); ESIMS m/z 410 ([M+Na]$^+$).

Example 5

Step 2: Preparation of (3S,6S,7R,8R)-3-(3-hydroxy-4-methoxypicolinamido)-6,8-dimethyl-4,9-dioxo-1,5-dioxonan-7-yl isobutyrate (Compound 46)

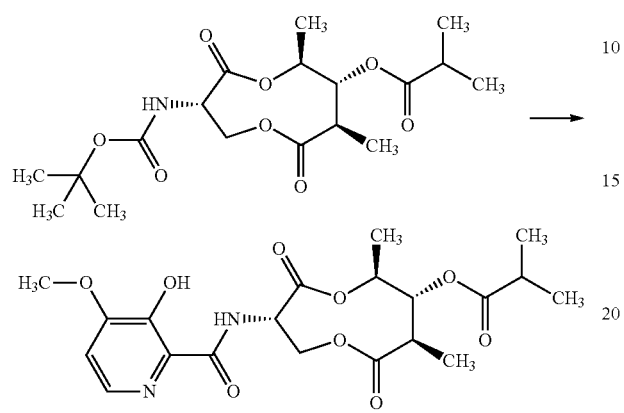

Compound 46 was prepared in the same manner as described in Example 1, Step 5, Method A to give the title compound (74 mg, 37%) as a white solid: mp 198-200° C.; $^1$H NMR (300 MHz, CDCl$_3$) δ 11.80 (s, 1H), 8.65 (d, J=7.9 Hz, 1H), 8.01 (d, J=5.2 Hz, 1H), 6.89 (d, J=5.2 Hz, 1H), 5.54-5.31 (m, 1H), 5.19 (dd, J=15.3, 8.1 Hz, 1H), 5.04 (t, J=9.7 Hz, 1H), 4.94 (td, J=12.2, 6.1 Hz, 1H), 3.95 (s, 3H), 3.78 (s, 1H), 2.65 (ddt, J=20.9, 13.8, 6.8 Hz, 2H), 1.30 (d, J=6.1 Hz, 3H), 1.22 (d, J=7.0 Hz, 6H), 1.16 (d, J=6.7 Hz, 3H); ESIMS m/z 439 ([M+H]$^+$).

Example 6

Step 1: Preparation of (3S,6S,7R,8R)-8-(2-tert-butoxy-2-oxoethyl)-3-(tert-butoxycarbonylamino)-6-methyl-4,9-dioxo-1,5-dioxonan-7-yl isobutyrate

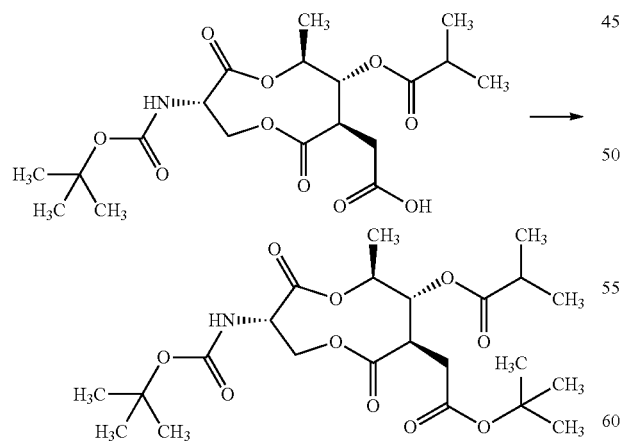

To a solution of 2-((3S,7R,8R,9S)-3-(tert-butoxycarbonylamino)-8-(isobutyryloxy)-9-methyl-2,6-dioxo-1,5-dioxonan-7-yl)acetic acid (400 mg, 0.928 mmol) in CH$_2$Cl$_2$ (2 mL) was added tert-butyl alcohol (3.44 mg, 4.64 mmol) and DMAP (91 mg, 0.744 mmol) at room temperature (about 22° C.). The solution was cooled to 0° C. and N,N'-methanediylidenedipropan-2-amine (172 uL, 1.11 mmol) was added. The reaction mixture was warmed to room temperature, stirred for 2 h, and then loaded directly onto a SiO$_2$ column and purified by flash chromatography (hexanes/EtOAc gradient) to give the title compound (380 mg, 84%) as a white solid: mp 170-172° C.; $^1$H NMR (400 MHz, CDCl$_3$) δ 5.44-5.15 (m, 2H), 5.08-4.94 (m, 1H), 4.93-4.75 (m, 2H), 3.74-3.54 (m, 1H), 2.98-2.87 (m, 1H), 2.83-2.71 (m, 1H), 2.61 (hept, J=7.0 Hz, 1H), 2.32-2.21 (m, 1H), 1.44 (s, 9H), 1.40 (s, 9H), 1.27 (d, J=6.3 Hz, 3H), 1.21 (dd, J=7.0, 1.6 Hz, 6H); ESIMS m/z 410 ([M+Na]$^+$).

Example 6

Step 2: Preparation of (3S,6S,7R,8R)-8-(2-tert-butoxy-2-oxoethyl)-3-(3-hydroxy-4-methoxypicolinamido)-6-methyl-4,9-dioxo-1,5-dioxonan-7-yl isobutyrate (Compound 47)

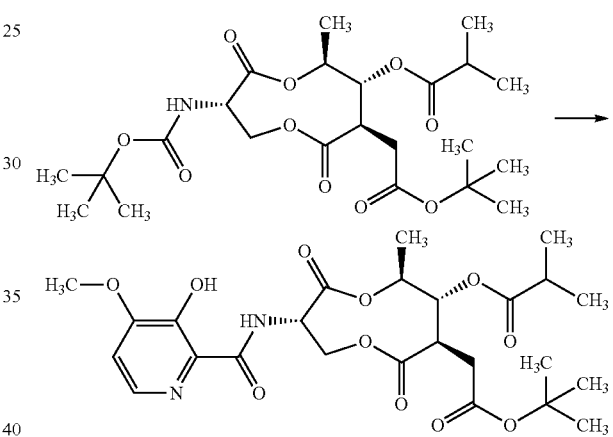

To a solution of (3S,6S,7R,8R)-8-(2-tert-butoxy-2-oxoethyl)-3-(tert-butoxycarbonylamino)-6-methyl-4,9-dioxo-1,5-dioxonan-7-yl isobutyrate (130 mg, 0.267 mmol) in EtOAc (3 mL) was added 1M HCl in EtOAc and the solution was stirred at room temperature (about 22° C.) for 6 h. The solvent was evaporated and the residue was dissolved in CH$_2$Cl$_2$ (1.5 mL). To this solution was added 3-hydroxy-4-methoxypicolinic acid (58 mg, 0.345 mmol), HATU (139 mg, 0.367 mmol) and N-methylmorpholine (120 mL, 1.09 mmol), sequentially. The reaction was allowed to stir at ambient temperature for 12 h and then loaded directly onto a SiO$_2$ column and purified by flash chromatography (hexanes/EtOAc gradient) to give the title compound (62 mg, 43%) as a white solid: mp 192-194° C.; $^1$H NMR (400 MHz, CDCl$_3$) δ 11.79 (d, J=0.5 Hz, 1H), 8.63 (d, J=8.3 Hz, 1H), 8.01 (d, J=5.2 Hz, 1H), 6.89 (d, J=5.1 Hz, 1H), 5.45 (s, 1H), 5.21 (dd, J=15.5, 8.3 Hz, 1H), 5.12-5.01 (m, 1H), 5.01-4.87 (m, 1H), 3.95 (s, 3H), 3.80 (d, J=25.0 Hz, 1H), 2.98 (ddd, J=11.8, 9.9, 3.2 Hz, 1H), 2.86-2.74 (m, 1H), 2.62 (dt, J=14.0, 7.0 Hz, 1H), 2.35-2.23 (m, 1H), 1.41 (s, 9H), 1.30 (dd, J=6.2, 2.4 Hz, 3H), 1.22 (dd, J=7.0, 1.6 Hz, 6H); $^{13}$C NMR (101 MHz, CDCl$_3$) δ 175.50, 172.00, 170.26, 169.90, 169.01, 155.45, 148.86, 140.73, 129.97, 109.74, 81.74, 74.79, 74.07, 65.03, 56.13, 49.80, 45.81, 34.93, 34.02, 27.97, 18.96, 18.84, 17.79; ESIMS m/z 539 ([M+H]$^+$).

Compounds 48-50 were made as described in Example 6.

Example 7

Step 1: Preparation of (3S,6S,7R,8R)-3-(tert-butoxycarbonylamino)-8-(2-(formyloxy)ethyl)-6-methyl-4,9-dioxo-1,5-dioxonan-7-yl isobutyrate

Step 2: Preparation of (3S,6S,7R,8R)-8-(2-(formyloxy)ethyl)-3-(3-hydroxy-4-methoxypicolinamido)-6-methyl-4,9-dioxo-1,5-dioxonan-7-yl isobutyrate (Compound 51)

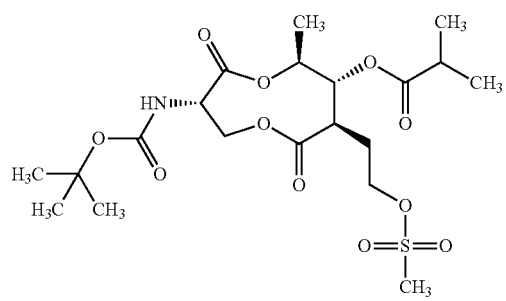

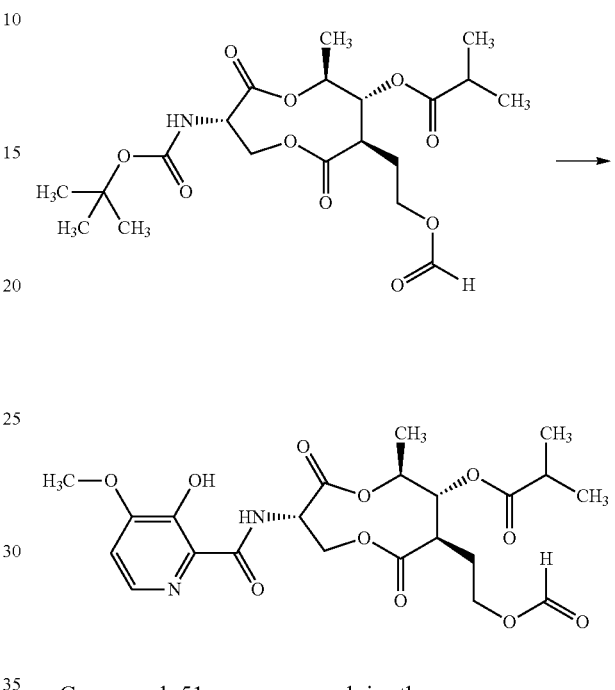

To a solution (3S,6S,7R,8R)-3-(tert-butoxycarbonylamino)-6-methyl-8-(2(methylsulfonyloxy)ethyl)-4,9-dioxo-1,5-dioxonan-7-yl isobutyrate (510 mg, 1.03 mmol) in DMF (3 mL) at room temperature (about 22° C.) was added NaI (1 g, 6.7 mmol). The resulting reaction mixture was heated to 80° C. and stirred for 48 h. After cooling to room temperature, saturated NaHCO$_3$ solution (30 mL) and EtOAc (25 mL) were added. The phases were separated and the aqueous phase was extracted with EtOAc (2×25 mL). The combined EtOAc extracts were dried over Na$_2$SO$_4$, filtered, and concentrated to dryness. The crude residue was purified via column chromatography (SiO$_2$, hexanes/EtOAc gradient) to afford the title compound (228 mg, 50%) as a white solid (228 mg, 50%): mp 103-104; $^1$H NMR (400 MHz, CDCl$_3$) δ 8.00 (s, 1H), 5.43-5.15 (m, 2H), 5.06 (t, J=9.9 Hz, 1H), 4.93-4.77 (m, 2H), 4.19 (dt, J=11.1, 5.5 Hz, 1H), 4.05 (ddd, J=11.4, 8.9, 4.8 Hz, 1H), 3.60 (s, 1H), 2.71 (td, J=11.4, 2.8 Hz, 1H), 2.67-2.53 (m, 1H), 2.17-2.02 (m, 1H), 1.73 (dt, J=14.7, 7.4 Hz, 1H), 1.45 (s, J=15.6 Hz, 9H), 1.28 (d, J=6.3 Hz, 3H), 1.21 (dd, J=7.0, 0.5 Hz, 6H); ESIMS m/z 468 ([M+Na]$^+$).

Compound 51 was prepared in the same manner as described in Example 1, Step 5, Method A to give a white solid (106 mg, 51%): mp 103-105° C.; $^1$H NMR (300 MHz, CDCl$_3$) δ 11.78 (s, 1H), 8.64 (d, J=7.9 Hz, 1H), 8.09-7.92 (m, 2H), 6.90 (d, J=5.3 Hz, 1H), 5.47 (s, 1H), 5.21 (d, J=7.0 Hz, 1H), 5.11 (t, J=9.9 Hz, 1H), 5.01-4.88 (m, 1H), 4.21 (dt, J=11.0, 5.4 Hz, 1H), 4.14-4.00 (m, 1H), 3.95 (s, 3H), 3.79 (s, 1H), 2.84-2.69 (m, 1H), 2.63 (dt, J=14.0, 7.0 Hz, 1H), 2.20-2.06 (m, 1H), 1.78 (s, 1H), 1.31 (d, J=6.2 Hz, 3H), 1.22 (d, J=7.0 Hz, 6H); ESIMS m/z 498 ([M+H]$^+$).

Example 8

Step 1: Preparation of (3S,6S,7R,8R)-3-(tert-butoxycarbonylamino)-6-methyl-4,9-dioxo-8-(2-oxoethyl)-1,5-dioxonan-7-yl isobutyrate

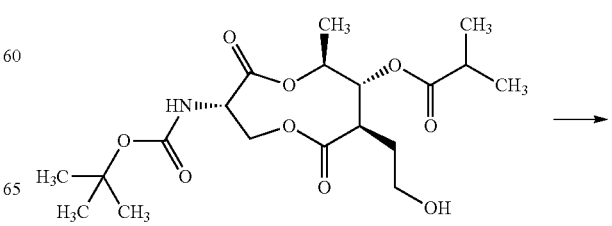

35

-continued

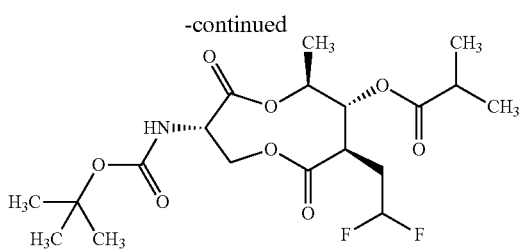

To a solution of (3S,6S,7R,8R)-3-(tert-butoxycarbonylamino)-8-(2-hydroxyethyl)-6-methyl-4,9-dioxo-1,5-dioxonan-7-yl isobutyrate (200 mg, 0.48 mmol) in CH$_2$Cl$_2$ at 0° C. was added Dess-Martin reagent (264 mg, 0.62 mmol). The resulting reaction mixture was stirred at 0° C. for 3 h and then at room temperature (about 22° C.) for another 1 h. The mixture was partitioned between sat'd aqueous NaHCO$_3$ solution (20 mL) and EtOAc (25 mL), and the phases were separated. The aqueous phase was extracted with additional EtOAc (2×25 mL), and the combined EtOAc extracts were dried over Na$_2$SO$_4$, filtered, and the filtrate was concentrated to dryness. The crude residue was purified via column chromatography (SiO$_2$, hexanes/EtOAc gradient) to yield the intermediate aldehyde (78 mg, 38%) as a colorless oil. A portion of the oil (50 mg) was dissolved in a mixture of toluene (1 mL) and CH$_2$Cl$_2$ (0.2 mL) and cooled to 0° C. To the resulting solution was added Deoxo-Fluor™ (115 mg, 50% solution in toluene, 0.26 mg) at 0° C. The reaction solution was stirred at 0° C. for 2 h and then at room temperature for 1 h. The solvent was removed and the residue was purified via column chromatography (SiO$_2$, hexanes/EtOAc gradient) to afford the title compound (27 mg, 51%) as a white solid: $^1$H NMR (300 MHz, CDCl$_3$) δ 5.80 (tdd, J=56.1, 4.8, 3.1 Hz, 1H), 5.39-5.12 (m, 2H), 5.05 (t, J=9.8 Hz, 1H), 4.89 (ddd, J=12.5, 9.8, 6.3 Hz, 2H), 3.62 (s, 1H), 2.92-2.74 (m, 1H), 2.62 (dt, J=14.0, 7.0 Hz, 1H), 2.50-2.32 (m, 1H), 1.89-1.70 (m, 1H), 1.45 (s, 9H), 1.29 (d, J=6.2 Hz, 3H), 1.21 (dd, J=7.0, 0.5 Hz, 6H); ESIMS m/z 460 ([M+Na]$^+$).

Example 8

Step 2: Preparation of (3S,6S,7R,8R)-8-(2,2-difluoroethyl)-3-(3-hydroxy-4-methoxypicolinamido)-6-methyl-4,9-dioxo-1,5-dioxonan-7-yl isobutyrate (Compound 52)

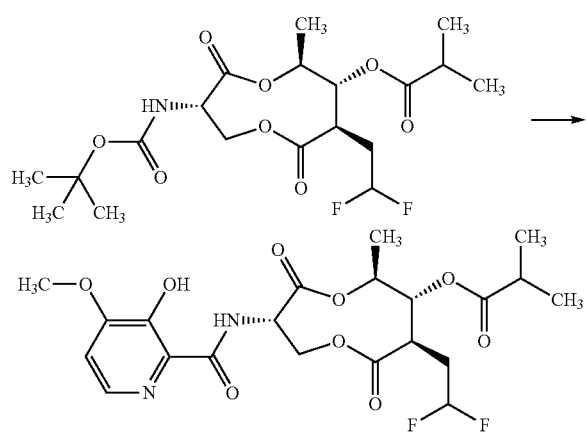

36

Compound 52 was prepared in the same manner as described in Example 1, Step 5, Method A to afford the title compound (38 mg, 48%) as a white solid: mp 195-196° C.; $^1$H NMR (300 MHz, CDCl$_3$) δ 11.76 (s, 1H), 8.64 (d, J=8.1 Hz, 1H), 8.01 (d, J=5.2 Hz, 1H), 6.89 (d, J=5.2 Hz, 1H), 6.06-5.60 (m, 1H), 5.45 (s, 1H), 5.22 (dd, J=15.5, 8.1 Hz, 1H), 5.09 (t, J=9.8 Hz, 1H), 5.03-4.90 (m, 1H), 3.95 (s, 3H), 3.81 (s, 1H), 2.94-2.80 (m, 1H), 2.64 (dt, J=14.0, 7.0 Hz, 1H), 2.58-2.33 (m, 1H), 1.92-1.72 (m, 1H), 1.32 (d, J=6.2 Hz, 3H), 1.23 (dd, J=9.6, 2.8 Hz, 6H); ESIMS m/z 489 ([M+H]$^+$).

Example 9

Step 1: Preparation of (3S,6S,7R,8R)-3-(tert-butoxycarbonylamino)-6-methyl-8-(2-(methylsulfonyloxy)ethyl)-4,9-dioxo-1,5-dioxonan-7-yl isobutyrate

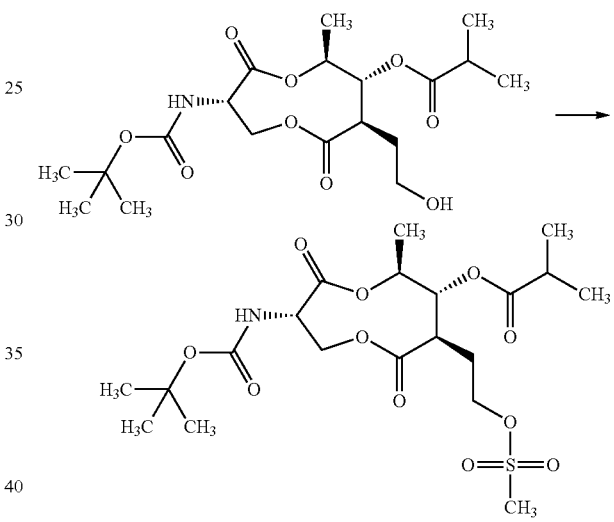

To a solution of (3S,6S,7R,8R)-3-(tert-butoxycarbonylamino)-8-(2-hydroxyethyl)-6-methyl-4,9-dioxo-1,5-dioxonan-7-yl isobutyrate (660 mg, 1.58 mmol) in CH$_2$Cl$_2$ (15 mL) at 0° C. was added pyridine (750 mg, 9.48 mmol), followed by methanesulfonyl chloride (362 mg, 3.16 mmol). The resulting reaction mixture was warmed up to room temperature (about 22° C.) and stirred overnight. The reaction mixture was partitioned between sat'd aqueous NaHCO$_3$ solution (30 mL) and EtOAc (40 mL) and the phases were separated. The aqueous phase was extracted with additional EtOAc (2×30 mL) and the combined EtOAc extracts were dried over Na$_2$SO$_4$, filtered, and concentrated to dryness. The crude residue was purified via column chromatography (SiO$_2$, hexanes/EtOAc gradient) to afford the title compound (660 mg, 84%) as a white solid: $^1$H NMR (300 MHz, CDCl$_3$) δ 5.24 (s, 2H), 5.06 (t, J=9.8 Hz, 1H), 4.95-4.77 (m, 2H), 4.32-4.19 (m, 1H), 4.13-4.05 (m, 1H), 3.62 (s, 1H), 2.98 (s, 3H), 2.78 (dd, J=14.9, 6.4 Hz, 1H), 2.62 (dt, J=13.9, 7.0 Hz, 1H), 2.25-2.08 (m, 1H), 1.83 (s, 1H), 1.47 (d, J=11.9 Hz, 9H), 1.28 (d, J=6.3 Hz, 3H), 1.21 (d, J=6.9 Hz, 6H); ESIMS m/z 496 ([M+H]$^+$).

Example 9

Step 2: Preparation of (3S,6S,7R,8R)-3-(tert-butoxycarbonylamino)-8-(2-iodoethyl)-6-methyl-4,9-dioxo-1,5-dioxonan-7-yl isobutyrate

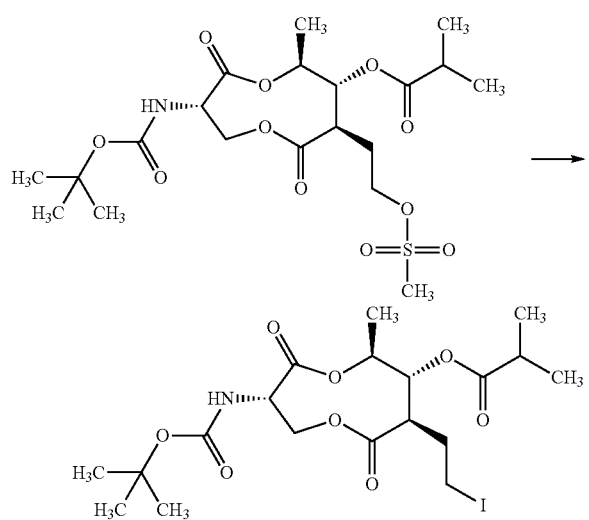

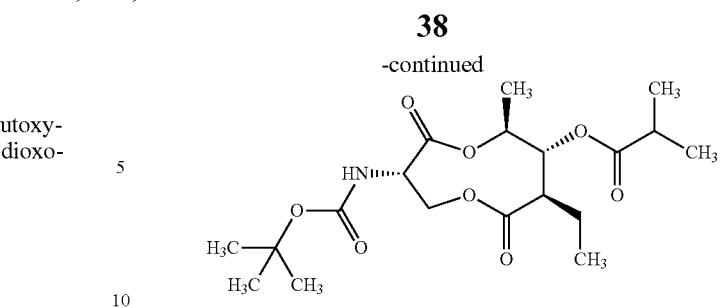

To a solution of (3S,6S,7R,8R)-3-(tert-butoxycarbonylamino)-6-methyl-8-(2(methylsulfonyloxy)ethyl)-4,9-dioxo-1,5-dioxonan-7-yl isobutyrate (350 mg, 0.71 mmol) in DMF (3 mL) at room temperature (about 22° C.) was added NaI (1.06 g, 7.06 mmol), and the resulting reaction mixture was heated to 60° C. and stirred for 6 h. The reaction mixture was partitioned between sat'd aqueous NaHCO₃ solution (20 mL) and EtOAc (25 mL) and the phases were separated. The aqueous phase was extracted with EtOAc (2×25 mL) and the combined EtOAc extracts were dried over Na₂SO₄, filtered, and concentrated to dryness. The crude residue was purified via column chromatography (SiO₂, hexanes/EtOAc gradient) to afford the title compound (300 mg, 81%) as a white solid: $^1$H NMR (400 MHz, CDCl₃) δ 5.43-5.15 (m, 2H), 5.07 (t, J=9.8 Hz, 1H), 4.95-4.75 (m, 2H), 3.72-3.51 (m, 1H), 3.24 (ddd, J=10.6, 6.6, 4.3 Hz, 1H), 3.00-2.87 (m, 1H), 2.82 (td, J=10.9, 3.0 Hz, 1H), 2.62 (hept, J=7.0 Hz, 1H), 2.35-2.21 (m, 1H), 1.86-1.69 (m, 1H), 1.45 (s, 9H), 1.28 (d, J=6.3 Hz, 3H), 1.22 (dd, J=7.0, 3.9 Hz, 6H); ESIMS m/z 550 ([M+Na]⁺).

Example 9

Step 3: (3S,6S,7R,8R)-3-(tert-butoxycarbonylamino)-8-ethyl-6-methyl-4,9-dioxo-1,5-dioxonan-7-yl isobutyrate

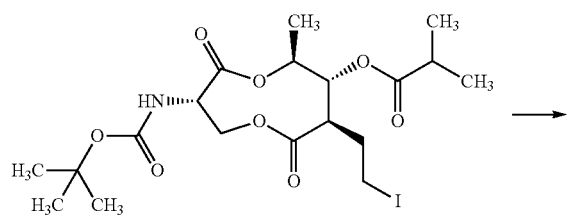

To a solution of (3S,6S,7R,8R)-3-(tert-butoxycarbonylamino)-8-(2-iodoethyl)-6-methyl-4,9-dioxo-1,5-dioxonan-7-yl isobutyrate (30 mg, 0.057 mmol) in benzene (1.5 mL) was added Bu₃SnH (27 mg, 0.091 mmol) and AIBN (1 mg) at room temperature (about 22° C.), and the reaction solution was heated to reflux. After 1 h, the solution was cooled to room temperature. The solvent was removed under vacuum and the residue was purified via column chromatography (SiO₂, hexanes/EtOAc gradient) to afford the title compound (20 mg, 88%) as a white solid: $^1$H NMR (300 MHz, CDCl₃) δ 5.44-5.19 (m, 2H), 5.03 (dd, J=13.0, 6.9 Hz, 1H), 4.91-4.73 (m, 2H), 3.70-3.52 (m, 1H), 2.68-2.52 (m, 1H), 2.45 (ddd, J=19.2, 12.0, 6.2 Hz, 1H), 1.71-1.56 (m, 2H), 1.45 (s, J=9.2 Hz, 9H), 1.26 (d, J=6.2 Hz, 3H), 1.20 (d, J=7.0 Hz, 6H), 0.86 (t, J=7.4 Hz, 3H); ESIMS m/z 424 ([M+Na]⁺).

Example 9

Step 4: Preparation of (3S,6S,7R,8R)-8-ethyl-3-(3-hydroxy-4-methoxypicolinamido)-6-methyl-4,9-dioxo-1,5-dioxonan-7-yl isobutyrate (Compound 53)

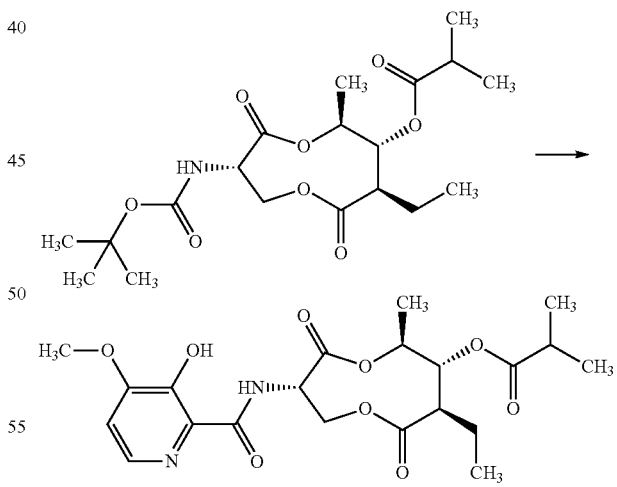

Compound 53 was prepared in the same manner as described in Example 1, Step 5, Method A to give the title compound (83 mg, 41%) as a white solid: mp 193-195° C.; $^1$H NMR (300 MHz, CDCl₃) δ 11.81 (s, 1H), 8.66 (d, J=8.1 Hz, 1H), 8.01 (d, J=5.2 Hz, 1H), 6.89 (d, J=5.2 Hz, 1H), 5.47 (s, 1H), 5.20 (dd, J=14.7, 8.1 Hz, 1H), 5.08 (t, J=9.9 Hz, 1H), 4.93 (dq, J=9.7, 6.3 Hz, 1H), 3.95 (s, 3H), 3.78 (m, 1H), 2.70-2.57 (m, 1H), 2.52 (ddd, J=11.5, 7.4, 2.5 Hz, 1H), 1.81-

1.63 (m, 2H), 1.53-1.34 (m, 2H), 1.29 (d, J=6.2 Hz, 3H), 1.21 (d, 6H), 0.88 (t, J=7.4 Hz, 3H); ESIMS m/z 453 ([M+H]⁺).

Example 10

Step 1: Preparation of (3S,6S,7R,8R)-3-(tert-butoxycarbonylamino)-8-(2-(4-(3-chlorophenyl)-1H-1,2,3-triazol-1-yl)ethyl)-6-methyl-4,9-dioxo-1,5-dioxonan-7-yl isobutyrate

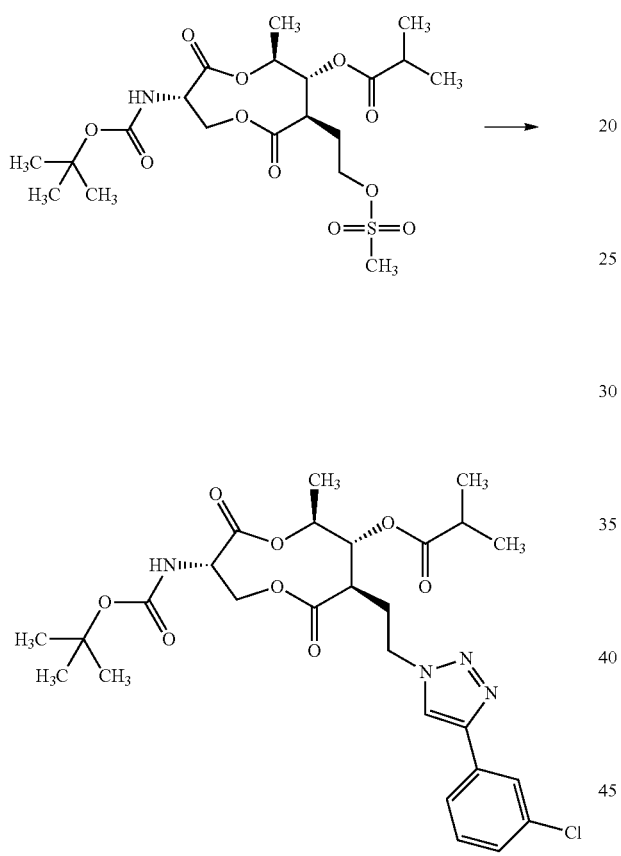

To a solution (3S,6S,7R,8R)-3-(tert-butoxycarbonylamino)-6-methyl-8-(2(methylsulfonyloxy)ethyl)-4,9-dioxo-1,5-dioxonan-7-yl isobutyrate (140 mg, 0.28 mmol) in DMF (3 mL) at room temperature (about 22° C.) was added NaN₃ (37 mg, 0.57 mmol). The resulting reaction mixture was heated to 60° C. and stirred for 3 h. The reaction was partitioned between sat'd aqueous NaHCO₃ solution (20 mL) and EtOAc (25 mL) and the phases were separated. The aqueous phase was extracted with additional EtOAc (2×25 mL), and the combined EtOAc extracts were dried over Na₂SO₄, filtered, and concentrated to dryness. The crude residue was dissolved in DMF/H₂O (1 mL/1 mL) and the resulting solution was treated with 1-chloro-3-ethynylbenzene (39 mg, 0.28 mol), CuSO₄ (4 mg, 0.025 mmol), and sodium ascorbate (22 mg, 0.11 mmol), and the reaction mixture was stirred at room temperature overnight. The reaction was partitioned between sat'd aqueous NaHCO₃ solution (15 mL) and EtOAc (20 mL) and the phases were separated. The aqueous phase was extracted with additional EtOAc (2×20 mL), and the combined EtOAc extracts were dried over Na₂SO₄, filtered, and concentrated to dryness. The crude residue was purified via column chromatography (SiO₂, hexanes/EtOAc gradient) to afford the title compound (105 mg, 64%) as a white solid: ¹H NMR (300 MHz, CDCl₃) δ 7.82 (d, J=1.7 Hz, 1H), 7.70 (dq, J=3.2, 1.5 Hz, 2H), 7.33 (ddd, J=10.9, 8.0, 4.9 Hz, 2H), 5.40-5.15 (m, 2H), 5.08 (t, J=9.8 Hz, 1H), 4.82 (dd, J=14.6, 4.8 Hz, 2H), 4.51-4.24 (m, 2H), 3.63 (s, 1H), 2.66-2.49 (m, 2H), 2.42-2.25 (m, 1H), 2.14-2.00 (m, 1H), 1.45 (s, 9H), 1.27 (dd, J=6.7, 1.3 Hz, 3H), 1.18 (d, J=7.1 Hz, 6H); ESIMS m/z 579 ([M+H]⁺).

Example 10

Step 2: Preparation of (3S,6S,7R,8R)-8-(2-(4-(3-chlorophenyl)-1H-1,2,3-triazol-1-yl)ethyl)-3-(3-hydroxy-4 methoxypicolinamido)-6-methyl-4,9-dioxo-1,5-dioxonan-7-yl isobutyrate (Compound 54)

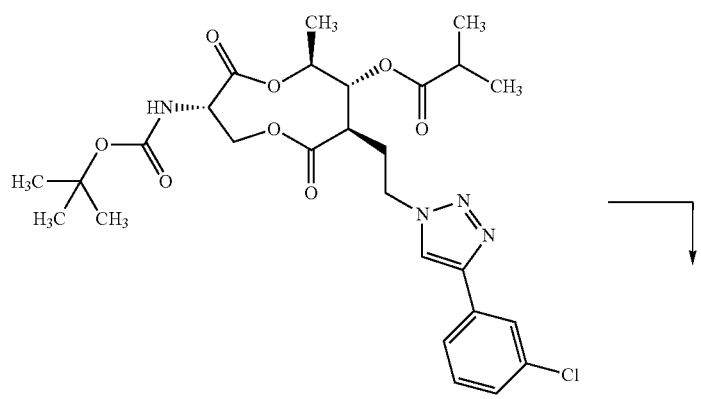

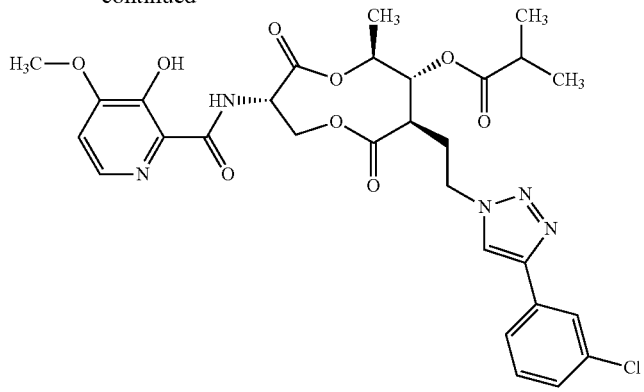

Compound 54 was prepared in the same manner as described in Example 1, Step 5, Method A to give the title compound (56 mg, 51%) as a white solid: mp 222-224° C.; $^1$H NMR (300 MHz, CDCl$_3$) δ 11.75 (s, 1H), 8.64 (d, J=8.1 Hz, 1H), 8.01 (d, J=5.2 Hz, 1H), 7.82 (s, 1H), 7.70 (d, J=7.6 Hz, 2H), 7.36 (dd, J=13.8, 6.4 Hz, 2H), 6.90 (d, J=5.2 Hz, 1H), 5.46 (s, 1H), 5.21 (d, J=8.1 Hz, 1H), 5.12 (t, J=9.7 Hz, 1H), 4.96-4.86 (m, 1H), 4.51-4.31 (m, 2H), 3.96 (s, 3H), 3.89-3.76 (m, 1H), 2.75-2.54 (m, 2H), 2.37 (s, 1H), 2.14 (s, 1H), 1.30 (d, J=6.2 Hz, 3H), 1.20 (d, J=7.0 Hz, 6H); ESIMS m/z 630 ([M+H]$^+$).

Compound 55 was made as described in Example 10.

Example 11

Preparation of (3S,6S,7R,8R)-3-(3-hydroxy-4-methoxypicolinamido)-6-methyl-8-(2(methylsulfonyloxy)ethyl)-4,9-dioxo-1,5-dioxonan-7-yl isobutyrate (Compound 56)

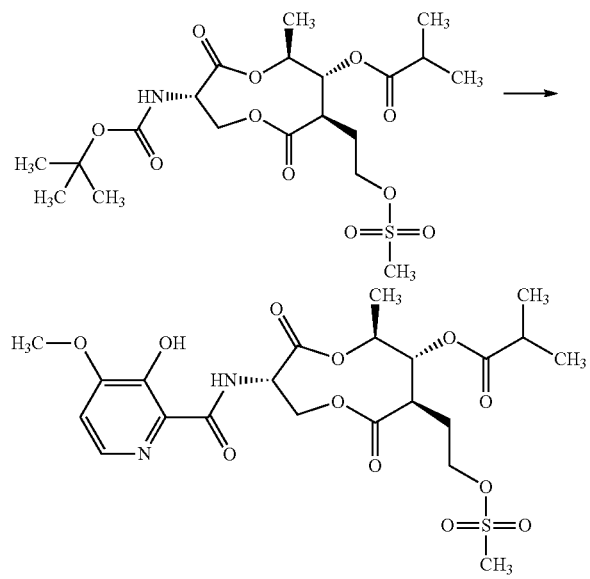

Compound 56 was prepared in the same manner as described in Example 1, Step 5, Method A to give of a white solid (56 mg, 51%): mp 153-155° C.; $^1$H NMR (400 MHz, CDCl$_3$) δ 11.76 (d, J=0.5 Hz, 1H), 8.65 (d, J=8.1 Hz, 1H), 8.02 (d, J=5.2 Hz, 1H), 6.90 (d, J=5.2 Hz, 1H), 5.47 (s, 1H), 5.20 (dd, J=15.2, 7.8 Hz, 1H), 5.16-5.05 (m, 1H), 4.96 (dq, J=9.8, 6.2 Hz, 1H), 4.28 (dt, J=10.5, 5.3 Hz, 1H), 4.20-4.07 (m, 1H), 3.95 (s, 3H), 3.78 (d, J=12.1 Hz, 1H), 2.98 (d, J=1.4 Hz, 3H), 2.89-2.82 (m, 1H), 2.63 (hept, J=7.0 Hz, 1H), 2.24-2.10 (m, J=11.2, 4.7 Hz, 1H), 1.94-1.79 (m, J=8.6, 5.8 Hz, 1H), 1.35-1.28 (m, 3H), 1.22 (dd, J=7.0, 0.9 Hz, 6H); ESIMS m/z 547 ([M+H]$^+$).

Example 12

Step 1: Preparation of (3S,6S,7R,8R)-3-(tert-butoxycarbonylamino)-6-methyl-4,9-dioxo-8-phenethyl-1,5-dioxonan-7-yl isobutyrate

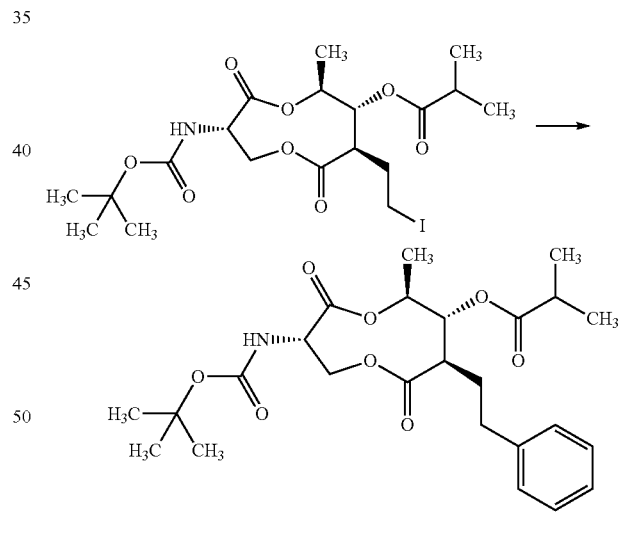

To an oven-dried flask containing a magnetic stir bar was added freshly ground zinc dust (149 mg, 2.28 mmol) and a small volume of DMF (100 μL) was added to just cover the dust. Iodine (57 mg, 0.23 mmol) was added and the mixture stirred for 2 min and then warmed to 40° C. A solution of (3S,6S,7R,8R)-3-(tert-butoxycarbonylamino)-8-(2-iodoethyl)-6-methyl-4,9-dioxo-1,5-dioxonan-7-yl isobutyrate (200 mg, 0.38 mmol) in DMF (1 mL) was added slowly at 40° C. After 15 min, the reaction mixture was cooled to ambient temperature (about 22° C.), and a solution of Pd((o-tol)$_3$P)$_2$Cl$_2$ (7.5 mg, 0.01 mmol) and 1-fluoro-4-iodo-benzene (58 uL, 0.49 mmol) in DMF (900 μL) was added to the reaction and the reaction was warmed back to 40° C. and stirring continued for 2.5 h. The mixture was cooled, diluted with EtOAc (2 mL) and filtered through a 0.45 μm fritted filter disc. The filtrate was diluted with EtOAc (20 mL), washed with saturated NaHCO₃ solution (15 mL), dried over Na₂SO₄, filtered, and concentrated. Purification by column chromatography (SiO₂, hexanes/EtOAc gradient) gave the title compound (92 mg, 51%) as a white glassy solid: ¹H NMR (300 MHz, CDCl₃) δ 7.31-7.14 (m, 3H), 7.14-7.04 (m, 2H), 5.46-5.15 (m, 2H), 5.06 (t, J=9.9 Hz, 1H), 4.91-4.72 (m, 2H), 3.61 (s, 1H), 2.76-2.48 (m, 3H), 2.40 (dt, J=13.8, 8.2 Hz, 1H), 2.17-1.99 (m, 1H), 1.73-1.52 (m, 1H), 1.45 (s, 9H), 1.25 (d, J=6.3 Hz, 3H), 1.16 (d, J=7.0 Hz, 6H); ESIMS m/z 500 ([M+Na]⁺).

Example 12

Step 2: Preparation of (3S,6S,7R,8R)-3-(3-hydroxy-4-methoxypicolinamido)-6-methyl-4,9-dioxo-8-phenethyl-1,5-dioxonan-7-yl isobutyrate (Compound 57)

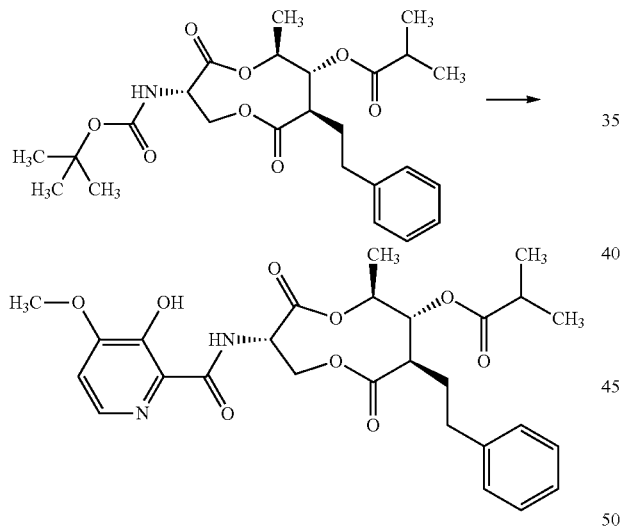

Compound 57 was prepared in the same manner as described in Example 1, Step 5, Method A to give a white solid (56 mg, 55%): mp 183-184° C.; ¹H NMR (300 MHz, CDCl₃) δ 11.80 (s, 1H), 8.66 (d, J=8.1 Hz, 1H), 8.01 (d, J=5.2 Hz, 1H), 7.34-7.15 (m, 3H), 7.15-7.02 (m, 2H), 6.89 (d, J=5.2 Hz, 1H), 5.50 (s, 1H), 5.21 (dd, J=15.1, 7.6 Hz, 1H), 5.10 (t, J=9.9 Hz, 1H), 4.96-4.83 (m, 1H), 3.95 (s, 3H), 3.80 (s, 1H), 2.78-2.51 (m, 3H), 2.51-2.35 (m, 1H), 2.21-2.06 (m, 1H), 1.73-1.58 (m, 1H), 1.28 (d, J=6.2 Hz, 3H), 1.18 (d, J=7.0 Hz, 6H); ESIMS m/z 529 ([M+H]⁺).

Compounds 58 and 59 were made as described in Example 12.

Example 13

Step 1: Preparation of (3S,6S,7R,8R)-8-(2-(benzyloxy)ethyl)-3-(tert-butoxycarbonylamino)-6-methyl-4,9-dioxo-1,5-dioxonan-7-yl isobutyrate

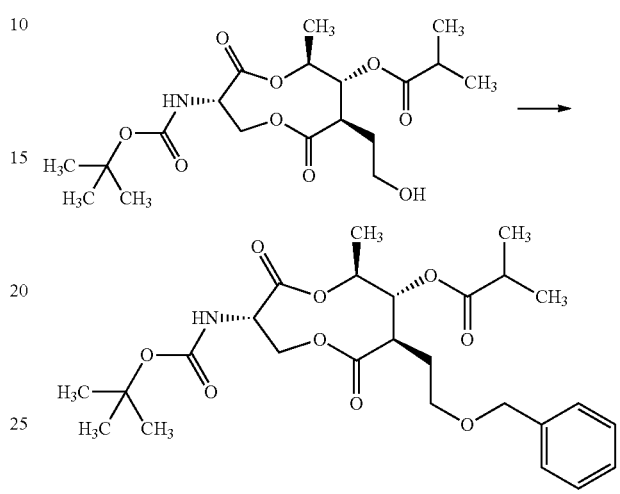

A mixture of 2-benzyloxy-1-methylpyridinium triflate (255 mg, 0.73 mmol), α,α,α-trifluorotoluene (PhCF₃, 0.75 mL), MgO (30 mg, 0.74 mmol), and (3S,6S,7R,8R)-3-(tert-butoxycarbonylamino)-8-(2-hydroxyethyl)-6-methyl-4,9-dioxo-1,5-dioxonan-7-yl isobutyrate (150 mg, 0.36 mmol) was heated at 83° C. for 1 day (d). The reaction mixture was cooled to room temperature (about 22° C.) and filtered through Celite®. The filtrate was concentrated under vacuum and purified by column chromatography (SiO₂, hexanes/EtOAc gradient) to afford the title compound (66 mg, 36%): ¹H NMR (300 MHz, CDCl₃) δ 7.40-7.21 (m, 5H), 5.28 (m, 2H), 5.06 (t, J=10.0 Hz, 1H), 4.95-4.73 (m, 2H), 4.69 (s, 2H), 4.42 (s, 2H), 3.52-3.33 (m, 3H), 2.77 (td, J=11.5, 2.8 Hz, 1H), 2.60 (dq, J=14.0, 7.0 Hz, 1H), 1.42 (s, 9H), 1.26 (d, J=6.2 Hz, 3H), 1.19 (dd, J=7.0, 2.5 Hz, 6H); ESIMS m/z 530 ([M+Na]⁺).

Example 13

Step 2: Preparation of (3S,6S,7R,8R)-8-(2-(benzyloxy)ethyl)-3-(3-hydroxy-4-methoxypicolinamido)-6-methyl-4,9-dioxo-1,5-dioxonan-7-yl isobutyrate (Compound 60)

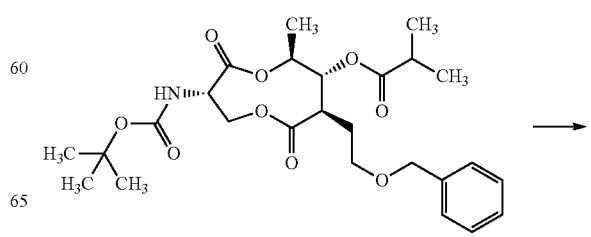

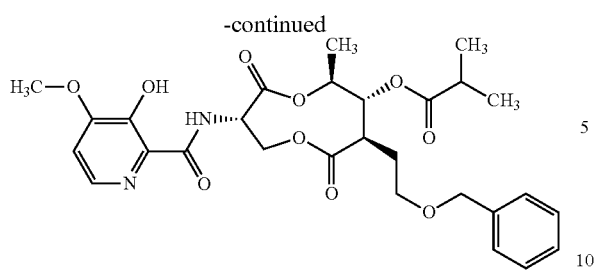

Compound 60 was prepared in the same manner as described in Example 1, Step 5, Method A to give a white solid (32 mg, 46%): mp 139-140° C.; $^1$H NMR (300 MHz, CDCl$_3$) δ 11.81 (s, 1H), 8.65 (d, J=8.3 Hz, 1H), 8.01 (d, J=5.2 Hz, 1H), 7.40-7.23 (m, 5H), 6.89 (d, J=5.2 Hz, 1H), 5.50-5.30 (m, 1H), 5.28-5.05 (m, 2H), 5.03-4.87 (m, 1H), 4.44 (s, 2H), 3.95 (s, 3H), 3.71 (s, 1H), 3.57-3.34 (m, 2H), 2.83 (td, J=11.5, 2.8 Hz, 1H), 2.61 (hept, J=7.0 Hz, 1H), 2.15-1.98 (m, 1H), 1.78-1.56 (m, 1H), 1.29 (d, J=6.2 Hz, 3H), 1.21 (d, J=7.0 Hz, 6H); ESIMS m/z 559 ([M+H]$^+$).

Example 14

Step 1: Preparation of (3S,6S,7R,8R)-3-(tert-butoxycarbonylamino)-8-(cyclohexylmethyl)-6-methyl-4,9-dioxo-1,5-dioxonan-7-yl isobutyrate

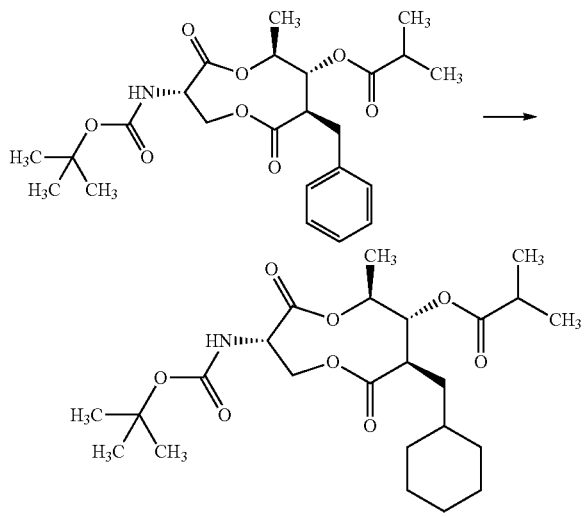

To a 50 mL high pressure reactor with a magnetic stir bar was added (3S,6S,7R,8R)-8-benzyl-3-(tert-butoxycarbonylamino)-6-methyl-4,9-dioxo-1,5-dioxonan-7-yl isobutyrate (400 mg, 0.863 mmol) in THF (3 mL) to give a colorless solution. To the solution was added 5% Rh/C (50 mg, 0.024 mmol). After the reactor was sealed, it was purged with hydrogen gas (4 times). The reactor was charged to approximately 600 psi of H$_2$ at room temperature (about 22° C.) and then the reaction was warmed to 70° C. and stirred at for 6 h. The reaction mixture was cooled, filtered, and concentrated. The residue was purified via column chromatography (SiO$_2$, hexanes/EtOAc gradient) to afford the title compound (414 mg, 92%) as an off-white solid: $^1$H NMR (400 MHz, CDCl$_3$) δ 5.32 (dd, J=39.3, 12.3 Hz, 2H), 5.01 (t, J=9.9 Hz, 1H), 4.94-4.72 (m, 2H), 3.58 (s, J=51.8 Hz, 1H), 2.72-2.51 (m, 2H), 1.78-1.52 (m, 6H), 1.45 (s, J=6.0 Hz, 9H), 1.26 (d, J=6.3 Hz, 3H), 1.20 (dd, J=7.0, 3.0 Hz, 6H), 1.19-1.04 (m, 4H), 1.02-0.68 (m, 3H); $^{13}$C NMR (101 MHz, CDCl$_3$) δ 175.50, 172.74, 154.78, 133.68, 123.39, 80.39, 75.22, 74.50, 67.85, 65.49, 51.47, 47.36, 35.85, 35.40, 34.05, 34.01, 32.09, 28.19, 26.28, 26.00, 25.87, 18.95, 18.82, 17.77; ESIMS m/z 492 ([M+Na]$^+$).

Example 14

Step 2: Preparation of (3S,6S,7R,8R)-8-(cyclohexylmethyl)-3-(3-hydroxy-4-methoxypicolinamido)-6-methyl-4,9-dioxo-1,5-dioxonan-7-yl isobutyrate (Compound 61)

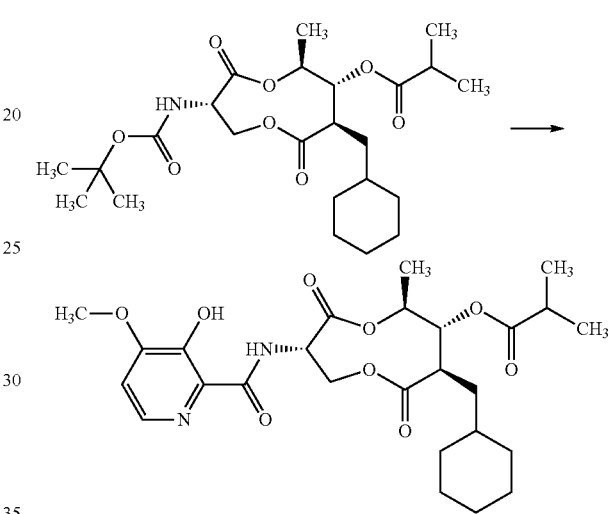

Compound 61 was prepared in the same manner as described in Example 1, Step 5, Method A to give a white solid (175 mg, 48%): mp 188-189° C.; $^1$H NMR (300 MHz, CDCl$_3$) δ 11.81 (s, 1H), 8.66 (d, J=8.0 Hz, 1H), 8.01 (d, J=5.2 Hz, 1H), 6.89 (d, J=5.2 Hz, 1H), 5.48 (s, 1H), 5.18 (s, 1H), 5.05 (t, J=9.8 Hz, 1H), 4.99-4.87 (m, 1H), 3.95 (s, 3H), 3.76 (s, 1H), 2.70 (t, J=10.1 Hz, 1H), 2.60 (dd, J=14.0, 7.0 Hz, 1H), 1.79-1.59 (m, 6H), 1.28 (d, J=6.2 Hz, 3H), 1.21 (dd, J=7.0, 2.3 Hz, 6H), 1.16 (d, J=7.0 Hz, 4H), 1.02-0.69 (m, 3H); ESIMS m/z 521 ([M+H]$^+$).

Compound 62 was made as described in Example 14.

Example 15

Preparation of (3S,6S,7R,8R)-8-heptyl-3-(3-hydroxy-4-methoxypicolinamido)-6-methyl-4,9-dioxo-1,5-dioxonan-7-yl isobutyrate (Compound 63)

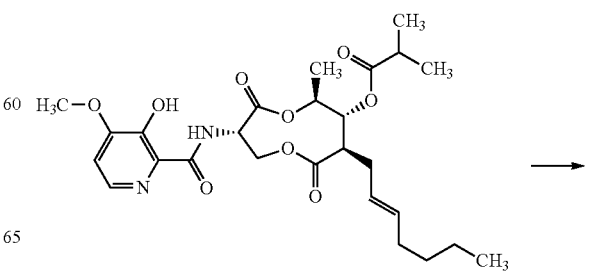

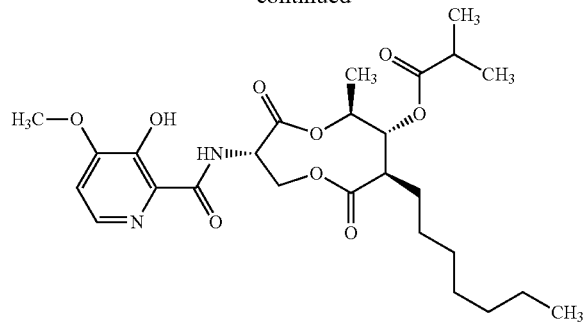

(3S,6S,7R,8R)-8-((E)-hept-2-enyl)-3-(3-hydroxy-4-methoxypicolinamido)-6-methyl-4,9-dioxo-1,5-dioxonan-7-yl isobutyrate (163 mg, 0.31 mmol) was dissolved in EtOAc (15 mL) and passed through an H-Cube® Continuous Flow hydrogenator equipped with a 10% Pd/C cartridge (full H$_2$, 80° C., 1 mL/min flow rate). The resulting solution was concentrated in vacuo to give the title compound (162 mg, 99%) as a white solid: mp 131-134° C.; IR (neat) 3341, 1739, 1654, 1141 cm$^{-1}$; $^1$H NMR (400 MHz, CDCl$_3$) δ 11.81 (s, 1H), 8.66 (d, J=8.1 Hz, 1H), 8.01 (d, J=5.2 Hz, 1H), 6.89 (d, J=5.2 Hz, 1H), 5.19 (m, 1H), 5.14-5.02 (m, 1H), 5.02-4.87 (m, 1H), 3.95 (s, 3H), 3.87-3.69 (m, 1H), 2.70-2.52 (m, 2H), 1.80-1.66 (m, 1H), 1.43-1.08 (m, 21H), 0.86 (t, J=6.8 Hz, 3H); $^{13}$C NMR (101 MHz, CDCl$_3$) δ 175.59, 172.71, 169.77, 169.00, 155.47, 148.87, 140.74, 129.98, 109.74, 75.20, 74.94, 65.12, 56.16, 50.07, 34.13, 31.70, 29.25, 28.98, 28.40, 27.09, 22.62, 18.98, 18.97, 17.82, 14.08; ESIMS m/z 523.4 ([M+H]$^+$).

Compound 64 was made as described in Example 15.

Example 16

Step 1: Preparation of (3S,6S,7R,8R)-3-(tert-butoxycarbonylamino)-6-methyl-4,9-dioxo-8-((pyridin-2-ylthio)methyl)-1,5-dioxonan-7-yl isobutyrate

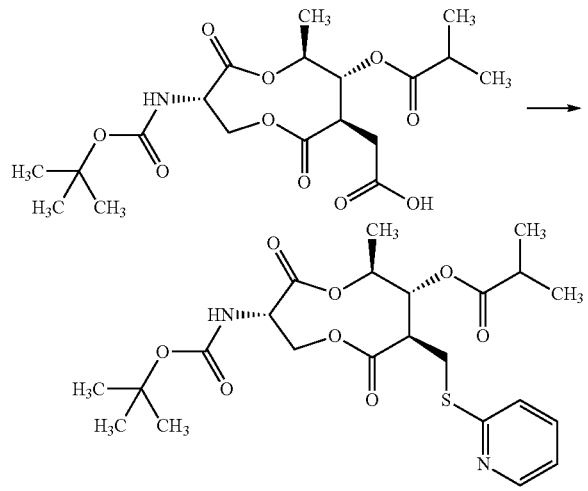

To a solution of 2-((3S,7R,8R,9S)-3-(tert-butoxycarbonylamino)-8-(isobutyryloxy)-9-methyl-2,6-dioxo-1,5-dioxonan-7-yl)acetic acid (500 mg, 1.2 mmol) in anhydrous THF (7 mL) at −15° C. was added N-methylmorpholine (127 μL, 1.2 mmol) and isobutylchloroformate (152 μL, 1.2 mmol). The mixture was stirred for 5 min and then treated with a solution of 2-mercaptopyridine N-oxide (177 mg, 1.4 mmol) and TEA (162 μL, 1.2 mmol) in THF (2 mL). The reaction was stirred at −15° C. in the dark (covered with aluminum foil) for 1 h. The reaction was then filtered, concentrated, and the resulting bright yellow residue dissolved in CH$_2$Cl$_2$ (5 mL) and irradiated for 1 hr. The crude reaction mixture was concentrated and purified by flash chromatography (SiO$_2$, 10% EtOAc/hexanes) to furnish the title compound (169 mg, 29%) as a fluffy white solid: mp 54-58° C.; IR (neat) 3370, 2980, 2939, 2878, 1753, 1718 cm$^{-1}$; $^1$H NMR (400 MHz, CDCl$_3$) δ 8.35 (d, J=4.9 Hz, 1H), 7.48-7.41 (m, 1H), 7.11 (d, J=8.0 Hz, 1H), 7.00-6.94 (m, 1H), 5.32 (bs, J=12.9 Hz, 1H), 5.21-5.07 (m, 2H), 4.87 (dt, J=16.1, 6.4 Hz, 2H), 3.66-3.60 (m, 1H), 3.59 (bs, 1H), 3.15-3.00 (m, 2H), 2.68 (dq, J=14.2, 7.1 Hz, 1H), 1.43 (s, 9H), 1.33-1.25 (m, 9H); $^{13}$C NMR (101 MHz, CDCl$_3$) δ 176.11, 171.91, 171.33, 157.67, 155.07, 149.73, 136.35, 122.89, 120.10, 81.00, 75.34, 74.76, 66.22, 51.66, 51.26, 34.68, 28.74, 28.64 (3), 19.38, 19.23, 18.14; ESIMS m/z 519 ([M+Na]$^+$).

Example 16

Step 2: Preparation of (3S,6S,7R,8R)-3-(3-hydroxy-4-methoxypicolinamido)-6-methyl-4,9-dioxo-8-((pyridin-2-ylthio)methyl)-1,5-dioxonan-7-yl isobutyrate (Compound 65)

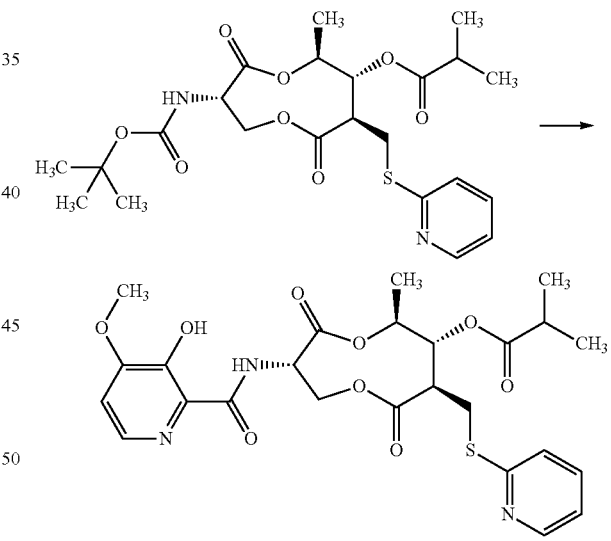

Compound 65 was prepared in the same manner as described in Example 1, Step 5, Method B to give a white solid (115 mg, 70%): mp 148-150° C.; IR (neat) 3356, 2976, 2943, 1742, 1653 cm$^{-1}$; $^1$H NMR (400 MHz, CDCl$_3$) δ 11.81 (s, 1H), 8.61 (d, J=8.4 Hz, 1H), 8.41-8.36 (m, 1H), 8.01 (d, J=5.2 Hz, 1H), 7.51-7.44 (m, 1H), 7.17-7.12 (m, 1H), 7.01 (ddd, J=7.2, 4.9, 1.0 Hz, 1H), 6.90 (d, J=5.2 Hz, 1H), 5.50 (bs, 1H), 5.29-5.13 (m, 2H), 4.97 (dd, J=9.8, 6.2 Hz, 1H), 3.97 (s, 3H), 3.68 (m, 2H), 3.16 (t, J=9.4 Hz, 2H), 2.73 (dt, J=14.0, 7.1 Hz, 1H), 1.38-1.28 (m, 9H); $^{13}$C NMR (101 MHz, CDCl$_3$) δ 176.21, 172.00, 170.30, 169.38, 157.47, 155.81, 149.78, 149.19, 141.19, 136.46, 130.27, 122.94, 120.20, 110.13, 75.08, 65.47, 56.59, 51.20, 50.09, 39.06, 34.70, 28.67, 19.45, 19.28, 18.19; ESIMS m/z 548 ([M+H]+).

Example 17

Preparation of (3S,6S,7R,8R)-3-(3-acetoxy-4-methoxypicolinamido)-8-(cyclohexylmethyl)-6-methyl-4,9-dioxo-1,5-dioxonan-7-yl isobutyrate (Compound 66)

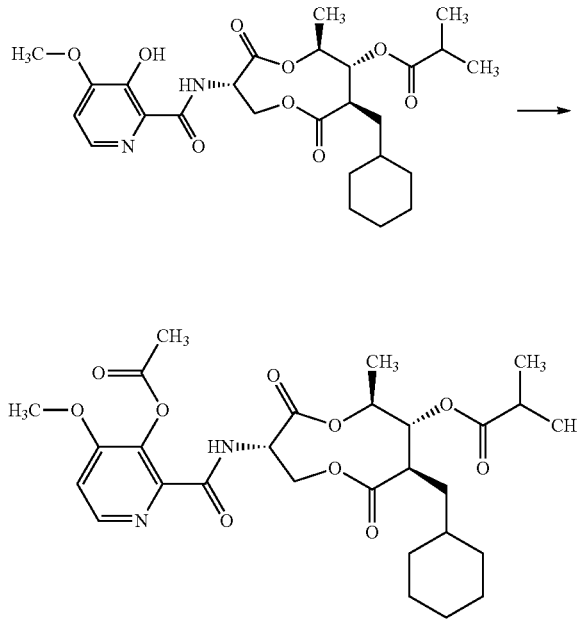

Acetyl chloride (9 μL, 0.125 mmol) was added to a solution of (3S,6S,7R,8R)-8-(cyclohexylmethyl)-3-(3-hydroxy-4-methoxypicolinamido)-6-methyl-4,9-dioxo-1,5-dioxonan-7-yl isobutyrate (50 mg, 0.100 mmol) and pyridine (40 μL, 0.480 mmol) in $CH_2Cl_2$ (1 mL), and the reaction was stirred at ambient temperature (about 22° C.) overnight. The solution was loaded directly onto a pre-packed $SiO_2$ column for purification by column chromatography (0→30% EtOAc/$CH_2Cl_2$) to afford the title compound (28 mg, 52%) as a white solid: mp 164-170° C.; $^1$H NMR (400 MHz, $CDCl_3$) δ 8.70 (d, J=7.5 Hz, 1H), 8.35 (d, J=5.4 Hz, 1H), 7.03 (d, J=5.5 Hz, 1H), 5.47 (br s, 1H), 5.25-5.11 (m, 1H), 5.03 (t, J=9.9 Hz, 1H), 4.97-4.84 (m, 1H), 3.92 (s, 3H), 3.72 (br s, 1H), 2.69 (dd, J=16.8, 7.0 Hz, 1H), 2.60 (sept, J=14.0, 7.0 Hz, 1H), 2.40 (s, 3H), 1.83-1.54 (m, 6H), 1.36-1.02 (m, 14H), 0.94-0.67 (m, 2H); HRMS-ESI (m/z): calcd for $C_{28}H_{38}N_2O_{10}$, 562.2526; found, 562.2516.

Compounds 67-70 were made as described in Example 17.

Example 18

Evaluation of Fungicidal Activity: Leaf Blotch of Wheat (*Mycosphaerella graminicola*; Anamorph: *Septoria tritici*; Bayer Code SEPTTR)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse at 20° C. for disease to develop.

Example 19

Evaluation of Fungicidal Activity: Wheat Brown Rust (*Puccinia triticina*. Synonym: *Puccinia recondite* f. sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia recondite* f. sp. *tritici* either prior to or after fungicide treatments. After inoculation the plants were kept in 100% relative humidity overnight to permit spores to germinate and infect the leaf. The plants were then transferred to a greenhouse set at 24 C for disease to develop.

TABLE 1

| | Compound Structure and Appearance | |
|---|---|---|
| Compound Number | Appearance | Structure |
| 1 | White Solid | (structure shown) |

TABLE 1-continued

Compound Structure and Appearance

| Compound Number | Appearance | Structure |
|---|---|---|
| 2 | Yellow Solid | 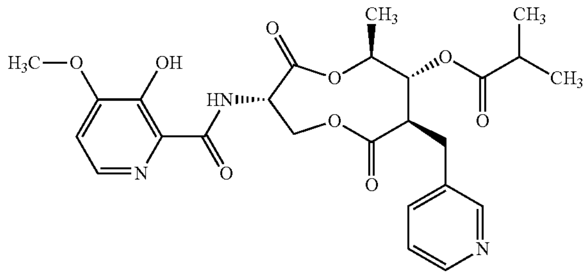 [SMILES: COc1ccnc(C(=O)N[C@H]2COC(=O)[C@H](Cc3cccnc3)[C@@H](OC(=O)C(C)C)[C@H](C)OC2=O)c1O] |
| 3 | Dark Brown Solid | 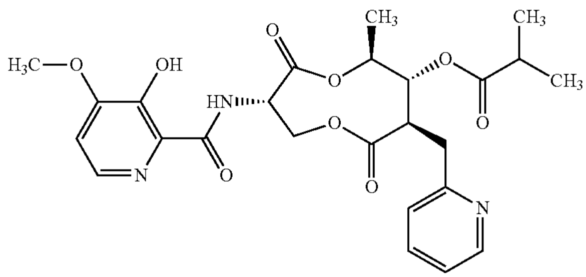 [SMILES: COc1ccnc(C(=O)N[C@H]2COC(=O)[C@H](Cc3ccccn3)[C@@H](OC(=O)C(C)C)[C@H](C)OC2=O)c1O] |
| 4 | White Solid | 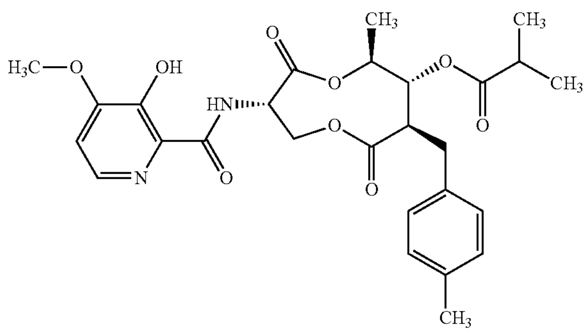 [SMILES: COc1ccnc(C(=O)N[C@H]2COC(=O)[C@H](Cc3ccc(C)cc3)[C@@H](OC(=O)C(C)C)[C@H](C)OC2=O)c1O] |
| 5 | Yellow Solid | 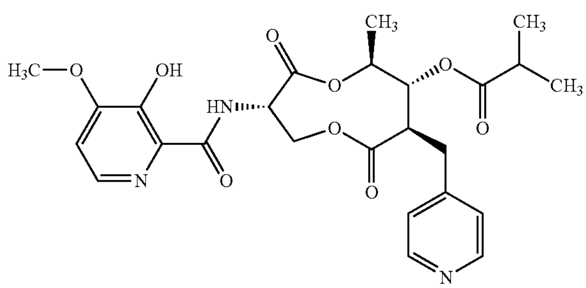 [SMILES: COc1ccnc(C(=O)N[C@H]2COC(=O)[C@H](Cc3ccncc3)[C@@H](OC(=O)C(C)C)[C@H](C)OC2=O)c1O] |
| 6 | White Solid | 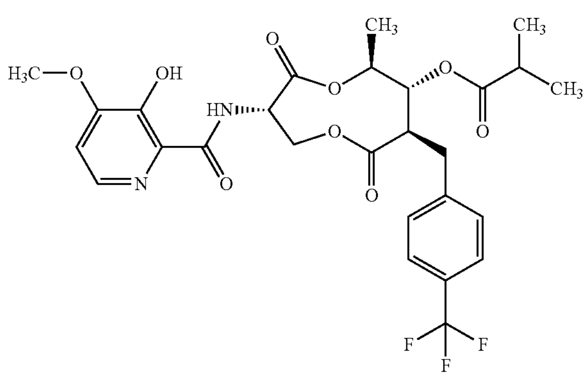 [SMILES: COc1ccnc(C(=O)N[C@H]2COC(=O)[C@H](Cc3ccc(C(F)(F)F)cc3)[C@@H](OC(=O)C(C)C)[C@H](C)OC2=O)c1O] |

TABLE 1-continued

Compound Structure and Appearance

| Compound Number | Appearance | Structure |
|---|---|---|
| 7 | White Solid | 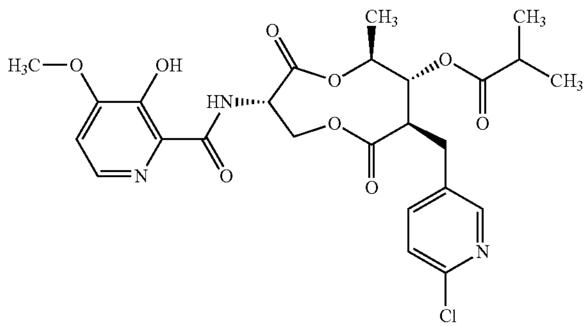 [SMILES: COc1ccnc(C(=O)N[C@H]2COC(=O)[C@H](Cc3ccc(Cl)nc3)[C@@H](OC(=O)C(C)C)[C@H](C)OC2=O)c1O] |
| 8 | Thick Oil | 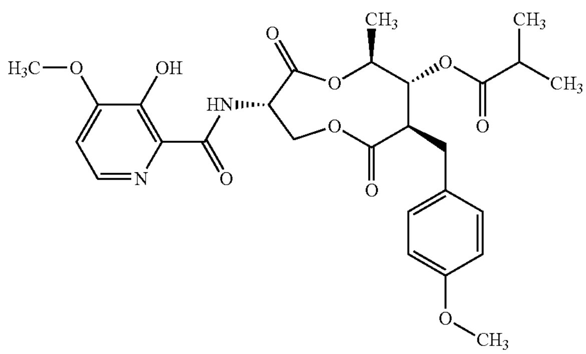 [SMILES: COc1ccc(C[C@H]2C(=O)OC[C@H](NC(=O)c3nccc(OC)c3O)C(=O)O[C@@H](C)[C@@H]2OC(=O)C(C)C)cc1] |
| 9 | White Solid | 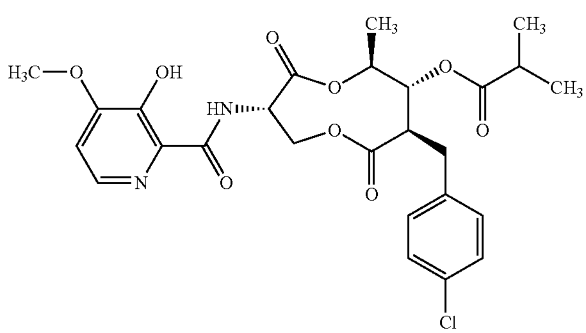 [SMILES: COc1ccnc(C(=O)N[C@H]2COC(=O)[C@H](Cc3ccc(Cl)cc3)[C@@H](OC(=O)C(C)C)[C@H](C)OC2=O)c1O] |
| 10 | White Solid | 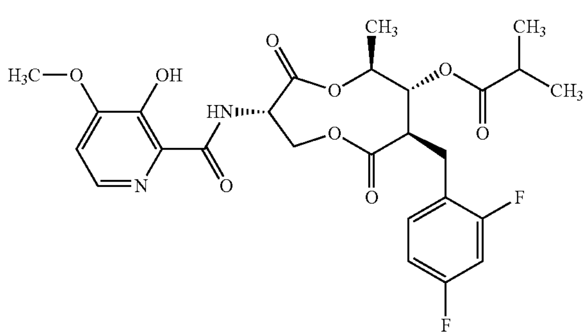 [SMILES: COc1ccnc(C(=O)N[C@H]2COC(=O)[C@H](Cc3ccc(F)cc3F)[C@@H](OC(=O)C(C)C)[C@H](C)OC2=O)c1O] |
| 11 | White Solid | 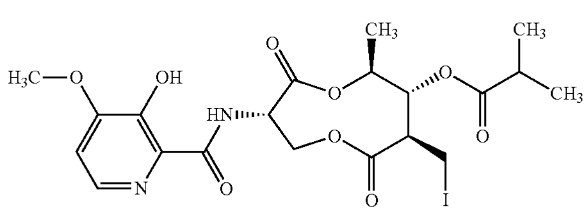 [SMILES: COc1ccnc(C(=O)N[C@H]2COC(=O)[C@H](CI)[C@@H](OC(=O)C(C)C)[C@H](C)OC2=O)c1O] |

TABLE 1-continued
Compound Structure and Appearance
| Compound Number | Appearance | Structure |
|---|---|---|
| 12 | White Solid | 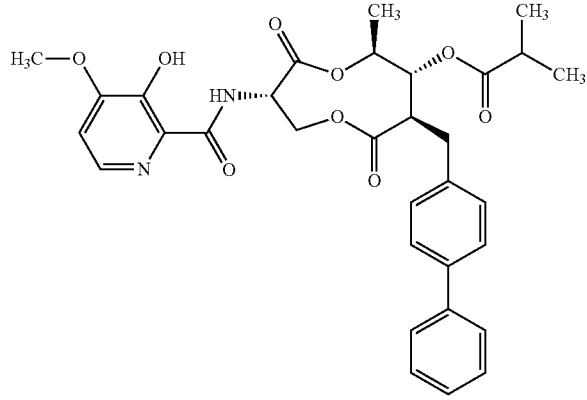 [SMILES: COc1ccnc(C(=O)N[C@H]2COC(=O)[C@H](Cc3ccc(-c4ccccc4)cc3)[C@@H](OC(=O)C(C)C)[C@H](C)OC2=O)c1O] |
| 13 | White Solid | 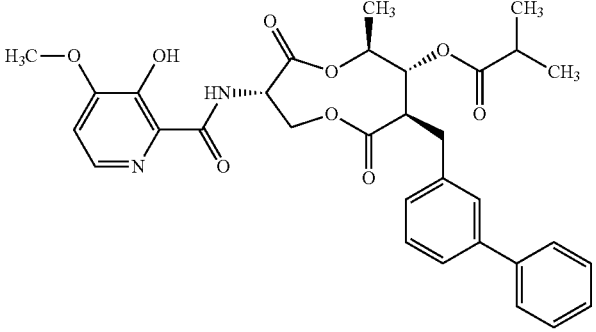 [SMILES: COc1ccnc(C(=O)N[C@H]2COC(=O)[C@H](Cc3cccc(-c4ccccc4)c3)[C@@H](OC(=O)C(C)C)[C@H](C)OC2=O)c1O] |
| 14 | White Solid | 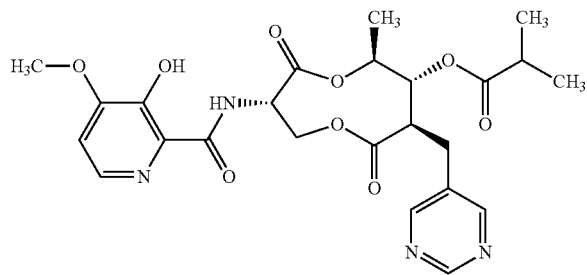 [SMILES: COc1ccnc(C(=O)N[C@H]2COC(=O)[C@H](Cc3cncnc3)[C@@H](OC(=O)C(C)C)[C@H](C)OC2=O)c1O] |
| 15 | White Solid | 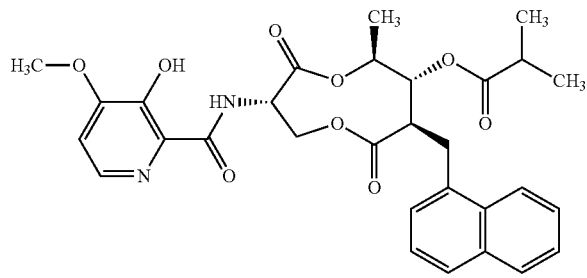 [SMILES: COc1ccnc(C(=O)N[C@H]2COC(=O)[C@H](Cc3cccc4ccccc34)[C@@H](OC(=O)C(C)C)[C@H](C)OC2=O)c1O] |

TABLE 1-continued
Compound Structure and Appearance
| Compound Number | Appearance | Structure |
|---|---|---|
| 16 | White Solid | 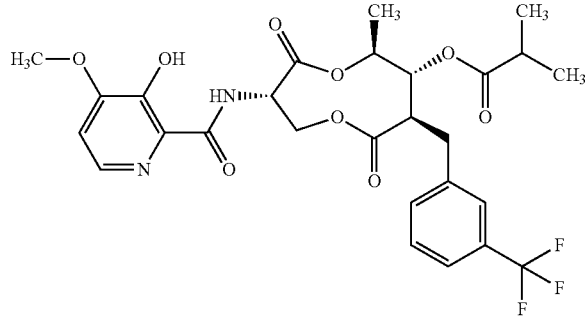 [SMILES: COc1ccnc(C(=O)N[C@H]2COC(=O)[C@H](Cc3cccc(C(F)(F)F)c3)[C@@H](OC(=O)C(C)C)[C@H](C)OC2=O)c1O] |
| 17 | Tan Solid | 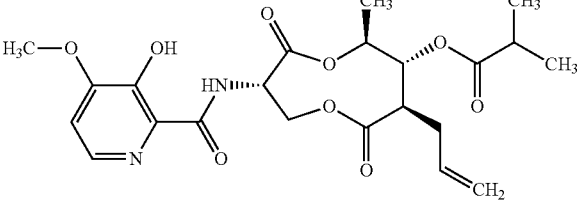 |
| 18 | White Solid | 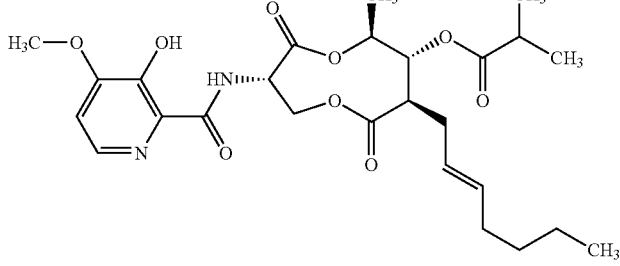 |
| 19 | Off White Solid | 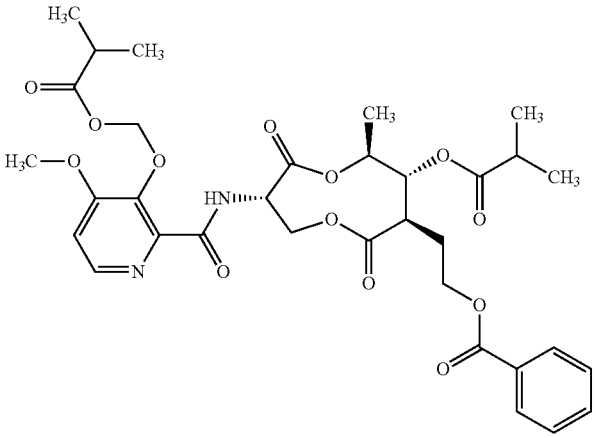 [SMILES: COc1ccnc(C(=O)N[C@H]2COC(=O)[C@H](CCOC(=O)c3ccccc3)[C@@H](OC(=O)C(C)C)[C@H](C)OC2=O)c1OCOC(=O)C(C)C] |

TABLE 1-continued

Compound Structure and Appearance

| Compound Number | Appearance | Structure |
|---|---|---|
| 20 | Yellow Oil | 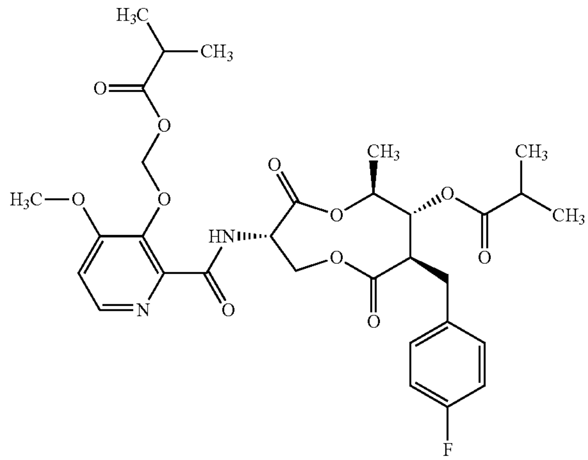 [SMILES: COc1ccnc(C(=O)N[C@H]2COC(=O)[C@H](Cc3ccc(F)cc3)[C@@H](OC(=O)C(C)C)[C@H](C)OC2=O)c1OCOC(=O)C(C)C] |
| 21 | Glassy Solid | 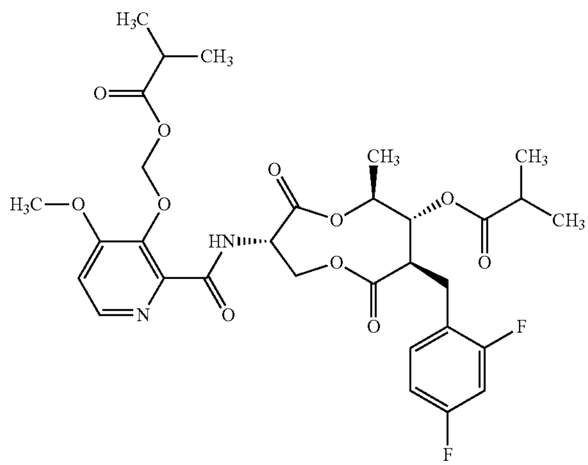 [SMILES: COc1ccnc(C(=O)N[C@H]2COC(=O)[C@H](Cc3ccc(F)cc3F)[C@@H](OC(=O)C(C)C)[C@H](C)OC2=O)c1OCOC(=O)C(C)C] |
| 22 | White Solid | 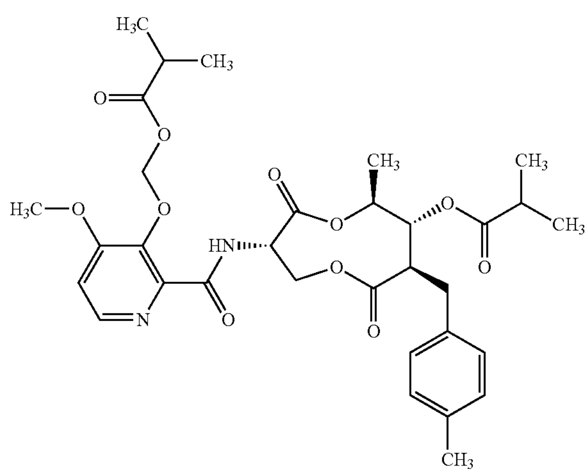 [SMILES: COc1ccnc(C(=O)N[C@H]2COC(=O)[C@H](Cc3ccc(C)cc3)[C@@H](OC(=O)C(C)C)[C@H](C)OC2=O)c1OCOC(=O)C(C)C] |

TABLE 1-continued
Compound Structure and Appearance
| Compound Number | Appearance | Structure |
|---|---|---|
| 23 | Yellow Solid | 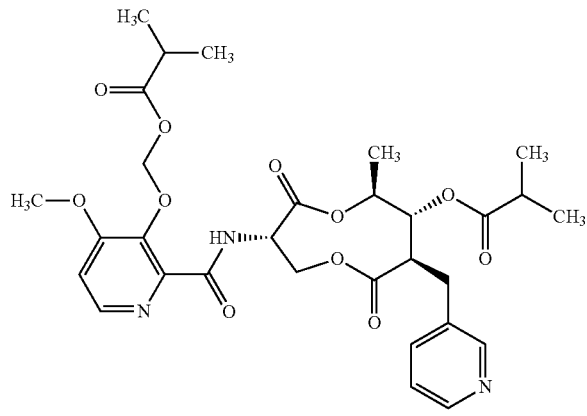 [SMILES: COc1ccnc(C(=O)N[C@H]2COC(=O)[C@H](Cc3cccnc3)[C@@H](OC(=O)C(C)C)[C@H](C)OC2=O)c1OCOC(=O)C(C)C] |
| 24 | White Solid | 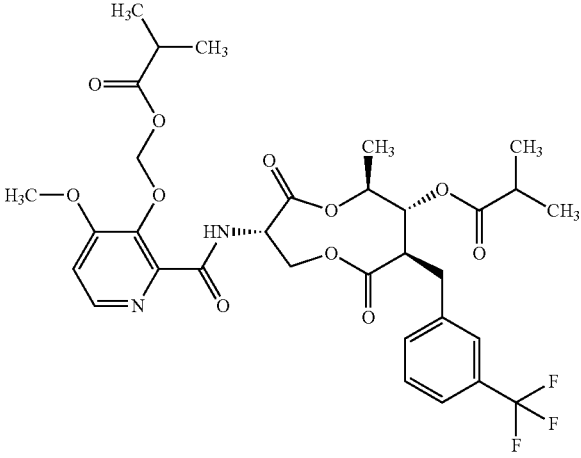 [SMILES: COc1ccnc(C(=O)N[C@H]2COC(=O)[C@H](Cc3cccc(C(F)(F)F)c3)[C@@H](OC(=O)C(C)C)[C@H](C)OC2=O)c1OCOC(=O)C(C)C] |
| 25 | White Solid | 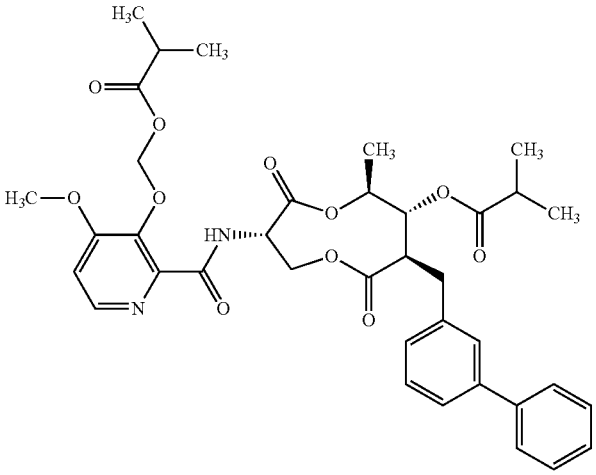 [SMILES: COc1ccnc(C(=O)N[C@H]2COC(=O)[C@H](Cc3cccc(-c4ccccc4)c3)[C@@H](OC(=O)C(C)C)[C@H](C)OC2=O)c1OCOC(=O)C(C)C] |

TABLE 1-continued
Compound Structure and Appearance
| Compound Number | Appearance | Structure |
|---|---|---|
| 26 | White Solid | 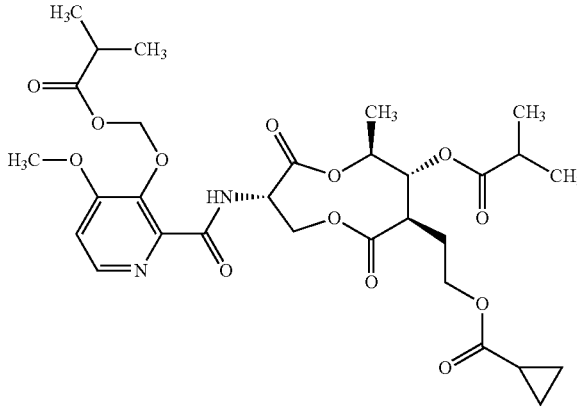 [SMILES: COc1ccnc(C(=O)N[C@H]2COC(=O)[C@H](CCOC(=O)C3CC3)[C@@H](OC(=O)C(C)C)[C@H](C)OC2=O)c1OCOC(=O)C(C)C] |
| 27 | White Solid | 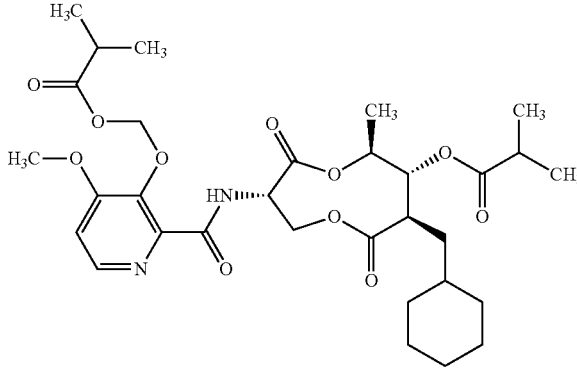 [SMILES: COc1ccnc(C(=O)N[C@H]2COC(=O)[C@H](CC3CCCCC3)[C@@H](OC(=O)C(C)C)[C@H](C)OC2=O)c1OCOC(=O)C(C)C] |
| 28 | Sticky Solid | 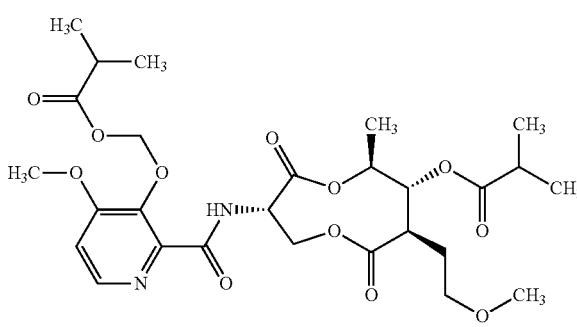 |
| 29 | Sticky Colorless Solid | 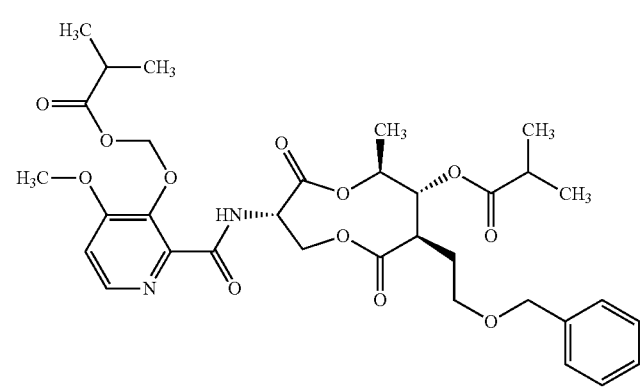 [SMILES: COc1ccnc(C(=O)N[C@H]2COC(=O)[C@H](CCOCc3ccccc3)[C@@H](OC(=O)C(C)C)[C@H](C)OC2=O)c1OCOC(=O)C(C)C] |

TABLE 1-continued

Compound Structure and Appearance

| Compound Number | Appearance | Structure |
|---|---|---|
| 30 | White Semi-Solid | 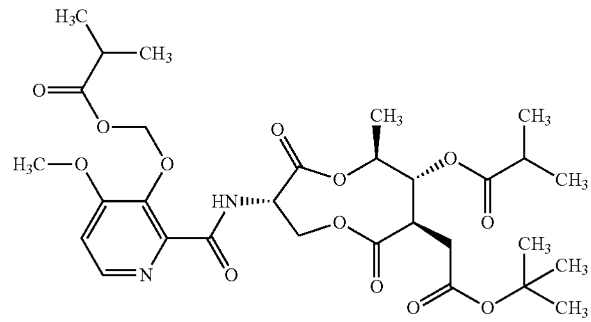 [SMILES: COc1ccnc(C(=O)N[C@H]2COC(=O)[C@H](CC(=O)OC(C)(C)C)[C@@H](OC(=O)C(C)C)[C@H](C)OC2=O)c1OCOC(=O)C(C)C] |
| 31 | Sticky Oil | 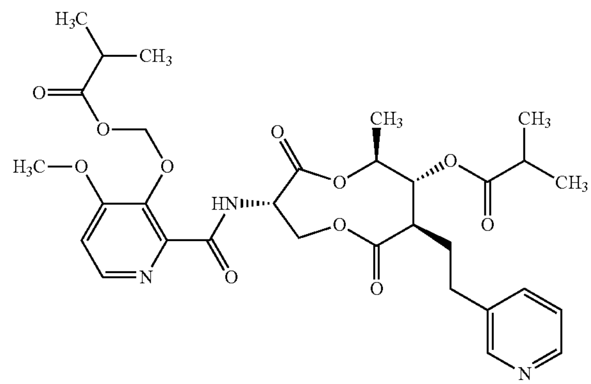 [SMILES: COc1ccnc(C(=O)N[C@H]2COC(=O)[C@H](CCc3cccnc3)[C@@H](OC(=O)C(C)C)[C@H](C)OC2=O)c1OCOC(=O)C(C)C] |
| 32 | White Solid | 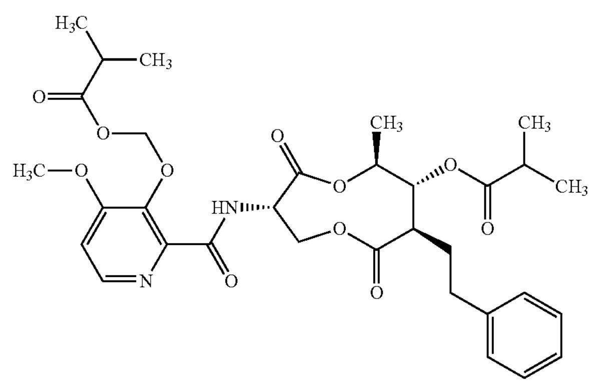 [SMILES: COc1ccnc(C(=O)N[C@H]2COC(=O)[C@H](CCc3ccccc3)[C@@H](OC(=O)C(C)C)[C@H](C)OC2=O)c1OCOC(=O)C(C)C] |
| 33 | Yellow Oil | 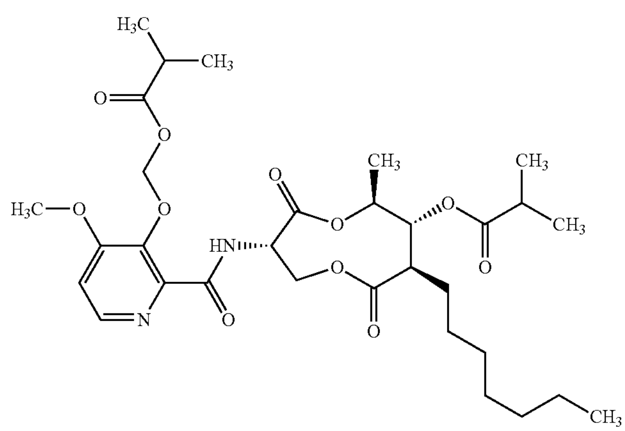 [SMILES: CCCCCCC[C@H]1C(=O)OC[C@H](NC(=O)c2nccc(OC)c2OCOC(=O)C(C)C)C(=O)O[C@@H](C)[C@@H]1OC(=O)C(C)C] |

TABLE 1-continued
Compound Structure and Appearance
| Compound Number | Appearance | Structure |
|---|---|---|
| 34 | White Foam | 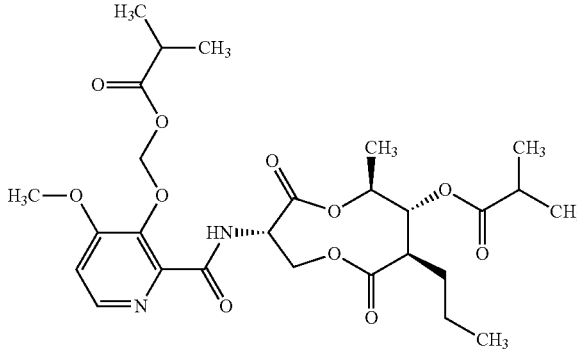 [SMILES: CCC[C@H]1C(=O)OC[C@H](NC(=O)c2nccc(OC)c2OCOC(=O)C(C)C)C(=O)O[C@@H](C)[C@@H]1OC(=O)C(C)C] |
| 35 | White Solid | 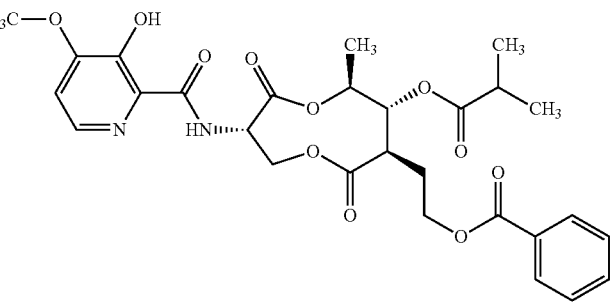 |
| 36 | Glassy Solid | 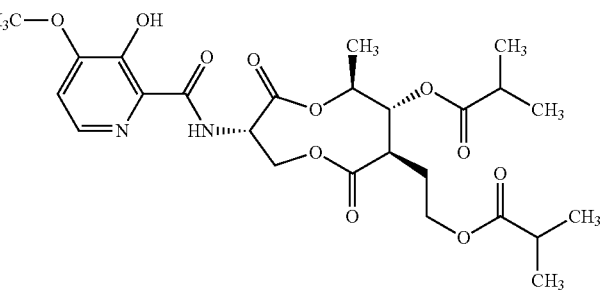 |
| 37 | White Solid | 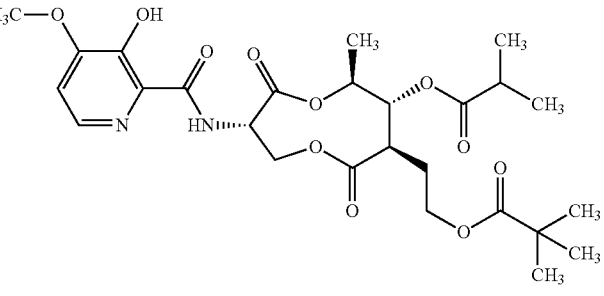 |
| 38 | Pale Solid | 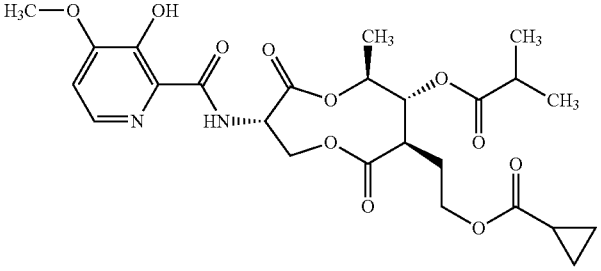 [SMILES: COc1ccnc(C(=O)N[C@H]2COC(=O)[C@H](CCOC(=O)C3CC3)[C@@H](OC(=O)C(C)C)[C@H](C)OC2=O)c1O] |

TABLE 1-continued

Compound Structure and Appearance

| Compound Number | Appearance | Structure |
|---|---|---|
| 39 | White Solid | 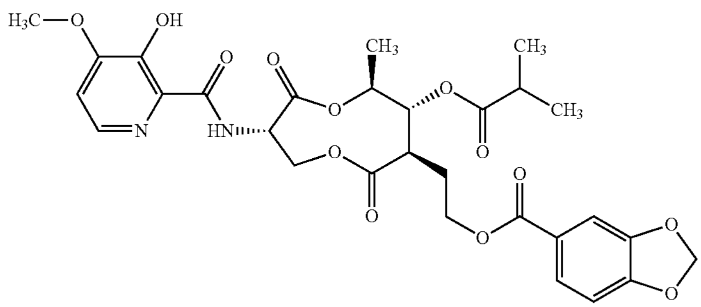 [SMILES: COc1ccnc(C(=O)N[C@H]2COC(=O)[C@H](CCOC(=O)c3ccc4c(c3)OCO4)[C@@H](OC(=O)C(C)C)[C@H](C)OC2=O)c1O] |
| 40 | White Solid | 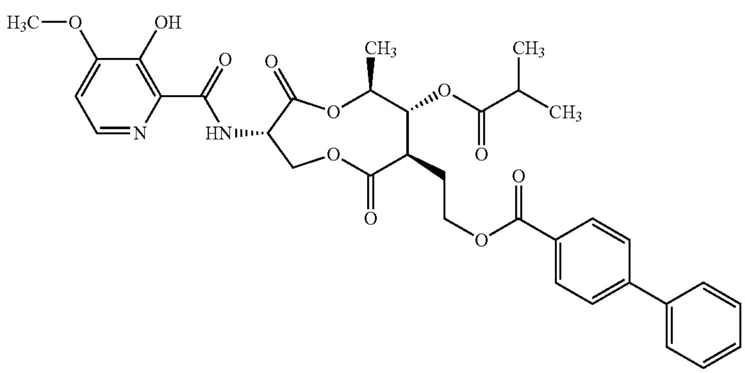 [SMILES: COc1ccnc(C(=O)N[C@H]2COC(=O)[C@H](CCOC(=O)c3ccc(-c4ccccc4)cc3)[C@@H](OC(=O)C(C)C)[C@H](C)OC2=O)c1O] |
| 41 | Sticky Solid | 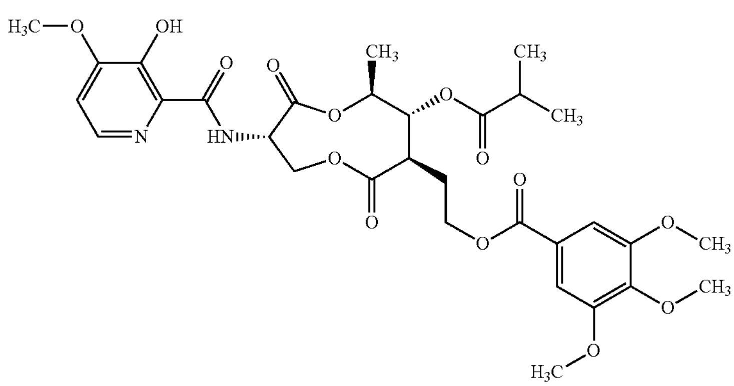 |
| 42 | White Solid | 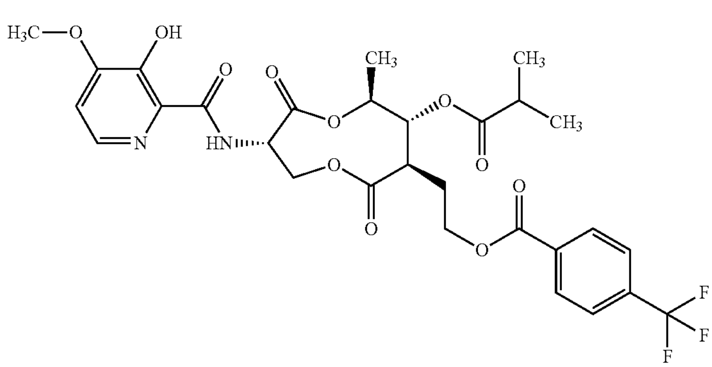 [SMILES: COc1ccnc(C(=O)N[C@H]2COC(=O)[C@H](CCOC(=O)c3ccc(C(F)(F)F)cc3)[C@@H](OC(=O)C(C)C)[C@H](C)OC2=O)c1O] |

TABLE 1-continued

Compound Structure and Appearance

| Compound Number | Appearance | Structure |
|---|---|---|
| 43 | White Solid | 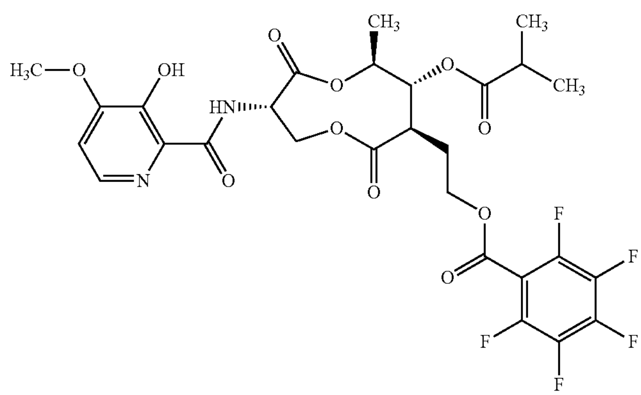 [SMILES: COc1ccnc(C(=O)N[C@H]2COC(=O)[C@H](CCOC(=O)c3c(F)c(F)c(F)c(F)c3F)[C@@H](OC(=O)C(C)C)[C@H](C)OC2=O)c1O] |
| 44 | White Solid | 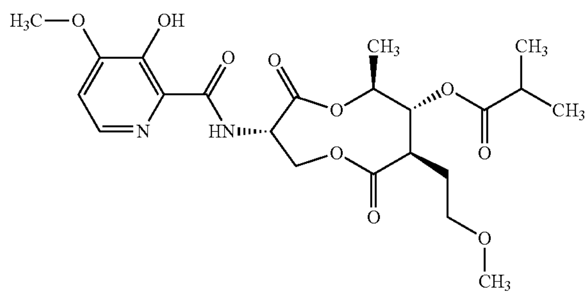 [SMILES: COCC[C@H]1C(=O)OC[C@H](NC(=O)c2nccc(OC)c2O)C(=O)O[C@@H](C)[C@@H]1OC(=O)C(C)C] |
| 45 | White Solid | 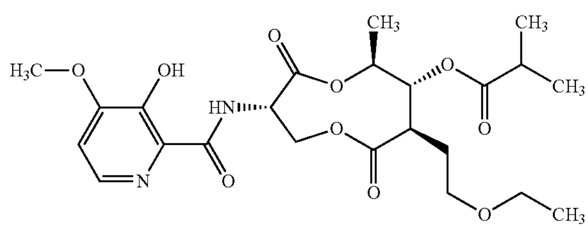 [SMILES: CCOCC[C@H]1C(=O)OC[C@H](NC(=O)c2nccc(OC)c2O)C(=O)O[C@@H](C)[C@@H]1OC(=O)C(C)C] |
| 46 | White Solid | 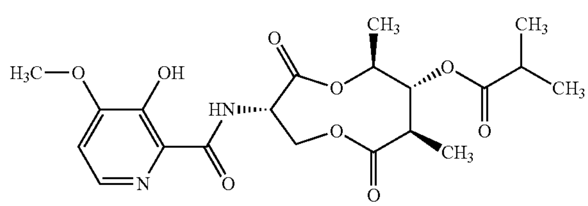 [SMILES: COc1ccnc(C(=O)N[C@H]2COC(=O)[C@H](C)[C@@H](OC(=O)C(C)C)[C@H](C)OC2=O)c1O] |
| 47 | White Solid | 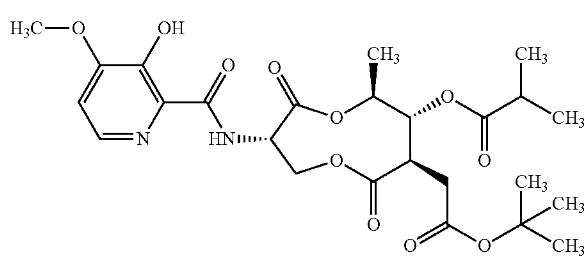 [SMILES: COc1ccnc(C(=O)N[C@H]2COC(=O)[C@H](CC(=O)OC(C)(C)C)[C@@H](OC(=O)C(C)C)[C@H](C)OC2=O)c1O] |

TABLE 1-continued
Compound Structure and Appearance
| Compound Number | Appearance | Structure |
|---|---|---|
| 48 | White Solid | 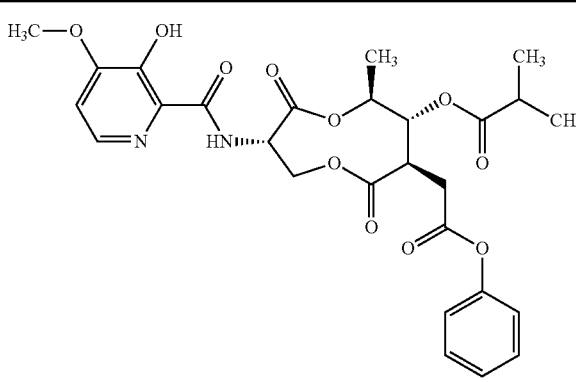 |
| 49 | White Solid | 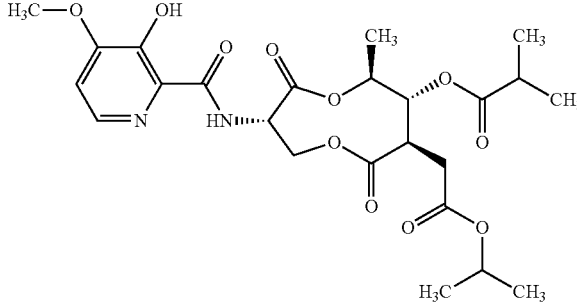 |
| 50 | White Solid | 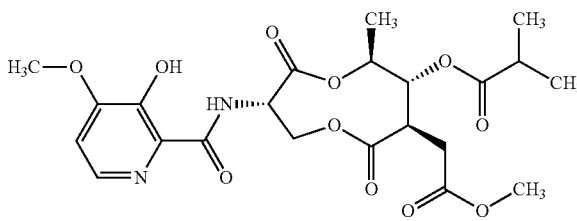 |
| 51 | White Solid | 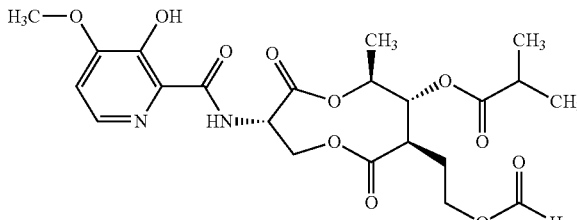 |
| 52 | White Solid | 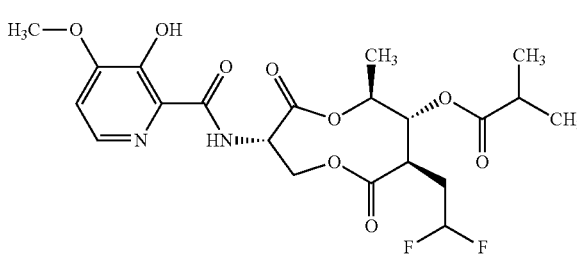 |

TABLE 1-continued

Compound Structure and Appearance

| Compound Number | Appearance | Structure |
|---|---|---|
| 53 | White Solid | 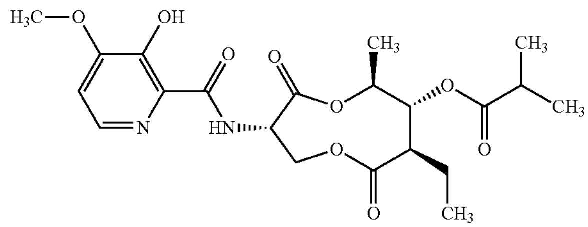 [SMILES: CC[C@H]1C(=O)OC[C@H](NC(=O)c2nccc(OC)c2O)C(=O)O[C@@H](C)[C@@H]1OC(=O)C(C)C] |
| 54 | White Solid | 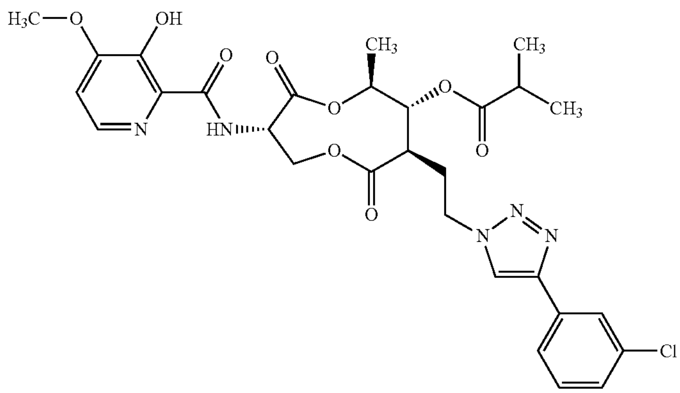 [SMILES: COc1ccnc(C(=O)N[C@H]2COC(=O)[C@H](CCn3cc(-c4cccc(Cl)c4)nn3)[C@@H](OC(=O)C(C)C)[C@H](C)OC2=O)c1O] |
| 55 | White Solid | 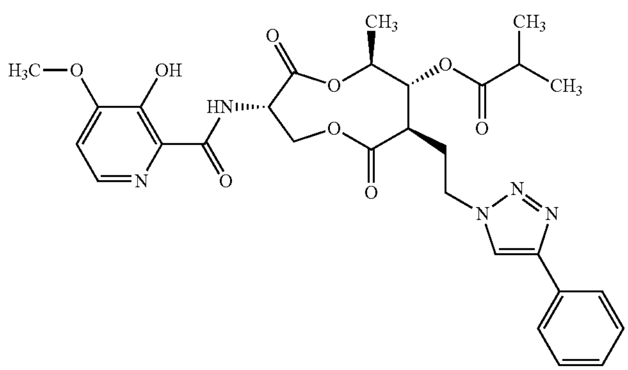 [SMILES: COc1ccnc(C(=O)N[C@H]2COC(=O)[C@H](CCn3cc(-c4ccccc4)nn3)[C@@H](OC(=O)C(C)C)[C@H](C)OC2=O)c1O] |
| 56 | White Solid | 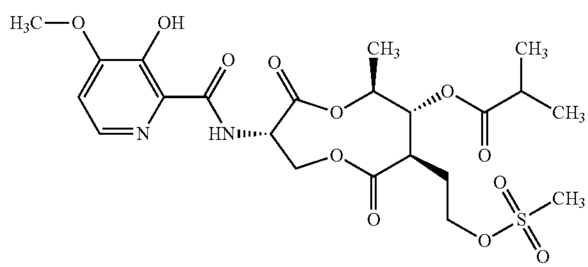 |
| 57 | White Solid | 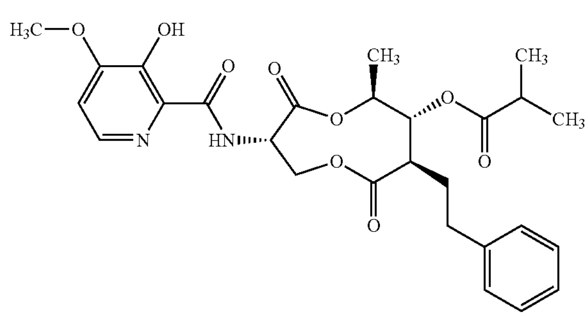 [SMILES: COc1ccnc(C(=O)N[C@H]2COC(=O)[C@H](CCc3ccccc3)[C@@H](OC(=O)C(C)C)[C@H](C)OC2=O)c1O] |

TABLE 1-continued
Compound Structure and Appearance
| Compound Number | Appearance | Structure |
|---|---|---|
| 58 | White Solid | 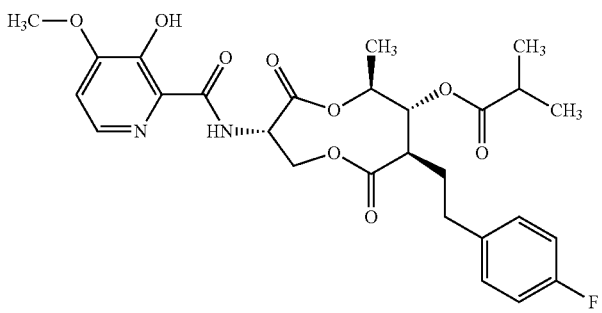 [SMILES: COc1ccnc(C(=O)N[C@H]2COC(=O)[C@H](CCc3ccc(F)cc3)[C@@H](OC(=O)C(C)C)[C@H](C)OC2=O)c1O] |
| 59 | Glassy Solid | 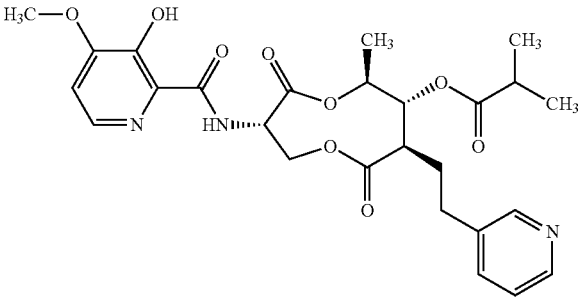 [SMILES: COc1ccnc(C(=O)N[C@H]2COC(=O)[C@H](CCc3cccnc3)[C@@H](OC(=O)C(C)C)[C@H](C)OC2=O)c1O] |
| 60 | White Solid | 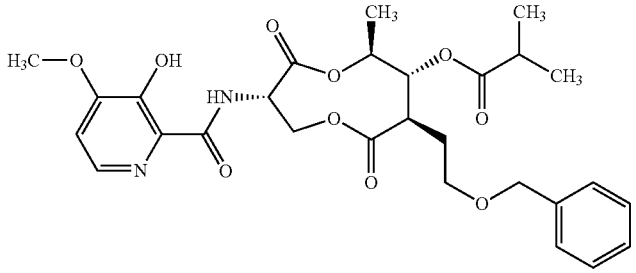 [SMILES: COc1ccnc(C(=O)N[C@H]2COC(=O)[C@H](CCOCc3ccccc3)[C@@H](OC(=O)C(C)C)[C@H](C)OC2=O)c1O] |
| 61 | White Solid | 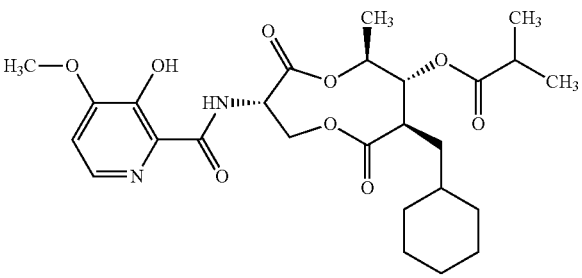 [SMILES: COc1ccnc(C(=O)N[C@H]2COC(=O)[C@H](CC3CCCCC3)[C@@H](OC(=O)C(C)C)[C@H](C)OC2=O)c1O] |
| 62 | White Solid | 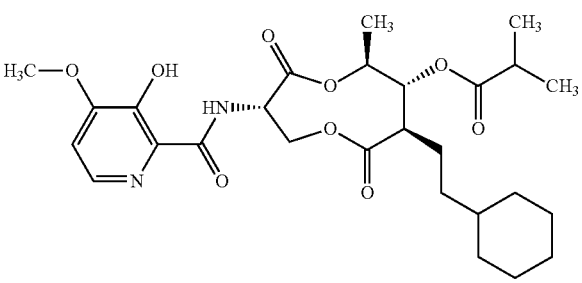 [SMILES: COc1ccnc(C(=O)N[C@H]2COC(=O)[C@H](CCC3CCCCC3)[C@@H](OC(=O)C(C)C)[C@H](C)OC2=O)c1O] |

TABLE 1-continued
Compound Structure and Appearance
| Compound Number | Appearance | Structure |
|---|---|---|
| 63 | White Solid | 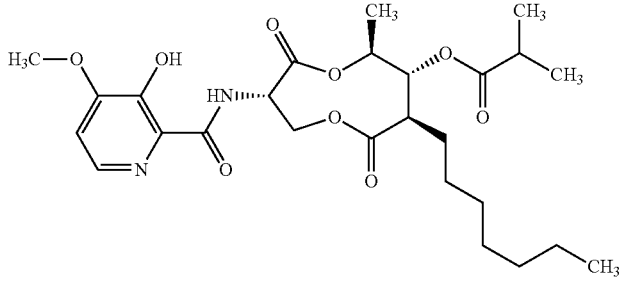 [SMILES: CCCCCCC[C@H]1C(=O)OC[C@H](NC(=O)c2nccc(OC)c2O)C(=O)O[C@@H](C)[C@@H]1OC(=O)C(C)C] |
| 64 | White Solid | 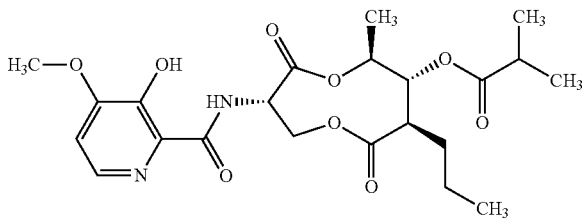 |
| 65 | White Solid | 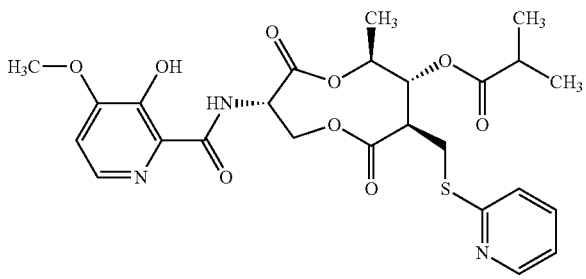 [SMILES: COc1ccnc(C(=O)N[C@H]2COC(=O)[C@H](CSc3ccccn3)[C@@H](OC(=O)C(C)C)[C@H](C)OC2=O)c1O] |
| 66 | White Solid | 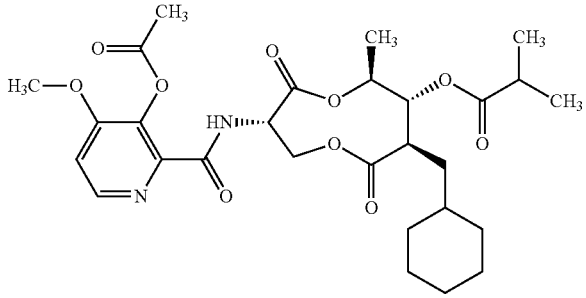 [SMILES: COc1ccnc(C(=O)N[C@H]2COC(=O)[C@H](CC3CCCCC3)[C@@H](OC(=O)C(C)C)[C@H](C)OC2=O)c1OC(C)=O] |
| 67 | White Solid | 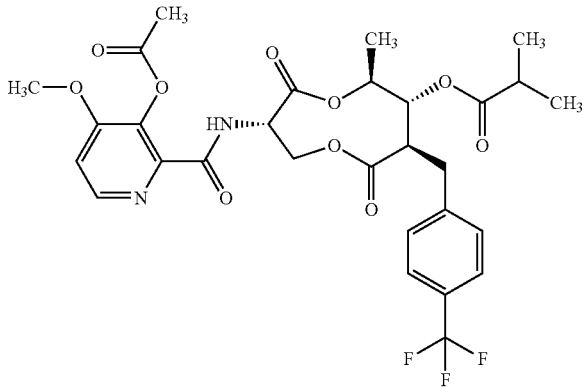 [SMILES: COc1ccnc(C(=O)N[C@H]2COC(=O)[C@H](Cc3ccc(C(F)(F)F)cc3)[C@@H](OC(=O)C(C)C)[C@H](C)OC2=O)c1OC(C)=O] |

TABLE 1-continued

Compound Structure and Appearance

| Compound Number | Appearance | Structure |
|---|---|---|
| 68 | White Solid | 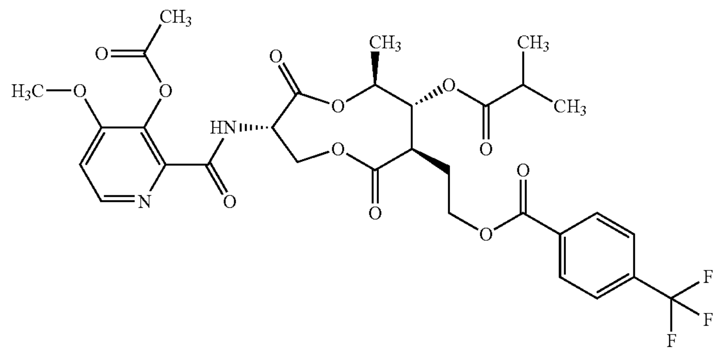 [SMILES: COc1ccnc(C(=O)N[C@H]2COC(=O)[C@H](CCOC(=O)c3ccc(C(F)(F)F)cc3)[C@@H](OC(=O)C(C)C)[C@H](C)OC2=O)c1OC(C)=O] |
| 69 | White Solid | 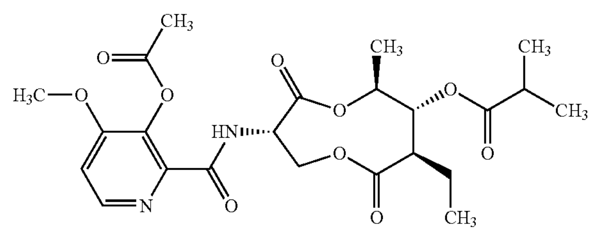 [SMILES: CC[C@H]1C(=O)OC[C@H](NC(=O)c2nccc(OC)c2OC(C)=O)C(=O)O[C@@H](C)[C@@H]1OC(=O)C(C)C] |
| 70 | White Solid | 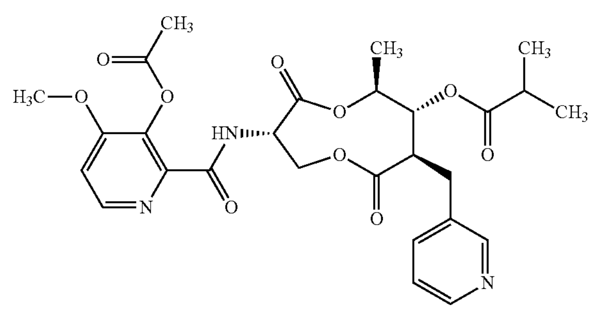 [SMILES: COc1ccnc(C(=O)N[C@H]2COC(=O)[C@H](Cc3cccnc3)[C@@H](OC(=O)C(C)C)[C@H](C)OC2=O)c1OC(C)=O] |

TABLE 2

Analytical Data

| Compound Number | MP (°C.) | IR (cm$^{-1}$) | MASS | $^1$H NMR* | $^{13}$C NMR* |
|---|---|---|---|---|---|
| 1 | 208-210 | — | ESIMS m/z 532.9 ([M + H]$^+$) | $^1$H NMR (CDCl$_3$) δ 11.77 (s, 1H), 8.59 (d, J = 8.2 Hz, 1H), 7.99 (d, J = 5.2 Hz, 1H), 7.17-7.04 (m, 2H), 6.95 (dd, J = 12.0, 5.3 Hz, 2H), 6.88 (d, J = 5.2 Hz, 1H), 5.33 (m, 1H), 5.20 (m, 2H), 4.98 (m, 1H), 3.94 (s, 3H), 3.63 (m, 1H), 2.92 (m, 2H), 2.74-2.57 (m, 2H), 1.32 (d, J = 6.3 Hz, 3H), 1.25 (m, 6H) | — |
| 2 | 148-155 | — | ESIMS m/z 516.0 ([M + H]$^+$) | $^1$H NMR (DMSO-d$_6$) δ 9.52 (d, J = 6.9 Hz, 1H), 8.47-8.35 (m, 2H), 8.09 (d, J = 5.2 Hz, 1H), 7.62 (d, J = 7.9 Hz, 1H), 7.31 (dd, J = 7.8, 4.8 Hz, 1H), 7.23 (d, J = 5.3 Hz, 1H), 5.09-4.79 (m, | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 4H), 4.34 (m, 1H), 3.89 (s, 3H), 3.21 (m, 1H), 2.83-2.59 (m, 3H), 1.24 (d, J = 6.2 Hz, 3H), 1.17 (d, J = 7.0 Hz, 6H) | |
| 3 | 92-95 | — | ESIMS m/z 516.9 ([M + H]$^+$) | $^1$H NMR (CDCl$_3$) δ 11.81 (s, 1H), 8.63 (d, J = 8.1 Hz, 1H), 8.51 (m, 1H), 8.01 (d, J = 5.2 Hz, 1H), 7.58 (td, J = 7.6, 1.8 Hz, 1H), 7.19-7.06 (m, 2H), 6.89 (d, J = 5.2 Hz, 1H), 5.46-5.10 (m, 3H), 5.02 (m, 1H), 3.95 (s, 3H), 3.71 (m, 1H), 3.48-3.31 (m, 1H), 3.23 (dd, J = 14.4, 11.4 Hz, 1H), 2.90 (dd, J = 14.4, 3.5 Hz, 1H), 2.62 (m, 1H), 1.35 (d, J = 6.3 Hz, 3H), 1.23 (d, J = 7.1 Hz, 6H) | — |
| 4 | 175-179 | — | ESIMS m/z 528.9 ([M + H]$^+$) | $^1$H NMR (CDCl$_3$) δ 11.79 (s, 1H), 8.59 (d, J = 8.1 Hz, 1H), 7.99 (d, J = 5.2 Hz, 1H), 7.04 (dd, J = 21.3, 8.0 Hz, 4H), 6.88 (d, J = 5.2 Hz, 1H), 5.42-5.27 (m, 1H), 5.19 (m, 2H), 5.08-4.87 (m, 1H), 3.94 (s, 3H), 3.62 (m, 1H), 2.93 (m, 2H), 2.76-2.55 (m, 2H), 1.32 (d, J = 6.3 Hz, 3H), 1.24 (d, J = 7.0 Hz, 6H) | — |
| 5 | 151-156 | — | ESIMS m/z 517.6 ([M + H]$^+$) | $^1$H NMR (DMSO-d$_6$) δ 11.95 (s, 1H), 9.55 (s, 1H), 8.49 (d, J = 5.7 Hz, 2H), 8.22 (d, J = 7.7 Hz, 1H), 8.06 (s, 1H), 7.29 (d, J = 5.9 Hz, 2H), 7.22 (m, 1H), 6.98 (d, J = 7.7 Hz, 1H), 5.07-4.80 (m, 4H), 4.32 (m, 1H), 3.89 (s, 3H), 3.52-3.22 (m, 2H), 2.94-2.72 (m, 4H), 2.66 (m, 1H), 1.24 (d, J = 6.1 Hz, 3H), 1.15 (m, 6H) | — |
| 6 | 222-226 | — | ESIMS m/z 583.0 ([M + H]$^+$) | $^1$H NMR (CDCl$_3$) δ 11.76 (s, 1H), 8.59 (d, J = 8.1 Hz, 1H), 7.99 (d, J = 5.2 Hz, 1H), 7.52 (d, J = 8.1 Hz, 2H), 7.25 (d, J = 8.7 Hz, 2H), 6.88 (d, J = 5.2 Hz, 1H), 5.33 (m, 1H), 5.21 (m, 2H), 4.99 (m, 1H), 3.94 (s, 3H), 3.63 (m, 1H), 2.99 (m, 2H), 2.75 (d, J = 12.7 Hz, 1H), 2.63 (m, 1H), 1.33 (d, J = 6.3 Hz, 3H), 1.25 (d, J = 7.0 Hz, 6H) | — |
| 7 | 148-152 | — | ESIMS m/z 550.0 ([M + H]$^+$) | $^1$H NMR (CDCl$_3$) δ 11.78 (s, 1H), 8.64 (d, J = 6.3 Hz, 1H), 8.18 (d, J = 2.3 Hz, 1H), 8.00 (d, J = 5.2 Hz, 1H), 7.44 (dd, J = 8.2, 2.5 Hz, 1H), 7.29-7.20 (m, 1H), 6.89 (d, J = 5.3 Hz, 1H), 5.33 (m, 1H), 5.32-4.99 (m, 3H), 4.96 (m, 1H), 3.95 (s, 3H), | — |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 3.92-3.46 (m, 2H), 3.11-2.84 (m, 2H), 2.84-2.56 (m, 2H), 1.33 (d, J = 6.3 Hz, 3H), 1.25 (d, J = 7.0 Hz, 6H) | |
| 8 | — | — | ESIMS m/z 544.9 ([M + H]⁺) | ¹H NMR (CDCl₃) δ 11.86 (s, 1H), 8.72 (d, J = 7.5 Hz, 1H), 8.01 (d, J = 5.1 Hz, 1H), 7.06 (d, J = 8.6 Hz, 2H), 6.91 (d, J = 5.0 Hz, 1H), 6.85-6.75 (m, 2H), 5.36 (m, 1H), 5.21 (m, 2H), 4.99 (m, 1H), 3.97 (s, 3H), 3.78 (s, 3H), 3.66 (m, 1H), 2.91 (m, 2H), 2.65 (m, 2H), 1.34 (d, J = 6.3 Hz, 3H), 1.26 (m, 6H) | — |
| 9 | 192-194 | — | ESIMS m/z 551.0 ([M + H]⁺) | ¹H NMR (CDCl₃) δ 11.77 (s, 1H), 8.61 (d, J = 8.1 Hz, 1H), 8.01 (d, J = 3.1 Hz, 1H), 7.26 (m, 2H), 7.16-7.03 (m, 2H), 6.89 (d, J = 5.1 Hz, 1H), 5.34 (m, 1H), 5.21 (m, 2H), 5.10-4.68 (m, 1H), 3.96 (s, 3H), 3.81-3.56 (m, 1H), 3.21-2.76 (m, 2H), 2.76-2.52 (m, 2H), 1.34 (d, J = 6.3 Hz, 3H), 1.26 (d, J = 6.9 Hz, 6H) | — |
| 10 | 184-185 | — | ESIMS m/z 550.9 ([M + H]⁺) | ¹H NMR (CDCl₃) δ 11.77 (s, 1H), 8.59 (d, J = 8.1 Hz, 1H), 7.99 (d, J = 5.2 Hz, 1H), 7.12 (m, 1H), 6.88 (d, J = 5.2 Hz, 1H), 6.84-6.70 (m, 2H), 5.33 (m, 1H), 5.19 (m, 2H), 5.08-4.89 (m, 1H), 3.94 (s, 3H), 3.67-3.57 (m, 1H), 3.02-2.72 (m, 3H), 2.66 (m, 1H), 1.33 (d, J = 6.3 Hz, 3H), 1.25 (m, 6H) | — |
| 11 | 186-191 | — | ESIMS m/z 564.8 ([M + H]⁺) | ¹H NMR (CDCl₃) δ 11.76 (s, 1H), 8.64 (d, J = 8.2 Hz, 1H), 8.02 (d, J = 5.2 Hz, 1H), 6.90 (d, J = 5.2 Hz, 1H), 5.49 (m, 1H), 5.22 (m, 1H), 5.04 (t, J = 9.8 Hz, 1H), 4.99-4.80 (m, 1H), 3.96 (s, 3H), 3.87 (m, 1H), 3.34 (dd, J = 11.8, 9.6 Hz, 1H), 3.16-2.97 (m, 2H), 2.64 (m, 1H), 1.30 (d, J = 6.2 Hz, 3H), 1.23 (d, J = 7.0 Hz, 6H) | — |
| 12 | 214-216 | — | ESIMS m/z 591.0 ([M + H]⁺) | ¹H NMR (CDCl₃) δ 11.79 (s, 1H), 8.60 (d, J = 8.1 Hz, 1H), 7.99 (d, J = 5.2 Hz, 1H), 7.58-7.53 (m, 2H), 7.52-7.47 (m, 2H), 7.42 (dd, J = 10.4, 4.8 Hz, 2H), 7.32 (m, 1H), 7.20 (d, J = 8.2 Hz, 2H), 6.87 (d, J = 5.3 Hz, 1H), 5.36 (m, 1H), 5.31-5.10 (m, 2H), 5.00 (m, 1H), 3.94 (s, 3H), 3.63 (m, 1H), 3.10-2.88 (m, 2H), 2.75 (d, J = 12.0 Hz, 1H), 2.64 (m, 1H), | — |

TABLE 2-continued

Analytical Data

| Compound Number | MP (° C.) | IR (cm⁻¹) | MASS | ¹H NMR* | ¹³C NMR* |
|---|---|---|---|---|---|
| 13 | 182-186 | — | ESIMS m/z 591.0 ([M + H]⁺) | ¹H NMR (CDCl₃) δ 11.78 (s, 1H), 8.60 (d, J = 8.1 Hz, 1H), 7.99 (d, J = 5.2 Hz, 1H), 7.61-7.51 (m, 2H), 7.43 (m, 3H), 7.40-7.29 (m, 3H), 7.12 (d, J = 7.6 Hz, 1H), 6.87 (d, J = 5.2 Hz, 1H), 5.35 (m, 1H), 5.24 (m, 2H), 5.00 (m, 1H), 3.94 (s, 3H), 3.63 (m, 1H), 3.14-2.95 (m, 2H), 2.78 (m, 1H), 2.64 (m, 1H), 1.34 (d, J = 6.3 Hz, 3H), 1.24 (d, J = 7.0 Hz, 6H) | — |
| 14 | 169-175 | — | ESIMS m/z 517.0 ([M + H]⁺) | ¹H NMR (CDCl₃) δ 9.21-8.53 (m, 4H), 8.04 (d, J = 5.2 Hz, 1H), 7.18 (d, J = 5.3 Hz, 1H), 5.40-5.23 (m, 1H), 5.16 (m, 2H), 5.08-4.87 (m, 1H), 4.20-4.06 (m, 1H), 3.96 (s, 3H), 3.35-3.17 (m, 1H), 2.94 (m, 2H), 2.86-2.66 (m, 1H), 1.35 (d, J = 6.3 Hz, 3H), 1.26 (d, J = 7.0 Hz, 6H) | — |
| 15 | 192-197 | — | ESIMS m/z 564.9 ([M + H]⁺) | ¹H NMR (CDCl₃) δ 11.78 (s, 1H), 8.55 (d, J = 8.0 Hz, 1H), 7.96 (d, J = 5.2 Hz, 1H), 7.92 (d, J = 8.2 Hz, 1H), 7.85 (d, J = 7.9 Hz, 1H), 7.73 (d, J = 8.0 Hz, 1H), 7.59-7.44 (m, 2H), 7.41-7.29 (m, 2H), 6.86 (d, J = 5.2 Hz, 1H), 5.44-5.23 (m, 2H), 5.18 (m, 1H), 5.02 (m, 1H), 3.93 (s, 3H), 3.59-3.46 (m, 1H), 3.45-3.24 (m, 2H), 3.17 (m, 1H), 2.81-2.70 (m, 1H), 1.37 (d, J = 6.3 Hz, 3H), 1.32 (d, J = 6.6 Hz, 6H) | — |
| 16 | 188-190 | — | ESIMS m/z 584.3 ([M + H]⁺) | ¹H NMR (CDCl₃) δ 11.77 (s, 1H), 8.60 (d, J = 8.1 Hz, 1H), 7.99 (d, J = 5.2 Hz, 1H), 7.48-7.34 (m, 4H), 6.88 (d, J = 5.2 Hz, 1H), 5.34 (m, 1H), 5.28-5.10 (m, 2H), 4.99 (dq, J = 12.4, 6.2 Hz, 1H), 3.94 (s, 3H), 3.69-3.57 (m, 1H), 3.13-3.00 (m, 1H), 3.00-2.90 (m, 1H), 2.75 (d, J = 12.2 Hz, 1H), 2.64 (m, 1H), 1.34 (d, J = 6.3 Hz, 3H), 1.25 (d, J = 7.0 Hz, 6H) | — |
| 17 | 161-165 | — | ESIMS m/z 465.6 ([M + H]⁺) | ¹H NMR (CDCl₃) δ 11.80 (s, 1H), 8.65 (d, J = 8.2 Hz, 1H), 8.01 (d, J = 5.2 Hz, 1H), 6.89 (d, J = 5.2 Hz, 1H), 5.68 (ddt, J = 17.1, 10.2, 6.7 Hz, 1H), 5.46 (m, 1H), 5.20 (dd, J = 14.8, 7.7 Hz, 1H), 5.16-5.01 (m, 3H), 5.01-4.90 (m, | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 1H), 3.95 (s, 3H), 3.78 (m, 1H), 2.76-2.54 (m, 2H), 2.53-2.40 (m, 1H), 2.14 (m, 1H), 1.30 (d, J = 6.3 Hz, 3H), 1.22 (d, J = 7.0 Hz, 6H) | |
| 18 | 146-148 | — | ESIMS m/z 521.4 ([M + H]$^+$) | $^1$H NMR (CDCl$_3$) δ 11.81 (s, 1H), 8.65 (d, J = 8.1 Hz, 1H), 8.01 (d, J = 5.2 Hz, 1H), 6.89 (d, J = 5.2 Hz, 1H), 5.47 (m, 2H), 5.23 (m, 2H), 5.10 (dd, J = 11.9, 7.9 Hz, 1H), 5.00-4.88 (m, 1H), 3.95 (s, 3H), 3.74 (m, 1H), 2.70-2.56 (m, 2H), 2.48-2.31 (m, 1H), 2.06 (m, 1H), 1.95 (q, J = 6.6 Hz, 2H), 1.37-1.24 (m, 7H), 1.23-1.19 (m, 6H), 0.86 (t, J = 7.1 Hz, 3H) | — |
| 19 | 48-50 | — | ESIMS m/z 673 ([M + H]$^+$) | $^1$H NMR (300 MHz, CDCl$_3$) δ 8.55 (d, J = 7.9 Hz, 1H), 8.26 (d, J = 5.5 Hz, 1H), 8.04-7.87 (m, 2H), 7.55 (t, J = 7.4 Hz, 1H), 7.43 (t, J = 7.5 Hz, 2H), 6.95 (d, J = 5.4 Hz, 1H), 5.85-5.62 (m, 2H), 5.41 (s, 1H), 5.26-5.06 (m, 2H), 4.94 (dd, J = 9.8, 6.3 Hz, 1H), 4.42-4.19 (m, 2H), 3.92 (d, J = 14.3 Hz, 3H), 3.65 (s, 1H), 2.76 (t, J = 9.5 Hz, 1H), 2.62 (dt, J = 10.8, 5.5 Hz, 1H), 2.58-2.47 (m, 1H), 2.30 (s, 1H), 1.82 (s, 1H), 1.29 (d, J = 6.3 Hz, 3H), 1.21 (dd, J = 7.0, 0.9 Hz, 6H), 1.13 (d, J = 7.0 Hz, 6H) | — |
| 20 | — | — | ESIMS m/z 633.4 ([M + H]$^+$) | $^1$H NMR (CDCl$_3$) δ 8.53 (d, J = 7.9 Hz, 1H), 8.27 (d, J = 5.4 Hz, 1H), 7.09 (m, 2H), 6.95 (m, 3H), 5.74 (d, J = 1.1 Hz, 2H), 5.35 (m, 1H), 5.19 (m, 2H), 5.01-4.88 (m, 1H), 3.89 (s, 3H), 3.63 (m, 1H), 3.02-2.80 (m, 2H), 2.73-2.47 (m, 3H), 1.31 (d, J = 6.3 Hz, 3H), 1.26-1.18 (m, 6H), 1.13 (d, J = 7.0 Hz, 6H) | $^{13}$C NMR (CDCl$_3$) δ 176.33, 175.61, 171.67, 163.17, 160.25, 145.63, 144.40, 141.39, 133.57, 130.34, 130.26, 115.56, 115.35, 109.83, 89.68, 75.04, 74.41, 65.75, 56.20, 52.20, 50.39, 34.13, 33.86, 19.00, 18.68, 18.53, 17.85 |
| 21 | — | — | ESIMS m/z 651.5 ([M + H]$^+$) | $^1$H NMR (CDCl$_3$) δ 8.53 (d, J = 7.9 Hz, 1H), 8.28 (d, J = 5.2 Hz, 1H), 7.12 (m, 1H), 6.97 (d, J = 5.2 Hz, 1H), 6.82-6.69 (m, 2H), 5.74 (s, 2H), 5.34 (m, 1H), 5.19 (m, 2H), 5.02-4.88 (m, 1H), 3.90 (s, 3H), 3.60 (m, 1H), 2.98-2.74 (m, 3H), 2.65 (m, 1H), 2.54 (m, 1H), 1.31 (d, J = 6.3 Hz, | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 3H), 1.27-1.22 (m, 6H), 1.13 (d, J = 7.0 Hz, 6H) | |
| 22 | 131-133 | — | ESIMS m/z 629.6 ([M + H]$^+$) | $^1$H NMR (CDCl$_3$) δ 8.53 (d, J = 8.0 Hz, 1H), 8.26 (d, J = 5.4 Hz, 1H), 7.04 (dd, J = 20.7, 8.0 Hz, 4H), 6.95 (d, J = 5.4 Hz, 1H), 5.80-5.69 (m, 2H), 5.36 (m, 1H), 5.20 (m, 2H), 4.97 (m, 1H), 3.89 (s, 3H), 3.59 (m, 1H), 3.02-2.83 (m, 2H), 2.70-2.58 (m, 2H), 2.53 (m, 1H), 1.31 (d, J = 6.3 Hz, 3H), 1.24 (m, 6H), 1.13 (d, J = 7.0 Hz, 6H) | — |
| 23 | 171-174 | — | ESIMS m/z 638.1 ([M + Na]$^+$) | $^1$H NMR (CDCl$_3$) δ 8.53 (d, J = 8.0 Hz, 1H), 8.47 (d, J = 3.8 Hz, 1H), 8.41 (s, 1H), 8.27 (d, J = 5.4 Hz, 1H), 7.48 (d, J = 7.9 Hz, 1H), 7.21 (dd, J = 7.8, 4.9 Hz, 1H), 6.95 (d, J = 5.4 Hz, 1H), 5.80-5.65 (m, 2H), 5.35 (m, 1H), 5.20 (m, 2H), 5.04-4.90 (m, 1H), 3.89 (s, 3H), 3.61 (m, 1H), 3.07-2.83 (m, 2H), 2.75-2.59 (m, 2H), 2.53 (m, 1H), 1.32 (d, J = 6.3 Hz, 3H), 1.25 (m, 6H), 1.13 (d, J = 7.0 Hz, 6H) | — |
| 24 | 100-103 | — | ESIMS m/z 684.0 ([M + H]$^+$) | $^1$H NMR (CDCl$_3$) δ 8.53 (d, J = 7.9 Hz, 1H), 8.26 (d, J = 5.3 Hz, 1H), 7.52-7.29 (m, 4H), 6.95 (d, J = 5.4 Hz, 1H), 5.78-5.69 (m, 2H), 5.36 (m, 1H), 5.20 (m, 2H), 4.98 (m, 1H), 3.89 (s, 3H), 3.60 (m, 1H), 3.07 (t, J = 12.6 Hz, 1H), 2.99-2.87 (m, 1H), 2.83-2.70 (m, 1H), 2.63 (sept, J = 7.0 Hz, 1H), 2.54 (sept, J = 7.0 Hz, 1H), 1.32 (d, J = 6.3 Hz, 3H), 1.24 (d, J = 7.0 Hz, 6H), 1.13 (d, J = 7.0 Hz, 6H) | — |
| 25 | 55-68 | — | ESIMS m/z 691.4 ([M + H]$^+$) | $^1$H NMR (CDCl$_3$) δ 8.54 (d, J = 7.9 Hz, 1H), 8.26 (d, J = 5.3 Hz, 1H), 7.59-7.51 (m, 2H), 7.43 (m, 3H), 7.34 (m, 3H), 7.12 (d, J = 7.6 Hz, 1H), 6.95 (d, J = 5.4 Hz, 1H), 5.80-5.69 (m, 2H), 5.38 (m, 1H), 5.28-5.12 (m, 2H), 4.98 (m, 1H), 3.89 (s, 3H), 3.60 (m, 1H), 3.14-2.92 (m, 2H), 2.77 (d, J = 11.9 Hz, 1H), 2.63 (m, 1H), 2.53 (sept, J = 7.0 Hz, 1H), 1.32 (d, J = 6.3 Hz, 3H), 1.24 (d, J = 7.0 Hz, 6H), 1.13 (d, J = 7.0 Hz, 6H) | — |
| 26 | 68-69 | — | ESIMS m/z 637 ([M + H]$^+$) | $^1$H NMR (300 MHz, CDCl$_3$) δ 8.60 (d, J = 7.8 Hz, 1H), 8.28 (d, J = 5.3 Hz, 1H), 6.97 (d, J = 5.4 Hz, 1H), | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 5.83-5.67 (m, 2H), 5.48 (s, 1H), 5.19 (d, J = 7.6 Hz, 1H), 5.09 (t, J = 9.9 Hz, 1H), 4.94 (dq, J = 12.4, 6.1 Hz, 1H), 4.23-3.94 (m, 2H), 3.91 (s, 3H), 3.76 (s, 1H), 2.76-2.47 (m, 3H), 2.12 (dd, J = 15.7, 9.9 Hz, 1H), 1.65 (s, 1H), 1.60-1.46 (m, 1H), 1.29 (d, J = 6.1 Hz, 3H), 1.24-1.18 (m, 6H), 1.16 (t, J = 6.3 Hz, 6H), 1.02-0.91 (m, 2H), 0.91-0.79 (m, 2H) | |
| 27 | 117-119 | — | ESIMS m/z 621 ([M + H]$^+$) | $^1$H NMR (300 MHz, CDCl$_3$) δ 8.60 (d, J = 7.8 Hz, 1H), 8.29 (d, J = 5.4 Hz, 1H), 6.97 (d, J = 5.4 Hz, 1H), 5.82-5.73 (m, 2H), 5.49 (s, 1H), 5.19 (d, J = 6.2 Hz, 1H), 5.05 (t, J = 9.8 Hz, 1H), 4.93 (dd, J = 9.8, 6.2 Hz, 1H), 3.91 (s, 3H), 3.74 (s, 1H), 2.79-2.49 (m, 2H), 1.82-1.55 (m, 5H), 1.34-1.08 (m, 21H), 1.02-0.69 (m, 3H) | — |
| 28 | — | — | ESIMS m/z 583 ([M + H]$^+$) | $^1$H NMR (300 MHz, CDCl$_3$) δ 8.60 (d, J = 7.9 Hz, 1H), 8.29 (d, J = 5.3 Hz, 1H), 6.98 (d, J = 5.4 Hz, 1H), 5.82-5.70 (m, 2H), 5.47 (s, 1H), 5.28-5.14 (m, 1H), 5.08 (q, J = 9.9 Hz, 1H), 5.01-4.87 (m, 1H), 3.91 (s, 3H), 3.77 (s, 1H), 3.44-3.28 (m, 2H), 3.27 (s, 3H), 2.78 (ddd, J = 11.6, 10.5, 5.4 Hz, 1H), 2.68-2.48 (m, 2H), 2.04-1.91 (m, 1H), 1.64 (ddd, J = 9.6, 8.3, 5.5 Hz, 1H), 1.34-1.27 (m, 3H), 1.21 (d, J = 7.0 Hz, 6H), 1.15 (d, J = 7.1 Hz, 6H) | $^{13}$C NMR (75 MHz, CDCl$_3$) δ 176.47, 175.80, 172.67, 170.42, 163.39, 160.43, 145.83, 144.53, 110.04, 89.85, 75.18, 74.84, 70.05, 65.78, 58.80, 56.38, 50.66, 47.31, 34.25, 34.04, 28.80, 19.16, 19.08, 18.85, 18.01 |
| 29 | — | — | ESIMS m/z 659 ([M + H]$^+$) | $^1$H NMR (300 MHz, CDCl$_3$) δ 8.58 (d, J = 7.9 Hz, 1H), 8.28 (d, J = 5.4 Hz, 1H), 7.45-7.18 (m, 5H), 6.96 (d, J = 5.4 Hz, 1H), 5.88-5.70 (m, 2H), 5.42 (s, 1H), 5.26-5.14 (m, 1H), 5.10 (t, J = 9.9 Hz, 1H), 5.00-4.83 (m, 1H), 4.43 (s, 2H), 3.90 (s, 3H), 3.69 (s, 1H), 3.43 (qd, J = 9.7, 4.4 Hz, 2H), 2.91-2.73 (m, 1H), 2.68-2.48 (m, 2H), 2.04 (m, 1H), 1.64 (m, 1H), 1.28 (d, J = 6.2 Hz, 3H), 1.20 (d, J = 7.0 Hz, 6H), 1.14 (d, J = 7.0 Hz, 6H) | $^{13}$C NMR (75 MHz, CDCl$_3$) δ 176.46, 175.82, 172.58, 170.51, 163.37, 160.45, 145.81, 144.59, 141.70, 138.31, 128.50, 127.75, 110.02, 89.90, 75.22, 74.90, 73.09, 67.68, 65.65, 56.38, 50.60, 47.53, 34.26, 34.06, 28.97, 19.18, 18.87, 18.02, 14.40 |
| 30 | — | — | ESIMS m/z 639 ([M + H]$^+$) | $^1$H NMR (300 MHz, CDCl$_3$) δ 8.57 (d, J = 8.0 Hz, 1H), 8.28 (d, J = 5.4 Hz, 1H), 6.97 (d, J = 5.4 Hz, 1H), | $^{13}$C NMR (75 MHz, CDCl$_3$) δ 176.43, 175.66, 172.14, 170.61, 170.40, 163.37, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 5.80-5.69 (m, 2H), 5.44 (s, 1H), 5.20 (dd, J = 15.3, 8.2 Hz, 1H), 5.04 (t, J = 9.7 Hz, 1H), 4.99-4.83 (m, 1H), 3.90 (s, 3H), 3.81 (s, 1H), 2.97 (ddd, J = 12.7, 9.8, 3.1 Hz, 1H), 2.80 (dd, J = 16.9, 11.7 Hz, 1H), 2.71-2.47 (m, 2H), 2.28 (dd, J = 16.8, 3.1 Hz, 1H), 1.41 (s, 9H), 1.29 (d, J = 6.1 Hz, 3H), 1.22 (dd, J = 7.0, 1.0 Hz, 6H), 1.14 (d, J = 7.0 Hz, 6H) | 160.44, 145.78, 144.57, 141.62, 110.03, 89.86, 81.82, 74.67, 74.39, 65.60, 56.37, 50.42, 46.07, 35.15, 34.20, 34.03, 28.15, 19.13, 19.02, 18.84, 17.97 |
| 31 | — | (Thin Film) 3367, 2975, 2938, 1754, 1683, 1506, 1470, 1182, 1140, 1094 | ESIMS m/z 630 ([M + H]$^+$) | $^1$H NMR (300 MHz, CDCl$_3$) δ 8.60 (d, J = 7.9 Hz, 1H), 8.51-8.43 (m, 1H), 8.42-8.36 (m, 1H), 8.29 (d, J = 5.4 Hz, 1H), 7.45 (d, J = 7.7 Hz, 1H), 7.26-7.16 (m, 1H), 6.97 (d, J = 5.4 Hz, 1H), 5.82-5.71 (m, 2H), 5.50 (s, 1H), 5.20 (d, J = 7.3 Hz, 1H), 5.10 (t, J = 9.9 Hz, 1H), 4.94-4.83 (m, 1H), 3.91 (s, 3H), 3.78 (s, 1H), 2.92 (dd, J = 14.3, 6.8 Hz, 1H), 2.70-2.43 (m, 4H), 2.10 (s, 1H), 1.64 (s, 1H), 1.37 (dd, J = 6.9, 2.1 Hz, 3H), 1.27 (d, J = 6.3 Hz, 6H), 1.17 (dd, J = 11.0, 4.1 Hz, 6H) | — |
| 32 | — | — | ESIMS m/z 629 ([M + H]$^+$) | $^1$H NMR (300 MHz, CDCl$_3$) δ 8.60 (d, J = 7.9 Hz, 1H), 8.28 (d, J = 5.1 Hz, 1H), 7.34-7.23 (m, 2H), 7.23-7.15 (m, 1H), 7.14-7.06 (m, 2H), 6.97 (d, J = 5.3 Hz, 1H), 5.84-5.70 (m, 2H), 5.50 (s, 1H), 5.27-5.15 (m, 1H), 5.09 (t, J = 9.9 Hz, 1H), 4.96-4.82 (m, 1H), 3.90 (s, 3H), 3.82 (d, J = 16.2 Hz, 1H), 2.75-2.49 (m, 4H), 2.49-2.35 (m, 1H), 2.21-2.06 (m, 1H), 1.65 (dd, J = 17.4, 12.5 Hz, 1H), 1.26 (d, J = 6.3 Hz, 3H), 1.16 (t, J = 7.1 Hz, 12H) | $^{13}$C NMR (75 MHz, CDCl$_3$) δ 176.47, 175.67, 172.61, 170.45, 163.40, 160.44, 145.81, 141.69, 140.90, 128.60, 126.32, 110.04, 106.32, 89.88, 75.27, 74.80, 65.76, 56.39, 50.61, 49.54, 34.27, 34.06, 33.36, 30.46, 19.13, 19.07, 18.87, 17.98 |
| 33 | — | (Neat) 3367, 1752, 1682, 1505, 1140 | ESIMS m/z 623.5 ([M + H]$^+$) | $^1$H NMR (CDCl$_3$) δ 8.60 (d, J = 7.9 Hz, 1H), 8.29 (d, J = 5.4 Hz, 1H), 6.97 (d, J = 5.4 Hz, 1H), 5.76 (q, J = 6.4 Hz, 2H), 5.49 (m, 1H), 5.18 (m, 1H), 5.13-5.02 (m, 1H), 4.92 (dq, J = 12.5, 6.2 Hz, 1H), 3.90 (s, 3H), 3.72 (m, 1H), 2.68-2.49 (m, 3H), 1.72 (dd, J = 20.5, 10.1 Hz, 1H), 1.36-1.17 (m, 21H), 1.15 (d, J = 7.0 Hz, 6H), 0.86 (t, J = 6.8 Hz, 3H) | — |
| 34 | — | — | ESIMS m/z 567.5 ([M + H]$^+$) | $^1$H NMR (CDCl$_3$) δ 8.60 (d, J = 7.9 Hz, 1H), 8.29 (d, J = 5.4 Hz, 1H), | $^{13}$C NMR (CDCl$_3$) δ 176.34, 175.58, |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 6.97 (d, J = 5.4 Hz, 1H), 5.76 (q, J = 6.4 Hz, 2H), 5.48 (br s, 1H) 5.19 (m, 1H), 5.13-5.03 (m, 1H), 4.92 (dq, J = 12.5, 6.1 Hz, 1H), 3.90 (s, 3H), 3.73 (br s, 1H), 2.68-2.47 (m, 3H), 1.81-1.58 (m, 3H), 1.28 (d, J = 6.2 Hz, 4H), 1.21 (dd, J = 7.0, 1.7 Hz, 6H), 1.15 (d, J = 7.0 Hz, 6H), 0.88 (t, J = 7.1 Hz, 3H) | 172.71, 170.30, 163.18, 160.23, 145.63, 144.38, 141.45, 109.82, 89.68, 77.23, 75.23, 74.63, 56.19, 50.49, 34.10, 33.86, 30.51, 20.33, 18.95, 18.67, 17.80, 13.81 |
| 35 | 172-174 | — | ESIMS m/z 522 ([M + H]$^+$) | $^1$H NMR (300 MHz, CDCl$_3$) δ 11.78 (d, J = 0.5 Hz, 1H), 8.61 (d, J = 8.2 Hz, 1H), 8.07-7.87 (m, 3H), 7.65-7.53 (m, 1H), 7.50-7.39 (m, 2H), 6.88 (d, J = 5.1 Hz, 1H), 5.40 (s, 1H), 5.27-5.08 (m, 2H), 4.96 (dq, J = 12.5, 6.3 Hz, 1H), 4.42-4.20 (m, 2H), 3.95 (s, 3H), 3.64 (s, 1H), 2.86-2.72 (m, 1H), 2.63 (dt, J = 14.0, 7.0 Hz, 1H), 2.37-2.22 (m, 1H), 1.81 (s, 1H), 1.31 (d, J = 6.3 Hz, 3H), 1.22 (dd, J = 7.0, 1.2 Hz, 6H) | — |
| 36 | — | — | ESIMS m/z 540 ([M + H]$^+$) | $^1$H NMR (CDCl$_3$) δ 11.78 (s, 1H), 8.66 (d, J = 8.1 Hz, 1H), 8.01 (d, J = 5.2 Hz, 1H), 6.90 (d, J = 5.2 Hz, 1H), 5.47 (s, 1H), 5.29-5.16 (m, J = 7.2 Hz, 1H), 5.10 (td, J = 9.9, 4.6 Hz, 1H), 5.01-4.89 (m, 1H), 4.19-3.99 (m, 2H), 3.95 (s, 3H), 3.77 (s, 1H), 2.78-2.67 (m, 1H), 2.67-2.57 (m, J = 13.9, 7.0 Hz, 1H), 2.56-2.44 (m, 1H), 2.22-2.06 (m, 1H), 1.79-1.61 (m, 1H), 1.31 (d, J = 6.3 Hz, 3H), 1.22 (dd, J = 7.0, 0.8 Hz, 6H), 1.13 (dd, J = 7.0, 0.8 Hz, 6H) | $^{13}$C NMR (CDCl$_3$) δ 176.76, 175.58, 171.94, 169.75, 169.03, 155.45, 148.85, 140.76, 129.91, 109.76, 74.90, 74.69, 65.11, 61.91, 56.14, 49.84, 47.15, 34.07, 33.90, 29.70, 27.80, 18.91, 18.85, 18.83, 17.82 |
| 37 | — | — | ESIMS m/z 553 ([M + H]$^+$) | $^1$H NMR (CDCl$_3$) δ 11.78 (s, 1H), 8.65 (d, J = 8.2 Hz, 1H), 8.01 (d, J = 5.2 Hz, 1H), 6.90 (d, J = 5.2 Hz, 1H), 5.55-5.40 (m, 1H), 5.28-5.15 (m, 1H), 5.10 (td, J = 9.9, 5.2 Hz, 1H), 5.00-4.91 (m, 1H), 4.02 (t, J = 6.2 Hz, 2H), 3.95 (s, 3H), 3.76 (s, 1H), 2.76-2.67 (m, 1H), 2.62 (dq, J = 14.0, 7.0 Hz, 1H), 2.24-2.00 (m, 1H), 1.72 (m, 1H), 1.31 (d, J = 6.3 Hz, 3H), 1.22 (dd, J = 7.0, 1.1 Hz, 6H), 1.16 (s, 9H) | $^{13}$C NMR (CDCl$_3$) δ 178.25, 175.59, 171.86, 169.77, 169.02, 155.45, 148.85, 140.77, 129.91, 109.76, 74.91, 74.70, 65.09, 62.19, 56.14, 49.80, 47.27, 38.71, 34.08, 29.70, 27.80, 27.05, 18.92, 18.89, 17.82 |
| 38 | 157-159 | — | ESIMS m/z 537 ([M + H]$^+$) | $^1$H NMR (300 MHz, CDCl$_3$) δ 11.79 (s, 1H), 8.65 (d, J = 8.2 Hz, 1H), 8.01 (d, J = 5.2 Hz, 1H), 6.89 (d, J = 5.2 Hz, 1H), | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 5.48 (s, 1H), 5.21 (d, J = 7.3 Hz, 1H), 5.10 (t, J = 9.9 Hz, 1H), 5.04-4.89 (m, 1H), 4.22-4.06 (m, 1H), 4.06-3.99 (m, 1H), 3.95 (s, 3H), 3.78 (s, 1H), 2.79-2.67 (m, 1H), 2.63 (dt, J = 14.0, 7.0 Hz, 1H), 2.13 (s, 1H), 1.71 (s, 1H), 1.54 (m, 1H), 1.30 (d, J = 6.2 Hz, 3H), 1.22 (dd, J = 7.0, 0.5 Hz, 6H), 1.02-0.92 (m, 2H), 0.89-0.80 (m, 2H) | |
| 39 | 159-161 | — | ESIMS m/z 617 ([M + H]$^+$) | $^1$H NMR (CDCl$_3$) δ 11.78 (s, 1H), 8.62 (d, J = 8.2 Hz, 1H), 8.00 (d, J = 5.2 Hz, 1H), 7.58 (dd, J = 8.2, 1.6 Hz, 1H), 7.39 (d, J = 1.5 Hz, 1H), 6.89 (d, J = 5.2 Hz, 1H), 6.84 (d, J = 8.2 Hz, 1H), 6.04 (s, 2H), 5.42 (s, 1H), 5.21 (d, J = 6.9 Hz, 1H), 5.13 (t, J = 9.9 Hz, 1H), 4.96 (dq, J = 12.4, 6.2 Hz, 1H), 4.35-4.18 (m, 2H), 3.95 (s, 3H), 3.68 (s, 1H), 2.76 (t, J = 9.6 Hz, 1H), 2.63 (dt, J = 14.0, 7.0 Hz, 1H), 2.28 (d, J = 6.7 Hz, 1H), 1.86-1.73 (m, 1H), 1.31 (d, J = 6.3 Hz, 3H), 1.22 (dd, J = 7.0, 1.1 Hz, 6H) | — |
| 40 | 178-179 | — | ESIMS m/z 649 ([M + H]$^+$) | $^1$H NMR (CDCl$_3$) δ 11.77 (s, 1H), 8.61 (d, J = 8.2 Hz, 1H), 8.07-8.01 (m, 2H), 7.99 (d, J = 5.2 Hz, 1H), 7.70-7.65 (m, 2H), 7.65-7.60 (m, 2H), 7.51-7.44 (m, 2H), 7.42-7.36 (m, 1H), 6.88 (d, J = 5.2 Hz, 1H), 5.43 (s, 1H), 5.28-5.10 (m, 2H), 4.97 (dq, J = 12.6, 6.2 Hz, 1H), 4.37 (ddd, J = 11.9, 7.0, 5.2 Hz, 1H), 4.28 (dt, J = 14.8, 6.2 Hz, 1H), 3.94 (s, 3H), 3.67 (s, 1H), 2.87-2.74 (m, 1H), 2.70-2.57 (m, 1H), 2.41-2.24 (m, 1H), 1.91-1.76 (m, 1H), 1.32 (d, J = 6.3 Hz, 3H), 1.23 (dd, J = 7.0, 2.2 Hz, 6H) | — |
| 41 | — | — | ESIMS m/z 663 ([M + H]$^+$) | $^1$H NMR (CDCl$_3$) δ 11.76 (s, 1H), 8.62 (d, J = 8.1 Hz, 1H), 8.00 (d, J = 5.2 Hz, 1H), 7.25 (s, 2H), 6.89 (d, J = 5.2 Hz, 1H), 5.38 (s, 1H), 5.25-5.09 (m, 2H), 4.98 (dq, J = 12.5, 6.3 Hz, 1H), 4.34 (ddd, J = 12.1, 7.0, 5.5 Hz, 1H), 4.30-4.20 (m, 1H), 3.94 (s, 3H), 3.92 (s, 6H), 3.91 (s, 3H), 3.75-3.60 (m, 1H), 2.79-2.69 (m, 1H), 2.68-2.59 (m, | — |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 1H), 2.37-2.24 (m, 1H), 1.87-1.72 (m, 1H), 1.31 (d, J = 6.3 Hz, 3H), 1.23 (dd, J = 7.0, 1.8 Hz, 6H) | |
| 42 | 160-162 | — | ESIMS m/z 641 ([M + H]⁺) | ¹H NMR (CDCl₃) δ 11.84-11.70 (m, 1H), 8.63 (d, J = 8.2 Hz, 1H), 8.09 (d, J = 8.1 Hz, 2H), 8.00 (d, J = 5.2 Hz, 1H), 7.72 (d, J = 8.2 Hz, 2H), 6.89 (d, J = 5.2 Hz, 1H), 5.41 (s, 1H), 5.28-5.10 (m, 2H), 5.03-4.91 (m, 1H), 4.45-4.24 (m, 2H), 3.95 (s, 3H), 3.70 (s, 1H), 2.78 (td, J = 11.5, 2.5 Hz, 1H), 2.64 (hept, J = 7.0 Hz, 1H), 2.32 (ddd, J = 17.8, 11.5, 5.2 Hz, 1H), 1.91-1.79 (m, 1H), 1.32 (dd, J = 6.2, 2.4 Hz, 3H), 1.22 (dd, J = 7.0, 1.1 Hz, 6H) | — |
| 43 | 167-168 | — | ESIMS m/z 663 ([M + H]⁺) | ¹H NMR (300 MHz, CDCl₃) δ 11.76 (s, 1H), 8.64 (d, J = 8.2 Hz, 1H), 7.99 (d, J = 5.2 Hz, 1H), 6.90 (d, J = 5.2 Hz, 1H), 5.44 (s, 1H), 5.21 (dd, J = 15.5, 8.1 Hz, 1H), 5.12 (t, J = 9.8 Hz, 1H), 4.96 (dq, J = 12.3, 6.1 Hz, 1H), 4.44 (dt, J = 10.6, 5.2 Hz, 1H), 4.36-4.21 (m, 1H), 3.95 (s, 3H), 3.75 (d, J = 25.0 Hz, 1H), 2.89-2.75 (m, 1H), 2.71-2.55 (m, 1H), 2.29-2.12 (m, 1H), 1.86 (d, J = 14.7 Hz, 1H), 1.32 (d, J = 6.2 Hz, 3H), 1.22 (d, J = 7.0 Hz, 6H) | — |
| 44 | 128-130 | — | ESIMS m/z 439 ([M + H]⁺) | ¹H NMR (300 MHz, CDCl₃) δ 11.81 (s, 1H), 8.67 (d, J = 8.3 Hz, 1H), 8.01 (dd, J = 5.2, 0.5 Hz, 2H), 6.90 (d, J = 5.2 Hz, 2H), 5.62-5.37 (m, 1H), 5.30-5.16 (m, J = 14.9, 8.1 Hz, 2H), 5.09 (q, J = 9.5 Hz, 2H), 5.02-4.89 (m, 2H), 3.95 (s, 3H), 3.81 (s, 1H), 3.45-3.29 (m, 2H), 3.27 (s, 2H), 2.85-2.72 (m, 1H), 2.62 (ddd, J = 11.8, 8.1, 5.9 Hz, 1H), 2.08-1.92 (m, 2H), 1.84-1.57 (m, 2H), 1.30 (d, J = 6.2 Hz, 3H), 1.22 (d, J = 7.0 Hz, 6H) | — |
| 45 | 134-136 | — | ESIMS m/z 497 ([M + H]⁺) | ¹H NMR (300 MHz, CDCl₃) δ 11.81 (s, 1H), 8.66 (d, J = 8.0 Hz, 1H), 8.01 (d, J = 5.1 Hz, 1H), 6.89 (d, J = 5.2 Hz, 1H), 5.48 (s, 1H), 5.20 (d, J = 6.8 Hz, 1H), 5.11 (t, J = 9.9 Hz, 1H), 5.03-4.89 (m, 1H), 3.95 (s, 3H), 3.78 (s, 1H), 3.46-3.32 (m, 4H), 2.84-2.69 (m, | — |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 1H), 2.69-2.55 (m, 1H), 2.01 (dt, J = 11.3, 4.8 Hz, 1H), 1.61 (m, 1H), 1.30 (d, J = 6.2 Hz, 3H), 1.21 (d, J = 7.0 Hz, 6H), 1.13 (t, J = 7.0 Hz, 3H) | |
| 46 | 198-200 | — | ESIMS m/z 439 ([M + H]⁺) | ¹H NMR (300 MHz, CDCl₃) δ 11.80 (s, 1H), 8.65 (d, J = 7.9 Hz, 1H), 8.01 (d, J = 5.2 Hz, 1H), 6.89 (d, J = 5.2 Hz, 1H), 5.54-5.31 (m, 1H), 5.19 (dd, J = 15.3, 8.1 Hz, 1H), 5.04 (t, J = 9.7 Hz, 1H), 4.94 (td, J = 12.2, 6.1 Hz, 1H), 3.95 (s, 3H), 3.78 (s, 1H), 2.65 (ddt, J = 20.9, 13.8, 6.8 Hz, 2H), 1.30 (d, J = 6.1 Hz, 3H), 1.22 (d, J = 7.0 Hz, 6H), 1.16 (d, J = 6.7 Hz, 3H) | — |
| 47 | 192-194 | — | ESIMS m/z 539 ([M + H]⁺) | ¹H NMR (400 MHz, CDCl₃) δ 11.79 (d, J = 0.5 Hz, 1H), 8.63 (d, J = 8.3 Hz, 1H), 8.01 (d, J = 5.2 Hz, 1H), 6.89 (d, J = 5.1 Hz, 1H), 5.45 (s, 1H), 5.21 (dd, J = 15.5, 8.3 Hz, 1H), 5.12-5.01 (m, 1H), 5.01-4.87 (m, 1H), 3.95 (s, 3H), 3.80 (d, J = 25.0 Hz, 1H), 2.98 (ddd, J = 11.8, 9.9, 3.2 Hz, 1H), 2.86-2.74 (m, 1H), 2.62 (dt, J = 14.0, 7.0 Hz, 1H), 2.35-2.23 (m, 1H), 1.41 (s, 9H), 1.30 (dd, J = 6.2, 2.4 Hz, 3H), 1.22 (dd, J = 7.0, 1.6 Hz, 6H) | ¹³C NMR (101 MHz, CDCl₃) δ 175.50, 172.00, 170.26, 169.90, 169.01, 155.45, 148.86, 140.73, 129.97, 109.74, 81.74, 74.79, 74.07, 65.03, 56.13, 49.80, 45.81, 34.93, 34.02, 27.97, 18.96, 18.84, 17.79 |
| 48 | 176-178 | — | ESIMS m/z 559 ([M + H]⁺) | ¹H NMR (300 MHz, CDCl₃) δ 11.77 (s, 1H), 8.62 (d, J = 8.4 Hz, 1H), 8.01 (d, J = 5.2 Hz, 1H), 7.36 (t, J = 7.7 Hz, 2H), 7.26-7.16 (m, 1H), 7.12-6.98 (m, 2H), 6.89 (d, J = 5.2 Hz, 1H), 5.44 (s, 1H), 5.19 (dt, J = 18.7, 8.6 Hz, 2H), 5.05-4.92 (m, 1H), 3.95 (s, 3H), 3.82 (s, 1H), 3.23-3.07 (m, 2H), 2.65 (dd, J = 13.2, 6.2 Hz, 2H), 1.33 (d, J = 6.2 Hz, 3H), 1.25 (dd, J = 7.0, 1.4 Hz, 6H) | — |
| 49 | 169-170 | — | ESIMS m/z 525 ([M + H]⁺) | ¹H NMR (300 MHz, CDCl₃) δ 11.79 (s, 1H), 8.63 (d, J = 8.4 Hz, 1H), 8.01 (d, J = 5.2 Hz, 1H), 6.89 (d, J = 5.2 Hz, 1H), 5.57-5.32 (m, 1H), 5.21 (dd, J = 15.6, 8.3 Hz, 1H), 5.07 (t, J = 9.8 Hz, 1H), 4.97 (dt, J = 16.2, 5.6 Hz, 2H), 3.95 (s, 3H), 3.83 (s, 1H), 3.09-2.95 (m, 1H), 2.85 (dd, J = 17.1, 11.7 Hz, 1H), 2.62 (dt, J = 14.0, 7.0 Hz, 1H), 2.34 (dd, J = 17.1, 3.1 Hz, | — |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 1H), 1.30 (d, J = 6.1 Hz, 3H), 1.27-1.14 (m, 12H) | |
| 50 | 138-140 | — | ESIMS m/z 497 ([M + H]⁺) | ¹H NMR (300 MHz, CDCl₃) δ 11.74 (s, 1H), 8.67-8.52 (m, 1H), 8.05-7.76 (m, 1H), 6.85 (d, J = 5.2 Hz, 1H), 5.53-5.28 (m, 1H), 5.26-5.11 (m, 1H), 5.03 (t, J = 9.8 Hz, 1H), 4.98-4.84 (m, 1H), 3.91 (s, 3H), 3.88-3.75 (m, 1H), 3.63 (s, 3H), 3.03 (ddd, J = 11.6, 7.6, 3.2 Hz, 1H), 2.92-2.79 (m, 1H), 2.65-2.50 (m, 1H), 2.43-2.30 (m, 1H), 1.32-1.23 (m, 3H), 1.18 (d, J = 7.0 Hz, 6H) | — |
| 51 | 103-105 | — | ESIMS m/z 497 ([M + H]⁺) | ¹H NMR (300 MHz, CDCl₃) δ 11.78 (s, 1H), 8.64 (d, J = 7.9 Hz, 1H), 8.09-7.92 (m, 2H), 6.90 (d, J = 5.3 Hz, 1H), 5.47 (s, 1H), 5.21 (d, J = 7.0 Hz, 1H), 5.11 (t, J = 9.9 Hz, 1H), 5.01-4.88 (m, 1H), 4.21 (dt, J = 11.0, 5.4 Hz, 1H), 4.14-4.00 (m, 1H), 3.95 (s, 3H), 3.79 (s, 1H), 2.84-2.69 (m, 1H), 2.63 (dt, J = 14.0, 7.0 Hz, 1H), 2.20-2.06 (m, 1H), 1.78 (s, 1H), 1.31 (d, J = 6.2 Hz, 3H), 1.22 (d, J = 7.0 Hz, 6H) | — |
| 52 | 195-196 | — | ESIMS m/z 489 ([M + H]⁺) | ¹H NMR (300 MHz, CDCl₃) δ 11.76 (s, 1H), 8.64 (d, J = 8.1 Hz, 1H), 8.01 (d, J = 5.2 Hz, 1H), 6.89 (d, J = 5.2 Hz, 1H), 6.06-5.60 (m, 1H), 5.45 (s, 1H), 5.22 (dd, J = 15.5, 8.1 Hz, 1H), 5.09 (t, J = 9.8 Hz, 1H), 5.03-4.90 (m, 1H), 3.95 (s, 3H), 3.81 (s, 1H), 2.94-2.80 (m, 1H), 2.64 (dt, J = 14.0, 7.0 Hz, 1H), 2.58-2.33 (m, 1H), 1.92-1.72 (m, 1H), 1.32 (d, J = 6.2 Hz, 3H), 1.23 (dd, J = 9.6, 2.8 Hz, 6H) | — |
| 53 | 193-195 | — | ESIMS m/z 453 ([M + H]⁺) | ¹H NMR (300 MHz, CDCl₃) δ 11.81 (s, 1H), 8.66 (d, J = 8.1 Hz, 1H), 8.01 (d, J = 5.2 Hz, 1H), 6.89 (d, J = 5.2 Hz, 1H), 5.47 (s, 1H), 5.20 (dd, J = 14.7, 8.1 Hz, 1H), 5.08 (t, J = 9.9 Hz, 1H), 4.93 (dq, J = 9.7, 6.3 Hz, 1H), 3.95 (s, 3H), 3.78 (m, 1H), 2.70-2.57 (m, 1H), 2.52 (ddd, J = 11.5, 7.4, 2.5 Hz, 1H), 1.81-1.63 (m, 2H), 1.53-1.34 (m, 2H), 1.29 (d, J = 6.2 Hz, 3H), 1.21 (d, 6H), 0.88 (t, J = 7.4 Hz, 3H) | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| 54 | 222-224 | — | ESIMS m/z 631 ([M + H]$^+$) | $^1$H NMR (300 MHz, CDCl$_3$) δ 11.75 (s, 1H), 8.64 (d, J = 8.1 Hz, 1H), 8.01 (d, J = 5.2 Hz, 1H), 7.82 (s, 1H), 7.70 (d, J = 7.6 Hz, 2H), 7.36 (dd, J = 13.8, 6.4 Hz, 2H), 6.90 (d, J = 5.2 Hz, 1H), 5.46 (s, 1H), 5.21 (d, J = 8.1 Hz, 1H), 5.12 (t, J = 9.7 Hz, 1H), 4.96-4.86 (m, 1H), 4.51-4.31 (m, 2H), 3.96 (s, 3H), 3.89-3.76 (m, 1H), 2.75-2.54 (m, 2H), 2.37 (s, 1H), 2.14 (s, 1H), 1.30 (d, J = 6.2 Hz, 3H), 1.20 (d, J = 7.0 Hz, 6H) | — |
| 55 | 222-224 | — | ESIMS m/z 596 ([M + H]$^+$) | $^1$H NMR (300 MHz, CDCl$_3$) δ 11.76 (s, 1H), 8.64 (d, J = 8.2 Hz, 1H), 8.01 (d, J = 5.2 Hz, 1H), 7.89-7.77 (m, 2H), 7.70 (s, 1H), 7.51-7.30 (m, 3H), 6.89 (d, J = 5.2 Hz, 1H), 5.46 (s, 1H), 5.32-5.18 (m, 1H), 5.12 (t, J = 9.8 Hz, 1H), 4.90 (dq, J = 12.6, 6.3 Hz, 1H), 4.50-4.26 (m, 2H), 3.95 (s, 3H), 3.81 (s, 1H), 2.75-2.51 (m, 2H), 2.36 (dd, J = 16.7, 9.0 Hz, 1H), 2.12 (s, 1H), 1.30 (d, J = 6.3 Hz, 3H), 1.19 (d, J = 7.0 Hz, 6H) | — |
| 56 | 153-155 | — | ESIMS m/z 547 ([M + H]$^+$) | $^1$H NMR (CDCl$_3$) δ 11.76 (d, J = 0.5 Hz, 1H), 8.65 (d, J = 8.1 Hz, 1H), 8.02 (d, J = 5.2 Hz, 1H), 6.90 (d, J = 5.2 Hz, 1H), 5.47 (s, 1H), 5.20 (dd, J = 15.2, 7.8 Hz, 1H), 5.16-5.05 (m, 1H), 4.96 (dq, J = 9.8, 6.2 Hz, 1H), 4.28 (dt, J = 10.5, 5.3 Hz, 1H), 4.20-4.07 (m, 1H), 3.95 (s, 3H), 3.78 (d, J = 12.1 Hz, 1H), 2.98 (d, J = 1.4 Hz, 3H), 2.89-2.82 (m, 1H), 2.63 (hept, J = 7.0 Hz, 1H), 2.24-2.10 (m, J = 11.2, 4.7 Hz, 1H), 1.94-1.79 (m, J = 8.6, 5.8 Hz, 1H), 1.35-1.28 (m, 3H), 1.22 (dd, J = 7.0, 0.9 Hz, 6H) | — |
| 57 | 183-184 | — | ESIMS m/z 529 ([M + H]$^+$) | $^1$H NMR (300 MHz, CDCl$_3$) δ 11.80 (s, 1H), 8.66 (d, J = 8.1 Hz, 1H), 8.01 (d, J = 5.2 Hz, 1H), 7.34-7.15 (m, 3H), 7.15-7.02 (m, 2H), 6.89 (d, J = 5.2 Hz, 1H), 5.50 (s, 1H), 5.21 (dd, J = 15.1, 7.6 Hz, 1H), 5.10 (t, J = 9.9 Hz, 1H), 4.96-4.83 (m, 1H), 3.95 (s, 3H), 3.80 (s, 1H), 2.78-2.51 (m, 3H), 2.51-2.35 (m, 1H), 2.21-2.06 (m, | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 1H), 1.73-1.58 (m, 1H), 1.28 (d, J = 6.2 Hz, 3H), 1.18 (d, J = 7.0 Hz, 6H) | |
| 58 | 142-144 | — | ESIMS m/z 547 ([M + H]$^+$) | $^1$H NMR (CDCl$_3$) δ 11.88-11.72 (m, 1H), 8.66 (d, J = 8.1 Hz, 1H), 8.01 (dd, J = 5.2, 1.0 Hz, 1H), 7.13-7.02 (m, 1H), 7.02-6.92 (m, 1H), 6.90 (d, J = 5.2 Hz, 1H), 5.49 (s, 1H), 5.21 (d, J = 6.0 Hz, 1H), 5.15-5.02 (m, 1H), 5.02-4.86 (m, 1H), 3.95 (d, J = 1.0 Hz, 3H), 3.78 (d, J = 11.6 Hz, 1H), 2.76-2.47 (m, 3H), 2.47-2.33 (m, 1H), 2.17-2.01 (m, 1H), 1.79-1.70 (m, 1H), 1.65-1.53 (m, 1H), 1.50-1.36 (m, 1H), 1.31-1.26 (m, 3H), 1.23-1.15 (m, 6H) | — |
| 59 | 169-170 | — | ESIMS m/z 530 ([M + H]$^+$) | $^1$H NMR (300 MHz, CDCl$_3$) δ 11.79 (s, 1H), 8.66 (d, J = 8.2 Hz, 1H), 8.46 (dd, J = 4.8, 1.6 Hz, 1H), 8.40 (d, J = 1.7 Hz, 1H), 8.02 (d, J = 5.2 Hz, 1H), 7.51-7.39 (m, 1H), 7.26-7.17 (m, 1H), 6.90 (d, J = 5.2 Hz, 1H), 5.50 (s, 1H), 5.21 (dd, J = 15.1, 8.2 Hz, 1H), 5.11 (t, J = 9.9 Hz, 1H), 4.91 (dq, J = 12.6, 6.3 Hz, 1H), 3.96 (s, 3H), 3.81 (s, 1H), 2.76-2.37 (m, 3H), 2.25-2.04 (m, 1H), 1.81-1.56 (m, 2H), 1.28 (d, J = 6.3 Hz, 3H), 1.18 (dd, J = 7.0, 1.3 Hz, 6H) | — |
| 60 | 139-140 | — | ESIMS m/z 559 ([M + H]$^+$) | $^1$H NMR (300 MHz, CDCl$_3$) δ 11.81 (s, 1H), 8.65 (d, J = 8.3 Hz, 1H), 8.01 (d, J = 5.2 Hz, 1H), 7.40-7.23 (m, 5H), 6.89 (d, J = 5.2 Hz, 1H), 5.50-5.30 (m, 1H), 5.28-5.05 (m, 2H), 5.03-4.87 (m, 1H), 4.44 (s, 2H), 3.95 (s, 3H), 3.71 (s, 1H), 3.57-3.34 (m, 2H), 2.83 (td, J = 11.5, 2.8 Hz, 1H), 2.61 (hept, J = 7.0 Hz, 1H), 2.15-1.98 (m, 1H), 1.78-1.56 (m, 1H), 1.29 (d, J = 6.2 Hz, 3H), 1.21 (d, J = 7.0 Hz, 6H) | — |
| 61 | 188-189 | — | ESIMS m/z 521 ([M + H]$^+$) | $^1$H NMR (CDCl$_3$) δ 11.80 (s, 1H), 8.58 (t, J = 42.0 Hz, 1H), 8.01 (d, J = 5.2 Hz, 1H), 6.88 (d, J = 5.2 Hz, 1H), 5.48 (s, 1H), 5.18 (d, J = 6.9 Hz, 1H), 5.05 (td, J = 9.9, 5.8 Hz, 1H), 5.00-4.84 (m, 1H), 3.95 (s, 3H), 3.76 (s, 1H), 2.76-2.66 (m, 1H), 2.65-2.54 (m, 1H), 1.83-1.58 (m, | — |

TABLE 2-continued

Analytical Data

| Compound Number | MP (° C.) | IR (cm$^{-1}$) | MASS | $^1$H NMR* | $^{13}$C NMR* |
|---|---|---|---|---|---|
| | | | | 7H), 1.29 (dd, J = 6.2, 2.5 Hz, 3H), 1.21 (dd, J = 7.0, 3.1 Hz, 6H), 1.13 (m, J = 31.1, 15.2, 7.8 Hz, 6H) | |
| 62 | — | — | — | $^1$H NMR (CDCl$_3$) δ 11.80 (s, 1H), 8.61 (t, J = 25.3 Hz, 1H), 8.00 (d, J = 5.2 Hz, 1H), 6.88 (d, J = 5.2 Hz, 1H), 5.40 (d, J = 45.6 Hz, 1H), 5.18 (dd, J = 14.8, 7.9 Hz, 1H), 5.08 (td, J = 9.9, 4.8 Hz, 1H), 4.93 (dq, J = 9.8, 6.2 Hz, 1H), 3.95 (s, 3H), 3.77 (d, J = 6.4 Hz, 1H), 2.62 (dq, J = 14.0, 7.0 Hz, 1H), 2.57-2.46 (m, 1H), 1.69 (m, 8H), 1.0 (d, J = 9.5 Hz, 3H), 1.22 (dd, J = 7.0, 2.3 Hz, 6H), 1.19-0.97 (m, 6H) | $^{13}$C NMR (CDCl$_3$) δ 175.54, 172.69, 169.75, 169.02, 155.47, 148.89, 140.70, 130.04, 109.74, 75.29, 74.90, 65.08, 56.11, 50.34, 50.08, 37.33, 34.67, 34.14, 33.27, 32.89, 26.55, 26.24, 26.17, 25.82, 18.98, 18.91, 17.78 |
| 63 | 131-134 | — | ESIMS m/z 523.4 ([M + H]$^+$) | $^1$H NMR (CDCl$_3$) δ 11.81 (s, 1H), 8.66 (d, J = 8.1 Hz, 1H), 8.01 (d, J = 5.2 Hz, 1H), 6.89 (d, J = 5.2 Hz, 1H), 5.19 (m, 1H), 5.14-5.02 (m, 1H), 5.02-4.87 (m, 1H), 3.95 (s, 3H), 3.87-3.69 (m, 1H), 2.70-2.52 (m, 2H), 1.80-1.66 (m, 1H), 1.43-1.08 (m, 21H), 0.86 (t, J = 6.8 Hz, 3H) | — |
| 64 | 165-168 | — | ESIMS m/z 467.3 ([M + H]$^+$) | $^1$H NMR (CDCl$_3$) δ 11.81 (s, 1H), 8.66 (d, J = 8.1 Hz, 1H), 8.01 (d, J = 5.2 Hz, 1H), 6.89 (d, J = 5.2 Hz, 1H), 5.47 (br s, 1H), 5.19 (dd, J = 14.9, 7.6 Hz, 1H), 5.08 (t, J = 9.9 Hz, 1H), 4.94 (dq, J = 9.8, 6.2 Hz, 1H), 3.95 (s, 3H), 3.85-3.69 (m, 1H), 2.68-2.53 (m, 2H), 1.83-1.69 (m, 1H), 1.29 (d, J = 6.3 Hz, 3H), 1.40-1.10 (m, 3H); 1.22 (dd, J = 7.0, 1.8 Hz, 6H), 0.88 (t, J = 7.1 Hz, 3H) | — |
| 65 | 148-150 | (Neat) 3356, 2976, 2943, 1742, 1653 | ESIMS m/z 548 ([M + H]$^+$) | $^1$H NMR (CDCl$_3$) δ 11.81 (s, 1H), 8.61 (d, J = 8.4 Hz, 1H), 8.41-8.36 (m, 1H), 8.01 (d, J = 5.2 Hz, 1H), 7.51-7.44 (m, 1H), 7.17-7.12 (m, 1H), 7.01 (ddd, J = 7.2, 4.9, 1.0 Hz, 1H), 6.90 (d, J = 5.2 Hz, 1H), 5.50 (bs, 1H), 5.29-5.13 (m, 2H), 4.97 (dd, J = 9.8, 6.2 Hz, 1H), 3.97 (s, 3H), 3.68 (m, 2H), 3.16 (t, J = 9.4 Hz, 2H), 2.73 (dt, J = 14.0, 7.1 Hz, 1H), 1.38-1.28 (m, 9H) | $^{13}$C NMR (CDCl$_3$) δ 176.21, 172.00, 170.30, 169.38, 157.47, 155.81, 149.78, 149.19, 141.19, 136.46, 130.27, 122.94, 120.20, 110.13, 75.08, 65.47, 56.59, 51.20, 50.09, 39.06, 34.70, 28.67, 19.45, 19.28, 18.19 |
| 66 | 164-170 | — | HRMS-ESI (m/z) calcd for C$_{28}$H$_{38}$N$_2$O$_{10}$, | $^1$H NMR (CDCl$_3$) δ 8.70 (d, J = 7.5 Hz, 1H), 8.35 (d, J = 5.4 Hz, 1H), 7.03 (d, J = 5.5 Hz, 1H), | — |

TABLE 2-continued

Analytical Data

| Compound Number | MP (° C.) | IR (cm⁻¹) | MASS | ¹H NMR* | ¹³C NMR* |
|---|---|---|---|---|---|
| | | | 562.2526; found, 562.2516 | 5.47 (br s, 1H), 5.25-5.11 (m, 1H), 5.03 (t, J = 9.9 Hz, 1H), 4.97-4.84 (m, 1H), 3.92 (s, 3H), 3.72 (br s, 1H), 2.69 (dd, J = 16.8, 7.0 Hz, 1H), 2.60 (sept, J = 14.0, 7.0 Hz, 1H), 2.40 (s, 3H), 1.83-1.54 (m, 6H), 1.36-1.02 (m, 14H), 0.94-0.67 (m, 2H) | |
| 67 | 127-134 | — | HRMS-ESI (m/z) calcd for $C_{29}H_{31}F_3N_2O_{10}$, 624.1931; found, 624.1954 | ¹H NMR (CDCl₃) δ 8.64 (d, J = 8.0 Hz, 1H), 8.33 (d, J = 5.4 Hz, 1H), 7.52 (d, J = 8.1 Hz, 2H), 7.24 (d, J = 8.1 Hz, 2H), 7.01 (d, J = 5.5 Hz, 1H), 5.33 (br s, 1H), 5.26-5.11 (m, 2H), 4.97 (dq, J = 12.2, 6.1 Hz, 1H), 3.91 (s, 3H), 3.58 (br s, 1H), 3.05 (t, J = 12.5 Hz, 1H), 2.98-2.87 (m, 1H), 2.74 (d, J = 12.5 Hz, 1H), 2.63 (td, J = 13.9, 6.9 Hz, 1H), 2.38 (s, 3H), 1.31 (d, J = 6.3 Hz, 3H), 1.24 (d, J = 7.0 Hz, 6H) | — |
| 68 | 199-200 | — | HRMS-ESI (m/z) calcd for $C_{31}H_{33}F_3N_2O_{12}$, 682.1986; found, 682.2022 | ¹H NMR (CDCl₃) δ 8.68 (d, J = 7.8 Hz, 1H), 8.34 (d, J = 5.4 Hz, 1H), 8.08 (d, J = 8.1 Hz, 2H), 7.72 (d, J = 8.2 Hz, 2H), 7.03 (d, J = 5.5 Hz, 1H), 5.40 (br s, 1H), 5.26-5.06 (m, 2H), 4.95 (dq, J = 12.5, 6.2 Hz, 1H), 4.43-4.25 (m, 2H), 3.91 (s, 3H), 3.64 (br s, 1H), 2.82-2.71 (m, 1H), 2.68-2.58 (m, 1H), 2.40 (s, 3H), 2.37-2.23 (m, 1H), 1.88-1.76 (m, 1H), 1.29 (d, J = 6.3 Hz, 3H), 1.22 (dd, J = 7.0, 0.9 Hz, 6H) | — |
| 69 | 158-161 | — | HRMS-ESI (m/z) calcd for $C_{23}H_{30}N_2O_{10}$, 494.1900; found, 494.1919 | ¹H NMR (CDCl₃) δ 8.71 (d, J = 7.8 Hz, 1H), 8.35 (d, J = 5.4 Hz, 1H), 7.03 (d, J = 5.5 Hz, 1H), 5.46 (br s, 1H), 5.18 (dd, J = 14.7, 7.7 Hz, 1H), 5.11-5.00 (m, 1H), 4.98-4.85 (m, 1H), 3.92 (s, 3H), 3.73 (br s, 1H), 2.60 (dt, J = 14.0, 7.0 Hz, 1H), 2.55-2.45 (m, 1H), 2.40 (s, 3H), 1.71 (ddd, J = 13.2, 11.7, 7.2 Hz, 1H), 1.41 (m, 1H), 1.27 (d, J = 6.3 Hz, 3H), 1.21 (d, J = 7.0 Hz, 6H), 0.87 (t, J = 7.4 Hz, 3H) | — |
| 70 | 151-160 | — | HRMS-ESI (m/z) calcd for $C_{27}H_{31}N_3O_{10}$, 557.2009; found, 557.2015 | ¹H NMR (CDCl₃) δ 8.64 (d, J = 8.0 Hz, 1H), 8.46 (d, J = 3.4 Hz, 1H), 8.41 (s, 1H), 8.33 (d, J = 5.4 Hz, 1H), 7.52-7.43 (m, 1H), 7.20 (dd, J = 7.8, 4.8 Hz, 1H), 7.01 (d, J = 5.5 Hz, 1H), 5.33 (br s, 1H), 5.19 (m, J = 18.9, 9.1 Hz, 2H), 5.08-4.88 (m, 1H), 3.91 (s, 3H), | — |

TABLE 2-continued

Analytical Data

| Compound Number | MP (° C.) | IR (cm⁻¹) | MASS | ¹H NMR* | ¹³C NMR* |
|---|---|---|---|---|---|
| | | | | 3.59 (br s, 1H), 3.06-2.83 (m, 2H), 2.75-2.60 (m, 2H), 2.39 (s, 3H), 1.31 (d, J = 6.3 Hz, 3H), 1.25 (dd, J = 7.0, 2.0 Hz, 6H) | |

*¹H NMR were recorded at 400 MHz unless noted otherwise.
*¹³C NMR were recorded at 101 MHz unless noted otherwise.

TABLE 3

Biological Testing Rating Scale
PUCCRT* and SEPTTR* Rating Table

| % Control | Rating |
|---|---|
| 50-100 | A |
| More than 0-Less than 50 | B |
| Not Tested | C |
| No activity noticed in this bioassay | D |

*PUCCRT - Wheat Brown Rust (*Puccinia triticina*)
*SEPTTR - Wheat Leaf Blotch (*Septoria tritici*)

TABLE 4

Biological Activity - Disease Control at 100 ppm

| Compound Number | PUCCRT* 1DP* | PUCCRT* 3DC* | SEPTTR* 1DP | SEPTTR* 3DC |
|---|---|---|---|---|
| 1 | A | B | A | B |
| 2 | A | A | A | A |
| 3 | A | A | A | A |
| 4 | A | B | A | B |
| 5 | A | A | A | A |
| 6 | A | D | A | B |
| 7 | A | A | B | B |
| 8 | A | A | A | B |
| 9 | A | A | A | B |
| 10 | A | A | A | B |
| 11 | A | A | A | B |
| 12 | A | B | A | B |
| 13 | A | B | A | B |
| 14 | A | A | B | B |
| 15 | A | B | A | B |
| 16 | A | B | A | B |
| 17 | A | A | A | B |
| 18 | A | D | A | B |
| 19 | A | A | A | B |
| 20 | A | A | A | A |
| 21 | A | A | A | A |
| 22 | A | A | B | B |
| 23 | A | A | B | B |
| 24 | A | A | A | B |
| 25 | A | A | A | B |
| 26 | A | A | B | B |
| 27 | B | B | B | B |
| 28 | A | A | A | A |
| 29 | A | A | A | B |
| 30 | A | A | A | A |
| 31 | A | B | B | B |
| 32 | A | A | A | A |
| 33 | A | A | A | A |
| 34 | A | A | A | A |
| 35 | A | D | A | D |
| 36 | A | D | A | B |
| 37 | A | B | A | B |
| 38 | A | D | A | B |
| 39 | A | B | A | B |
| 40 | A | D | A | B |
| 41 | A | D | B | B |
| 42 | A | D | B | B |
| 43 | A | B | A | B |
| 44 | A | A | A | A |
| 45 | A | A | B | B |
| 46 | A | B | A | D |
| 47 | A | A | A | A |
| 48 | A | D | A | B |
| 49 | A | A | A | A |
| 50 | A | A | A | A |
| 51 | A | D | B | B |
| 52 | A | B | A | B |
| 53 | A | D | A | B |
| 54 | A | D | A | B |
| 55 | A | B | A | B |
| 56 | A | B | B | B |
| 57 | A | A | A | B |
| 58 | A | A | A | B |
| 59 | A | B | B | B |
| 60 | A | A | A | B |
| 61 | A | B | A | A |
| 62 | A | B | A | B |
| 63 | A | D | A | B |
| 64 | A | B | A | A |
| 65 | A | B | A | B |
| 66 | A | A | A | A |
| 67 | A | A | B | D |
| 68 | B | B | B | B |
| 69 | A | A | A | A |
| 70 | A | A | B | B |

*PUCCRT - Wheat Brown Rust (*Puccinia triticina*)
*SEPTTR - Wheat Leaf Blotch (*Septoria tritici*)
*1DP - 1 Day Protectant
*3DC - 3 Day Curative

What is claimed:

1. A compound of Formula I:

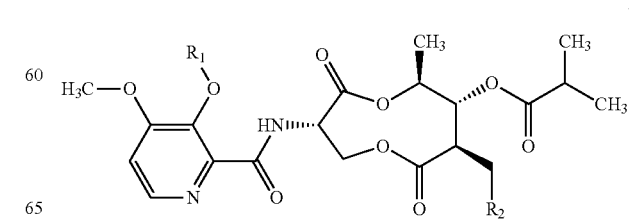

wherein $R_1$ is —$CH_2OC(O)R_3$;
$R_2$ is H, halogen, alkyl, alkenyl, alkynyl, heterocyclyl, alkylthio, arylthio or heteroarylthio each substituted with 0, 1 or multiple $R_5$, —$CH_2R_4$, —$CH_2OC(O)R_{R4}$, —$C(O)OR_4$, —$CH_2OS(O)_2R_4$, or —$CH_2OR_4$;
$R_3$ is alkyl or alkoxy, substituted with 0, 1, or multiple $R_5$;
$R_4$ is H, alkyl, aryl, arylalkyl, or heterocyclyl, each substituted with 0, 1 or multiple $R_5$;
$R_5$ is alkyl, alkenyl, halo, haloalkyl, alkoxy, haloalkoxy, arylalkoxy, cyano, aryl or heterocyclyl, each substituted with 0, 1 or multiple $R_6$; and $R_6$ is alkyl, alkenyl, halo, haloalkyl, alkoxy, haloalkoxy, arylalkoxy, cyano, aryl or heterocyclyl.

2. A compound of Formula I:

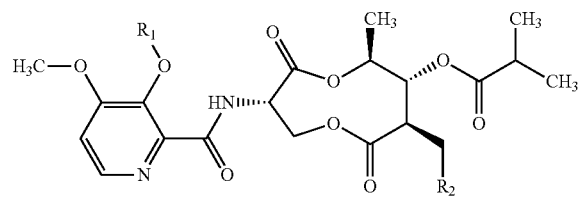

wherein $R_1$ is H, —$C(O)R_3$, or —$CH_2OC(O)R_3$;
$R_2$ is aryl substituted with 1 or multiple $R_5$, —$CH_2R_4$, —$CH_2OC(O)R_4$, —$C(O)OR_4$, —$CH_2OS(O)_{2\ R4}$, or —$CH_2OR_4$, wherein the substituent is not methyl;
$R_3$ is alkyl or alkoxy, substituted with 0, 1, or multiple $R_5$;
$R_4$ is H, alkyl, alkenyl, aryl, arylalkyl, or heterocyclyl, each substituted with 0, 1 or multiple $R_5$;
$R_5$ is alkyl, alkenyl, halo, haloalkyl, alkoxy, haloalkoxy, arylalkoxy, cyano, aryl or heterocyclyl, each substituted with 0, 1 or multiple $R_6$;
$R_6$ is alkyl, alkenyl, halo, haloalkyl, alkoxy, haloalkoxy, arylalkoxy, cyano, aryl or heterocyclyl.

3. A composition for the control of a fungal pathogen, the composition including:
at least one compound according to claim 1, and
at least one phytologically acceptable carrier and/or at least one agriculturally active ingredient selected from the group consisting of pesticides, fungicides, insecticides, nematocides, miticides, arthropodicides, bactericides and combinations thereof.

4. A method for treating a plant, comprising the step of:
applying an amount of at least one compound according to claim 1 to at least one portion of a plant, an area adjacent to a plant, and/or soil adapted to support growth of a plant, wherein said amount is effective for the control of at least one plant pathogenic fungi.

5. A composition for the control of a fungal pathogen, the composition including:
at least one compound according to claim 2, and
at least one phytologically acceptable carrier and/or at least one agriculturally active ingredient selected from the group consisting of pesticides, fungicides, insecticides, nematocides, miticides, arthropodicides, bactericides and combinations thereof.

6. A method for treating a plant, comprising the step of:
applying an amount of at least one compound according to claim 2 to at least one portion of a plant, an area adjacent to a plant, and/or soil adapted to support growth of a plant, wherein said amount is effective for the control of at least one plant pathogenic fungi.

* * * * *